United States Patent
Gao et al.

(10) Patent No.: US 11,649,254 B2
(45) Date of Patent: May 16, 2023

(54) COMPOUND, A DISPLAY PANEL AND AN ELECTRONIC DEVICE

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Wei Gao, Shanghai (CN); Wenpeng Dai, Shanghai (CN); Lei Zhang, Shanghai (CN); Wenjing Xiao, Shanghai (CN); Jinghua Niu, Shanghai (CN); Sha Lin, Shanghai (CN)

(73) Assignee: WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 366 days.

(21) Appl. No.: 16/874,514

(22) Filed: May 14, 2020

(65) Prior Publication Data
US 2020/0270278 A1 Aug. 27, 2020

(30) Foreign Application Priority Data
Oct. 31, 2019 (CN) .......................... 201911053520.8

(51) Int. Cl.
*H01L 51/50* (2006.01)
*C07F 5/02* (2006.01)
(Continued)

(52) U.S. Cl.
CPC .............. *C07F 5/02* (2013.01); *C07D 487/04* (2013.01); *C07D 519/00* (2013.01);
(Continued)

(58) Field of Classification Search
None
See application file for complete search history.

(56) References Cited

FOREIGN PATENT DOCUMENTS

| CN | 102754237 A | 10/2012 |
|---|---|---|
| CN | 103384671 A | 11/2013 |

(Continued)

OTHER PUBLICATIONS

Irgashev et al. "Synthesis, photophysical and electrochemical properties of novel 6,12-di (thiophen-2-yl) substituted indolo [3, 2-b] carbazoles", Tetrahedron 70 (2014): 4685-4696. (Year: 2014).*

(Continued)

*Primary Examiner* — Robert S Loewe
(74) *Attorney, Agent, or Firm* — Alston & Bird LLP

(57) ABSTRACT

The present disclosure provides a compound for a display panel. The compound includes elements selected from O, S or N, electron-donor groups and electron-accepting groups. The OLED device in the display panel includes an anode, a cathode, and at least one organic thin film layer between the anode and the cathode. The organic thin film layer includes a light emitting layer, the light emitting layer includes the compound of the present disclosure, and the compound is used to be any one of a host material, a doping material, and a co-doping material. The compound reduces energy level difference between singlet and triplet states $\Delta E_{ST}$ through design of the compound molecular structure. The compound realizes an efficient reverse intersystem crossing process, has typical TADF characteristics, and can be used as a light-emitting layer material of an OLED device to improve luminous efficiency and working life.

16 Claims, 2 Drawing Sheets

(51) Int. Cl.
  *C07D 487/04*   (2006.01)
  *C07D 519/00*   (2006.01)
  *C07F 9/6561*   (2006.01)
  *C07F 9/6571*   (2006.01)
  *C07F 9/6578*   (2006.01)
  *H01L 51/00*    (2006.01)

(52) U.S. Cl.
  CPC .......... *C07F 9/6561* (2013.01); *C07F 9/6578* (2013.01); *C07F 9/657163* (2013.01); *H01L 51/008* (2013.01); *H01L 51/0059* (2013.01); *H01L 51/0067* (2013.01); *H01L 51/0072* (2013.01); *H01L 51/0074* (2013.01); *H01L 51/5024* (2013.01); *H01L 51/5056* (2013.01); *H01L 51/5092* (2013.01); *H01L 51/5096* (2013.01)

(56) References Cited

FOREIGN PATENT DOCUMENTS

| CN | 110003260 A | 7/2019 | | |
|---|---|---|---|---|
| CN | 110041340 A | 7/2019 | | |
| JP | 2012236777 A | * | 12/2012 | .......... C07D 487/04 |
| KR | 20190106774 A | | 9/2019 | |
| TW | 201843155 A | | 12/2018 | |
| WO | 2006098229 A1 | | 9/2006 | |

OTHER PUBLICATIONS

Machine translation of CN-110003260, translation generated May 2022, 25 pages. (Year: 2022).*

Machine translation of JP-2012236777, translation generated May 2022, 27 pages. (Year: 2022).*

Nuligonda Thirupathi, Selective 5-exo-dig Cyclization of in Situ Synthesized N-Boc-2-aminophenyl Ethoxyethynyl Carbenols: Synthesis of Multifunctional Indoles and Their Derivatives, Nov. 10, 2013, 12 pages, published online Apr. 9, 2014. Niklas Wahlstrom, JOC Note, Synthetic Applications of Cyanoacetylated Bisindoles: Synthesis of Novel.

* cited by examiner

COMPOUND, A DISPLAY PANEL AND AN ELECTRONIC DEVICE

CROSS-REFERENCE TO RELATED APPLICATIONS

The application claims the benefit of the earlier filing date of Chinese Patent Application No. CN201911053520.8, filed on Oct. 31, 2019 to the China National Intellectual Property Administration (CNIPA), the contents of which are incorporated by reference herein in its entirety.

TECHNICAL FIELD

The present disclosure relates to the technical field of organic electroluminescent materials, and in particular relates to a compound, as well as a display panel and an electronic device including the compound.

BACKGROUND

Organic electroluminescence technology is an emerging technology with broad application prospects in the field of optoelectronics. Organic Light Emitting Diodes (OLEDs) have the advantages of being ultra-thin, self-luminous, wide viewing angles, fast response, high luminous efficiency, good temperature adaptability, simple production process, low driving voltage, and low energy consumption, etc., compared to traditional inorganic electroluminescent devices. Thus, it has been widely used in industrial applications such as flat panel display, flexible display, solid-state lighting and on-board display. At present time, OLEDs have entered the industrialization stage, however, the development of high-performance organic optoelectronic materials is still the focus of research in this field.

According to light-emitting mechanisms, there are mainly four types of materials that can be used in an OLED light-emitting layer: fluorescent materials, phosphorescent materials, triplet-triplet annihilation (TTA) materials, and thermally activated delayed fluorescent (TADF) materials. Among them, singlet excited state $S_1$ of fluorescent material returns to ground state $S_0$ through radiative transition. According to spin statistics, a ratio of singlet and triplet excitons is 1:3, thus the maximum internal quantum yield of the fluorescent material is less than 25%. According to Lambert luminescence mode, light extraction efficiency is about 20%, therefore external quantum efficiency (EQE) of an OLED device based on the fluorescent material does not exceed 5%. Triplet excited state $T_1$ in phosphorescent materials attenuates to ground state $S_0$ through direct radiation. Due to heavy atom effect, intramolecular intersystem crossing can be enhanced by spin coupling, and 75% of triplet excitons can be directly utilized, thereby realizing $S_1$ and $T_1$ co-participated emission at room temperature, and the theoretical maximum internal quantum yield can reach 100%. According to Lambert luminescence mode, light extraction efficiency is about 20%, thus EQE of the OLED device based on phosphorescent material can reach 20%. However, the phosphorescent materials are substantially complexes of heavy metals such as Ir, Pt, Os, Re, Ru., which have high production cost and are not conducive to large-scale production; and at high current density, serious efficiency roll-off phenomenon occurs in phosphorescent materials, meanwhile the phosphorescent device has poor stability. Two of triplet excitons of TTA materials interact and recombine to form a higher energy level of a molecule in singlet excited state and a molecule in ground state; but two triplet excitons produce one singlet exciton, therefore the theoretical maximum internal quantum yield can only reach 62.5%. In order to prevent a large efficiency roll-off phenomenon, it is necessary to regulate the concentration of triplet excitons during this process. TADF materials are mainly organic compounds, do not require rare metal elements, have low production costs, and can be chemically modified by various methods. Therefore, they have great application prospects, however, currently, fewer types of TADF materials have been disclosed, and their performance cannot meet requirements for use in OLED devices.

Therefore, developing more types of novel TADF materials with high performance is the focus of research in this field.

SUMMARY

According to one embodiment of the present disclosure, a compound is provided having a structure as shown in Formula I:

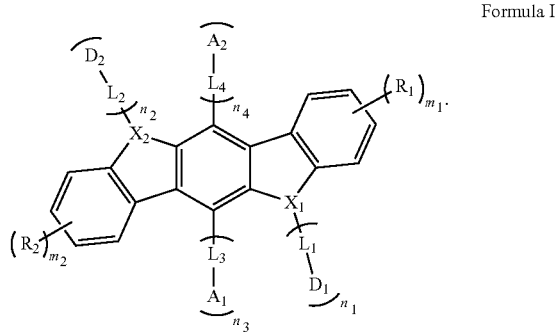

Formula I

In Formula I, $n_1$, $n_2$, $n_3$ and $n_4$ each is independently 0 or 1, and $n_3+n_4 \geq 1$, for example, $n_3+n_4=1$ or $n_3+n_4=2$.

In Formula I, $X_1$ and $X_2$ each is independently selected from oxygen (O), sulfur (S) or nitrogen (N).

When $X_1$ is O or S, $n_1$ is 0.

When $X_2$ is O or S, $n_2$ is 0.

In Formula I, $D_1$ and $D_2$ represent an electron-donating group, and each is independently selected from any one of a C1 to C20 linear or branched alkyl group, a C1 to C20 alkoxyl group, a substituted or unsubstituted C6 to C40 aryl group, a substituted or unsubstituted C3 to C40 heteroaryl group, and a substituted or unsubstituted C6 to C40 arylamine group. Each of C1 to C20 represents a group having 1 to 20 carbons, such as C1, C2, C3, C4, C5, C6, C7, C8, C9, C10, C11, C12, C13, C14, C15, C16, C17, C18, C19 or C20.

In Formula I, $L_1$, $L_2$, $L_3$ and $L_4$ each is independently selected from any one of a single bond, a C1 to C20 linear or branched alkylene group, a substituted or unsubstituted C6 to C30 arylene group, and a substituted or unsubstituted C3 to C30 heteroarylene group.

In Formula I, $A_1$ and $A_2$ represent an electron-accepting group and each is independently selected from any one of a cyano group, a cyano-substituted C6 to C30 aromatic hydrocarbon group, a cyano-substituted C3 to C30 heteroaryl group, a substituted or unsubstituted C6 to C30 arylboron group, a substituted or unsubstituted C6 to C40 aryl keto group, a substituted or unsubstituted C4 to C40 heteroaryl keto group, a substituted or unsubstituted C6 to C30 arylsulfone group, and a substituted or unsubstituted C6 to C30 arylphosphonoxy group.

In Formula I, $R_1$ and $R_2$ each is independently selected from any one of halogen, a C1 to C30 linear or branched alkyl group, a C3 to C30 cycloalkyl group, a C3 to C20 heterocycloalkyl group, a substituted or unsubstituted C6 to C40 aryl group, and a substituted or unsubstituted C3 to C40 heteroaryl group.

when a substituent exists in the above groups, the substituent is selected from at least one of a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group or halogen.

Here $m_1$ and $m_2$ each is independently selected from an integer of 0 to 4, for example 0, 1, 2, 3 or 4.

The C1-C20 can be C2, C4, C6, C8, C10, C13, C15, C17 or C19.

The C6-C40 can be C7, C8, C10, C13, C15, C18, C20, C23, C25, C28, C30, C33, C35, C37 or C39.

The C3-C40 can be C4, C5, C6, C8, C10, C13, C15, C18, C20, C23, C25, C28, C30, C33, C35, C37 or C39.

The C6-C30 can be C7, C8, C9, C10, C13, C15, C18, C20, C23, C25, C28 or C29.

The C3-C30 can be C4, C5, C6, C8, C10, C13, C15, C18, C20, C23, C25, C27 or C29.

The C4-C40 can be C5, C6, C8, C10, C13, C15, C18, C20, C23, C25, C28, C30, C33, C35, C37 or C39.

The C1-C30 can be C2, C4, C5, C6, C8, C10, C13, C15, C18, C20, C23, C25, C27 or C29.

The C3-C20 can be C4, C5, C6, C8, C10, C13, C15, C17 or C19.

The C1 to C10 can be C1, C2, C3, C4, C5, C6, C7, C8, C9 or C10.

The C6-C20 can be C7, C8, C9, C10, C13, C15, C18 or C19.

The "electron donating group" means a group capable of increasing electron cloud density on a benzene ring, and the "electron accepting group" means a group capable of reducing electron cloud density on a benzene ring.

The second aspect of the present disclosure is to provide a display panel comprising an OLED device, the OLED device comprising an anode, a cathode, and at least one organic thin film layer between the anode and the cathode, the organic thin film layer comprises a light emitting layer, and any one or a combination of at least two of a hole transport layer, a hole injection layer, an electron blocking layer, a hole blocking layer, an electron transport layer, and an electron injection layer.

The light emitting layer includes the compound as described above, and the compound is used as any one of a host material, a doping material, and a co-doping material.

The third aspect of the present disclosure is to provide an electronic device comprising the display panel as described above.

Compared with the related technics, the present disclosure has the following beneficial effects:

Based on the molecular structure design, in the compound provided by the embodiment, from electron donor to acceptor (D-A) charge transfer effect forms through chemical bonds, and space charge transfer effect forms by using space distance design between an electron donor and an electron acceptor, thereby HOMO (Highest Occupied Molecular Orbital) and LUMO (Lowest Unoccupied Molecular Orbital) can form an effective separation in a molecule, reducing $\Delta E_{ST}$, enabling an energy level difference $\Delta E_{st} = E_{S1} - E_{T1} \leq 0.30$ eV, and realizing an efficient physical process of reverse intersystem crossing, so that the compound has typical TADF characteristics; the compound provided by the present disclosure can have two D-A light-emitting sub-units in one molecule, which have the property of a double emission nucleus, effectively improving oscillator strength and luminous efficiency; at the same time, bipolar characteristics of the compound are conducive to transporting electrons and holes. Therefore, the compound provided by the present disclosure is highly suitable as a material for a light-emitting layer of an OLED device, widens the light-emitting layer, and improves the luminous efficiency and working life of the OLED device.

DETAILED DESCRIPTION

Figure 1:
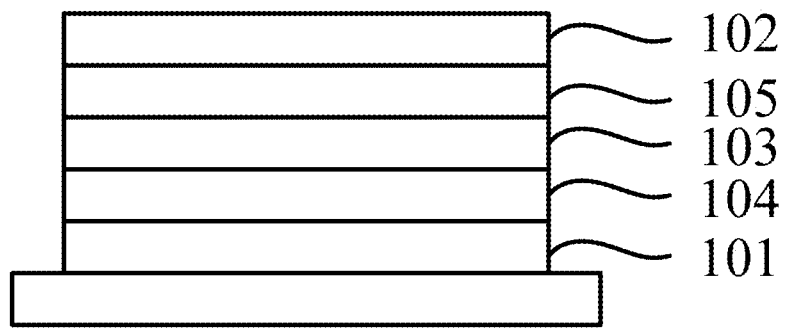
FIG. 1 is a schematic structural diagram of an OLED device provided by the present disclosure, where 101 is an anode, 102 is a cathode, 103 is a light emitting layer, 104 is a first organic thin film layer, and 105 is a second organic thin film layer.

The technical solutions of the present disclosure will be further described below by way of specific embodiments. It will be apparent to those skilled in the art that the embodiments are merely illustrations of the present disclosure and should not be construed as specific limitations to the present disclosure.

One aspect of the present disclosure is to provide a compound having a structure as shown in Formula I:

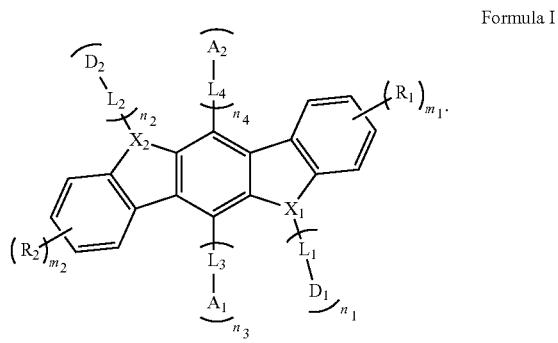

Formula I

In Formula I, $n_1$, $n_2$, $n_3$ and $n_4$ each is independently 0 or 1, and $n_3+n_4 \geq 1$, for example, $n_3+n_4=1$ or $n_3+n_4=2$.

In Formula I, $X_1$ and $X_2$ each is independently selected from O, S or N.

When $X_1$ is O or S, $n_1$ is 0.

When $X_2$ is O or S, $n_2$ is 0.

In Formula I, $D_1$ and $D_2$ represent an electron-donating group, and each is independently selected from any one of a C1 to C20 linear or branched alkyl group, a C1 to C20 alkoxyl group, a substituted or unsubstituted C6 to C40 aryl group, a substituted or unsubstituted C3 to C40 heteroaryl group, and a substituted or unsubstituted C6 to C40 arylamine group.

In Formula I, $L_1$, $L_2$, $L_3$ and $L_4$ each is independently selected from any one of a single bond, a C1 to C20 linear or branched alkylene group, a substituted or unsubstituted C6 to C30 arylene group, and a substituted or unsubstituted C3 to C30 heteroarylene group.

In Formula I, $A_1$ and $A_2$ represent an electron-accepting group and each is independently selected from any one of a cyano group, a cyano-substituted C6 to C30 aromatic hydrocarbon group, a cyano-substituted C3 to C30 heteroaryl group, a substituted or unsubstituted C6 to C30 arylboron group, a substituted or unsubstituted C6 to C40 aryl keto group, a substituted or unsubstituted C4 to C40 heteroaryl keto group, a substituted or unsubstituted C6 to C30 arylsulfone group, and a substituted or unsubstituted C6 to C30 arylphosphonoxy group.

In Formula I, $R_1$ and $R_2$ each is independently selected from any one of halogen, a C1 to C30 linear or branched alkyl group, a C3 to C30 cycloalkyl group, a C3 to C20 heterocycloalkyl group, a substituted or unsubstituted C6 to C40 aryl group, and a substituted or unsubstituted C3 to C40 heteroaryl group.

When a substituent exists in the above groups, the substituent is selected from at least one of a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen.

Here $m_1$ and $m_2$ each is independently selected from an integer of 0 to 4, for example 0, 1, 2, 3 or 4.

In the compound provided by the present disclosure, an electron acceptor group is connected to a benzene ring in the middle of a skeleton structure, and $X_1$ and $X_2$ each is independently selected from O, S or N. When $X_1$ and $X_2$ are both N, the compound has a skeleton structure of indolocarbazole, two N atoms of the skeleton structure are connected to an electron donor unit, so that in $D_1$-$L_1$-$X_1$-$L_3$-$A_1$ and $D_2$-$L_2$-$X_2$-$L_4$-$A_2$, not only D-A charge transfer effect can form through chemical bonds, at the same time since $D_1$ and $A_1$, $D_2$ and $A_2$ are relatively close in space, space charge transfer effect can be generated, thereby achieving effective separation of HOMO and LUMO in a molecule, reducing $\Delta E_{ST}$, realizing an efficient physical process of reverse intersystem crossing, so that the compound has typical TADF characteristics.

In the compound having the structure of formula I provided by the present disclosure, when $X_1$ and $X_2$ are both N, $n_3$ and $n_4$ are both 1, there are two D-A light-emitting sub-units in the same molecule, which has the property of dual emission nuclei and can effectively improve oscillator strength and luminous efficiency; moreover, the compound has bipolar characteristics, which can effectively transport electrons and holes, and is suitable to be used as host material of light-emitting layer of an OLED device, widen the light-emitting layer, and improve luminous efficiency and working life of the OLED device.

The C1-C20 can be C2, C4, C6, C8, C10, C13, C15, C17 or C19.

The C6-C40 can be C7, C8, C10, C13, C15, C18, C20, C23, C25, C28, C30, C33, C35, C37 or C39.

The C3-C40 can be C4, C5, C6, C8, C10, C13, C15, C18, C20, C23, C25, C28, C30, C33, C35, C37 or C39.

The C6-C30 can be C7, C8, C9, C10, C13, C15, C18, C20, C23, C25, C27 or C29.

The C3-C30 can be C4, C5, C6, C8, C10, C13, C15, C18, C20, C23, C25, C27 or C29.

The C4-C40 can be C5, C6, C8, C10, C13, C15, C18, C20, C23, C25, C28, C30, C33, C35, C37 or C39.

The C1-C30 can be C2, C4, C5, C6, C8, C10, C13, C15, C18, C20, C23, C25, C27 or C29.

The C3-C20 can be C4, C5, C6, C8, C10, C13, C15, C17 or C19.

The C1 to C10 can be C1, C2, C3, C4, C5, C6, C7, C8, C9 or C10.

The C6-C20 can be C7, C8, C9, C10, C13, C15, C17 or C19.

The "electron donating group" means a group capable of increasing electron cloud density on a benzene ring, and the "electron accepting group" means a group capable of reducing electron cloud density on a benzene ring.

In one embodiment, the cyano-substituted C6-C30 aromatic hydrocarbon group and the cyano-substituted C3-C30 heteroaryl group are selected from any one of the following groups:

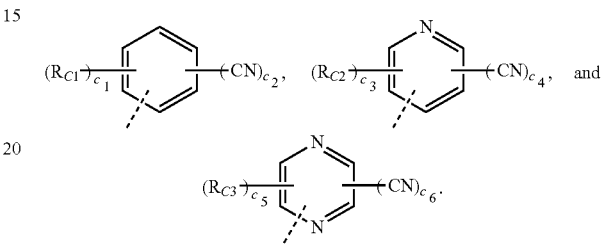

wherein, dotted line represents linking position of a group.

$R_{C1}$, $R_{C2}$ and $R_{C3}$ each is independently selected from at least one of an unsubstituted or halogenated C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

Here $c_1$ is an integer of 0 to 4, for example, 0, 1, 2, 3, or 4; $c_2$ is an integer of 1 to 3, for example, 1, 2 or 3; and $c_1+c_2\leq 5$.

Herein $c_3$ is an integer of 0 to 3, for example, 0, 1, 2, or 3; $c_4$ is an integer of 1 to 3, for example, 1, 2 or 3; and $c_3+c_4\leq 4$.

Also $c_5$ is an integer of 0 to 2, for example, 0, 1, or 2; $c_6$ is an integer of 1 to 3, for example, 1, 2 or 3; and $c_5+c_6\leq 3$.

In one embodiment, the cyano-substituted C6-C30 aromatic hydrocarbon group and the cyano-substituted C3-C30 heteroaryl group are selected from any one of the following groups:

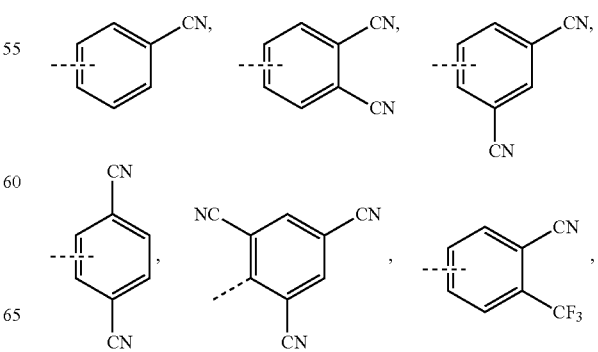

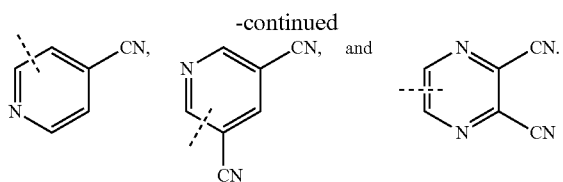

wherein, dotted line represents linking position of a group.

In the present disclosure, $A_1$ and $A_2$ represent electron-accepting groups. When the electron-accepting groups are the above-mentioned cyano substituents, they have a strong electron-withdrawing ability, can effectively suppress non-radiative transitions, and are conducive to construction of a compound having low $\Delta E_{ST}$, D-A type TADF characteristics with high radiative transition rate constant kr.

In one embodiment, the C6-C30 aryl boron group is selected from any one of the following groups:

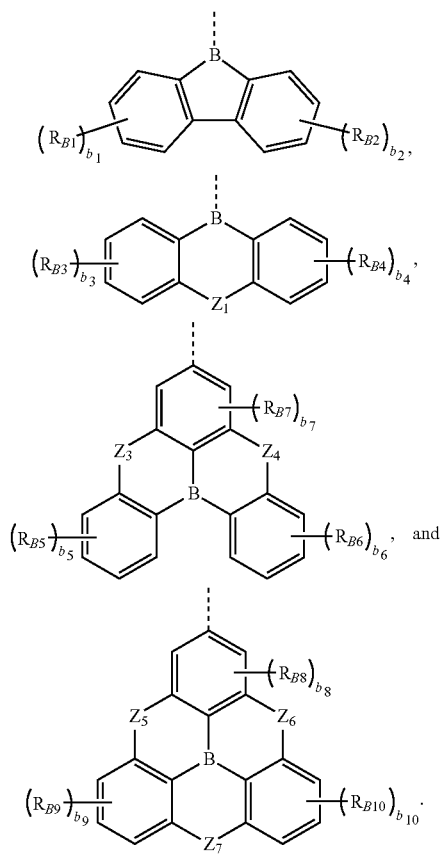

wherein, dotted line represents linking position of a group.

$R_{B1}$-$R_{B10}$ each is independently selected from any one of C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

$Z_1$-$Z_7$ each is independently selected from O, S, N—$R_{Z1}$ or B—$R_{Z2}$, $R_{Z1}$ and $R_{Z1}$ each is independently selected from any one of hydrogen, C6 to C40 (for example, C7, C8, C10, C13, C15, C18, C20, C23, C25, C28, C30, C33, C35, C37 or C39.) aryl group, C1 to C10 (for example, C2, C3, C4, C5, C6, C7, C8 or C9) linear or branched alkyl group, C1 to C20 (for example, C2, C4, C6, C8, C10, C13, C15, C17 or C19.) alkoxyl group, C3 to C20 (for example, C4, C6, C7, C9, C10, C12, C14, C15, C17 or C19.) cycloalkyl group, C3 to C20 (for example, C4, C6, C7, C9, C10, C12, C14, C15, C17 or C19.) heterocyclic alkyl group, and C3 to C40 (for example, C4, C5, C6, C8, C10, C13, C15, C18, C20, C23, C25, C28, C30, C33, C35, C37 or C39.) heteroaryl group.

Here $b_1$-$b_6$ each is independently an integer of 0 to 4, for example 0, 1, 2, 3 or 4.

Here $b_7$ and $b_8$ each is independently an integer of 0 to 2, for example 0, 1, or 2.

Here $b_9$ and $b_{10}$ each is independently an integer of 0 to 3, for example 0, 1, 2, or 3.

In one embodiment, the C6-C30 aryl boron group is selected from any one of the following groups:

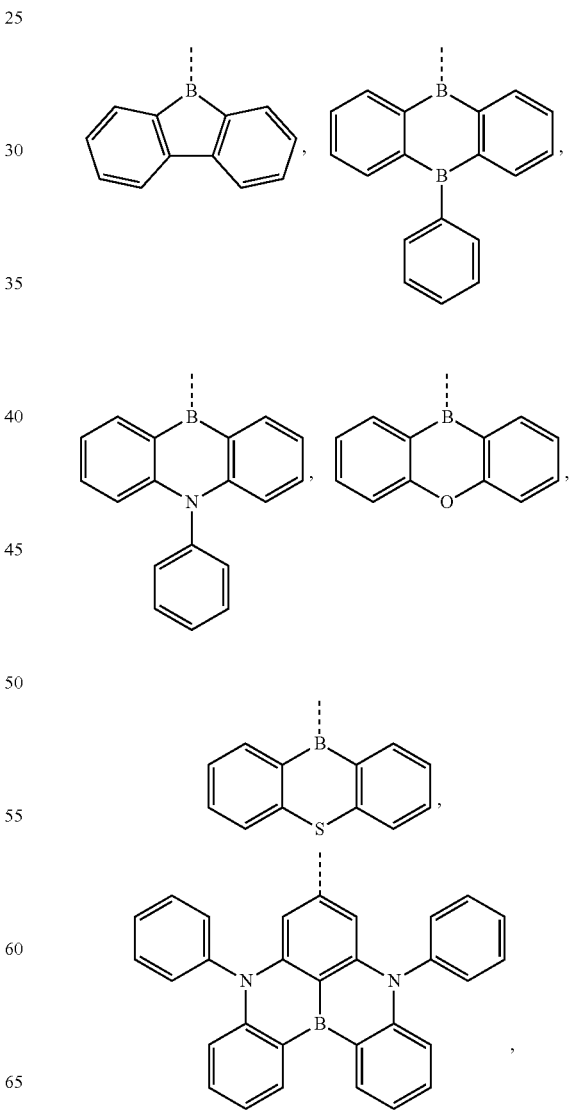

-continued

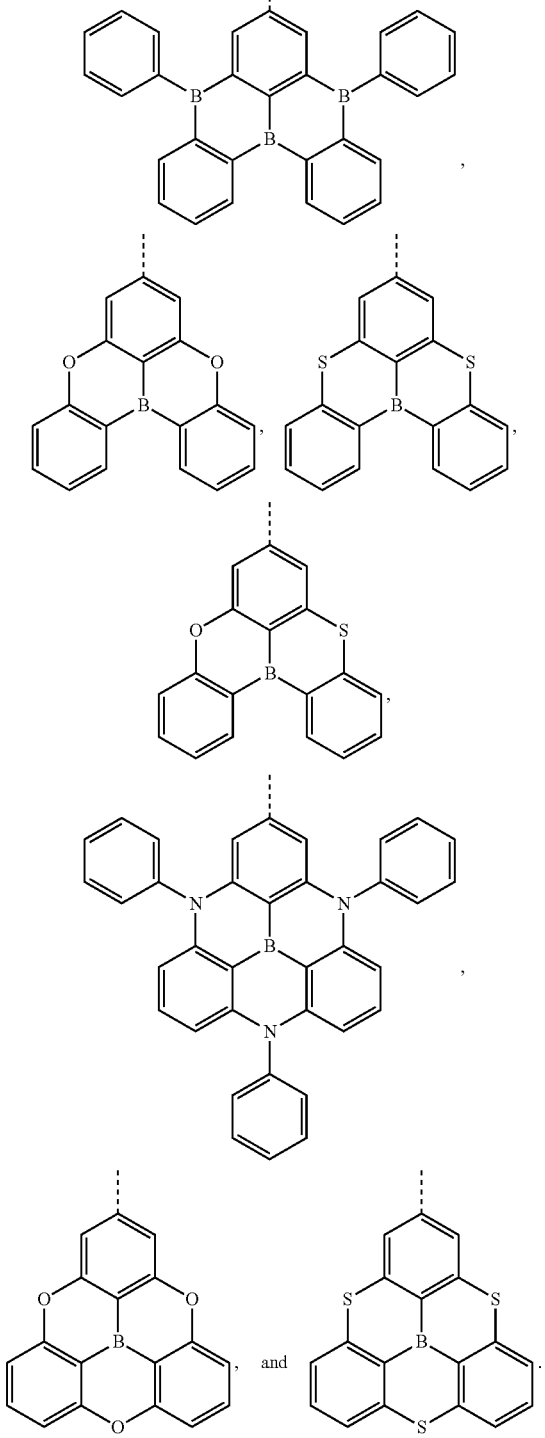

Wherein, dotted line represents linking position of a group.

In the present disclosure, $A_1$ and $A_2$ represent electron accepting groups. When the electron accepting group is the above-mentioned aryl boron group, the aryl boron group containing a six-membered ring has more advantages of resonant structure than that containing a five-membered ring.

In one embodiment, the C6-C40 aryl keto group, and the substituted or unsubstituted C4-C40 heteroaryl keto group are selected from any one of the following groups:

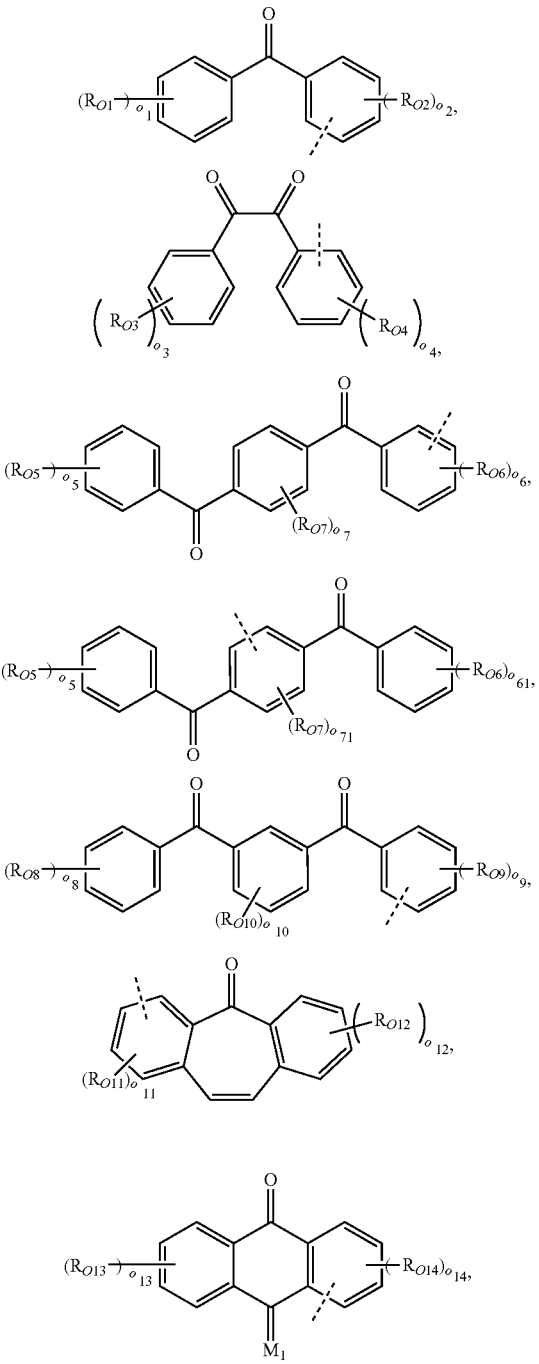

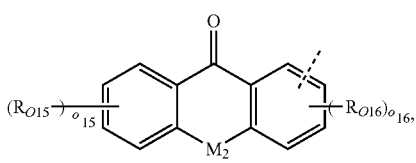

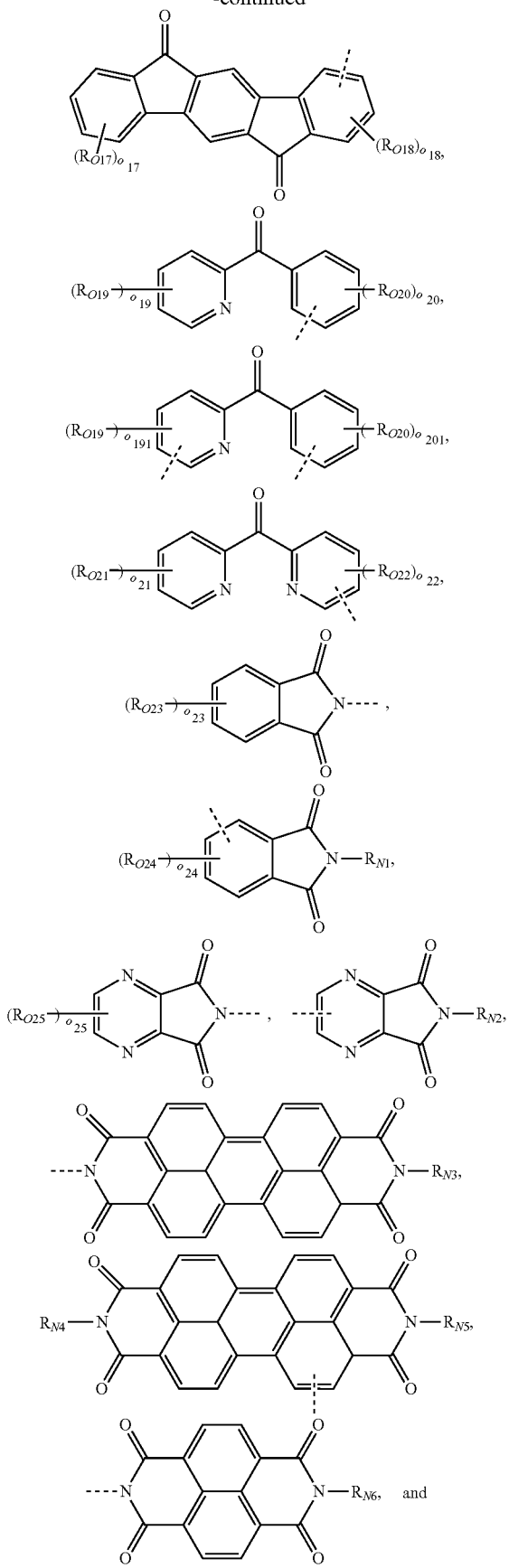

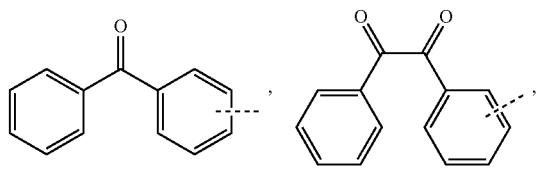

wherein, dotted line represents linking position of a group.

$R_{O1}$-$R_{O26}$ each is independently selected from any one of C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

Here $M_1$ is O or S.

$M_2$ is selected from O, S or $R_{M1}$—C—$R_{M2}$, and $R_{M1}$ and $R_{M2}$ each is independently selected from any one of hydrogen, C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

$R_{N1}$-$R_{N6}$ each is independently selected from any one of C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

Here $o_1$, $o_3$, $o_5$, $o_{61}$, $o_8$, and $o_{201}$ each is independently an integer of 0 to 5, for example 0, 1, 2, 3, 4 or 5.

Here $o_2$, $o_4$, $o_6$, $o_7$, $o_9$, $o_{10}$, $o_{12}$, $o_{13}$, $o_{15}$, $o_{17}$, $o_{19}$, $o_{20}$, $o_{21}$, and $o_{23}$ each is independently an integer of 0 to 4, for example 0, 1, 2, 3 or 4.

Here $o_{71}$, $o_{11}$, $o_{14}$, $o_{16}$, $o_{18}$, $o_{191}$, $o_{22}$, $o_{24}$, $o_{26}$, and $o_{27}$ each is independently an integer of 0 to 3, for example 0, 1, 2 or 3.

Here $o_{25}$ is an integer of 0 to 2, for example 0, 1 or 2.

In one embodiment, the C6-C40 aryl keto group, and the substituted or unsubstituted C4-C40 heteroaryl keto group are selected from any one of the following groups:

-continued

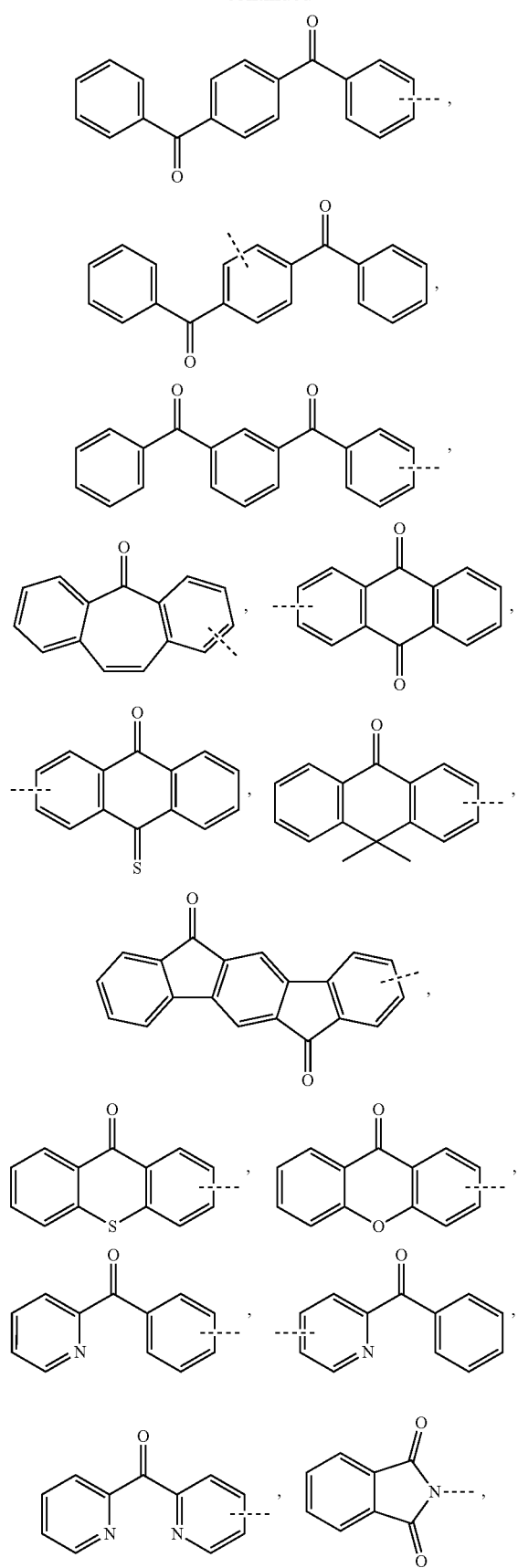

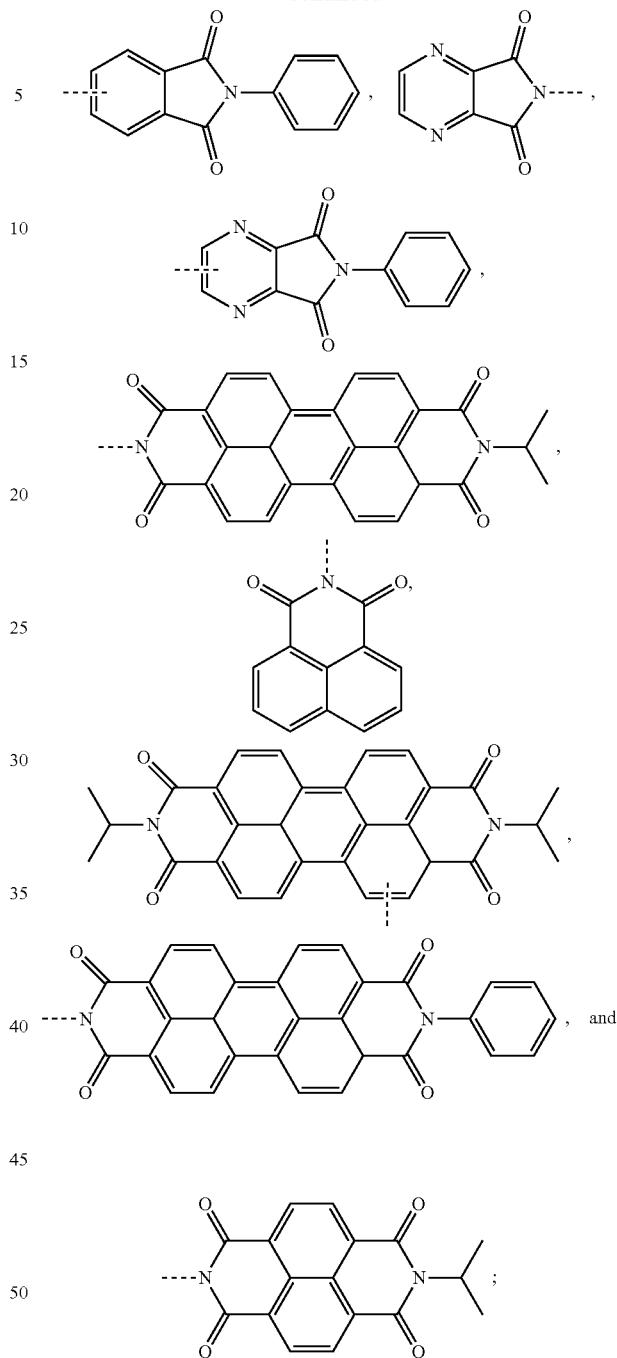

wherein, dotted line represents linking position of a group.

According to the present disclosure, $A_1$ and $A_2$ represent electron accepting groups. When the electron accepting group is the above-mentioned aryl keto group, the substituent contains an electron-deficient carbonyl group which has large twist angle with benzene ring when used as electron acceptor, thus it is a highly efficient acceptor unit (kISC=$10^{11}$ s$^{-1}$) for intersystem crossing, which is very suitable for constructing D-A-type TADF blue light molecule as electron acceptor.

In one embodiment, the C6-C30 aryl sulfone group is selected from any one of the following groups:

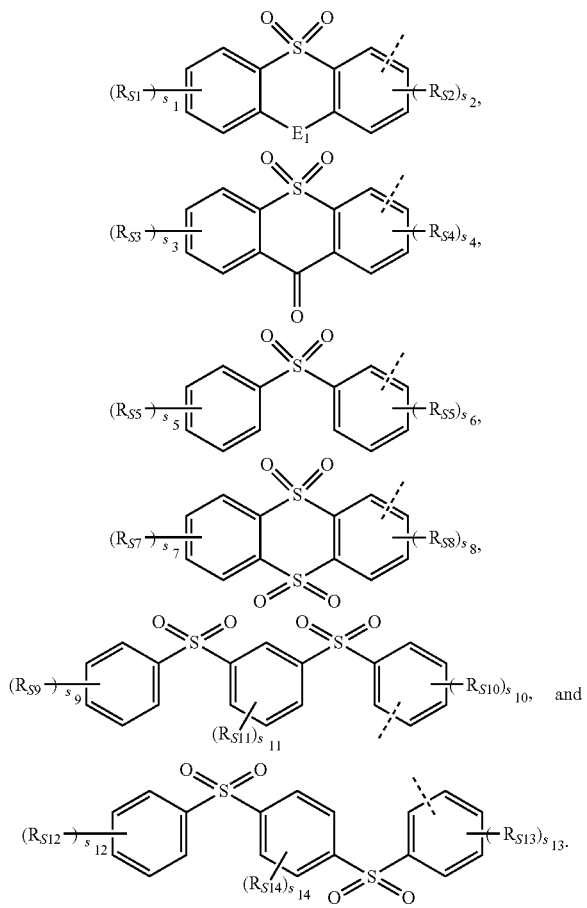

wherein, dotted line represents linking position of a group.

Here $R_{S1}$-$R_{S14}$ each is independently selected from any one of C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

Here $E_1$ is selected from O, S or $R_{E1}$—C—$R_{E2}$, and $R_{E1}$ and $R_{E2}$ each is independently selected from any one of hydrogen, C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

Herein $s_1$, $s_3$, $s_6$, $s_7$, $s_{10}$, $s_{11}$, $s_{13}$, and $s_{14}$ each is independently an integer of 0 to 4, for example, 0, 1, 2, 3 or 4.

Here $s_2$, $s_4$, and $s_8$ each is independently an integer of 0 to 3, for example, 0, 1, 2 or 3.

Here again $s_5$, $s_9$, and $s_{12}$ each is independently an integer of 0 to 5, for example, 0, 1, 2, 3, 4 or 5.

In one embodiment, the C6-C30 arylphosphonoxy group is selected from any one of the following groups:

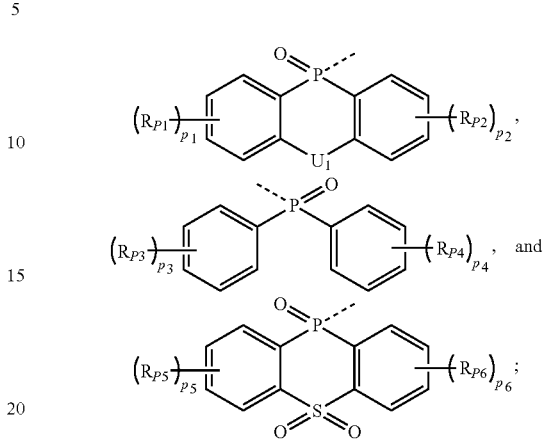

wherein, dotted line represents linking position of a group.

Here $R_{P1}$-$R_{P6}$ each is independently selected from any one of C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

Here $U_1$ is selected from O, S, N—$R_{U1}$, B—$R_{U2}$ or $R_{U3}$—C—$R_{U4}$, and $R_{U1}$-$R_{U4}$ each is independently selected from any one of hydrogen, C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

$p_1$, $p_2$, $p_5$, and $p_6$ each is independently an integer of 0 to 4, for example, 0, 1, 2, 3 or 4.

Here $p_3$ and $p_4$ each is independently selected from an integer of 0 to 5, for example 0, 1, 2, 3, 4 or 5.

In one embodiment, $X_1$ and $X_2$ are both N, and $n_1$ and $n_2$ are both 1.

In one embodiment, $D_1$ and $D_2$ each is independently selected from any one of the following groups:

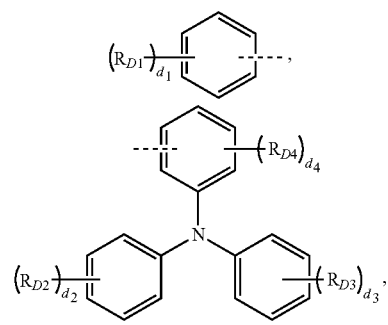

-continued

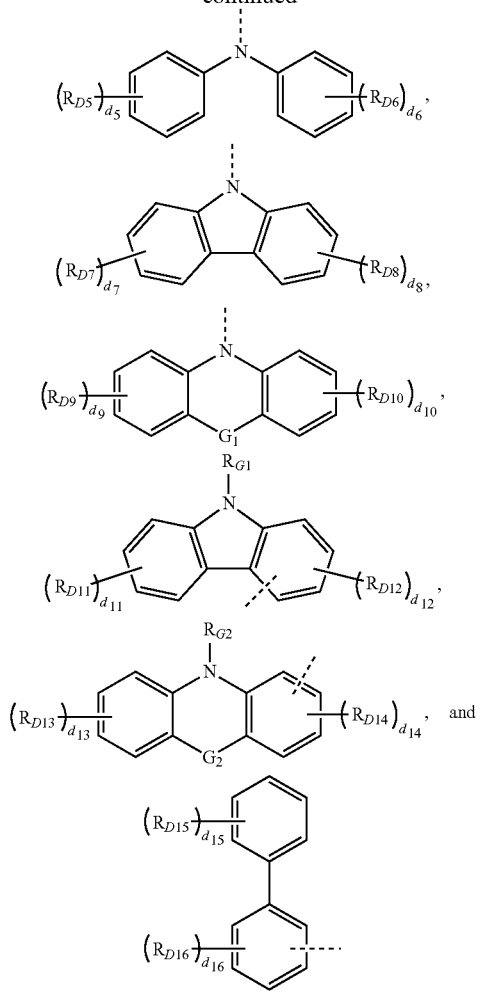

wherein, dotted line represents linking position of a group.

Here $R_{D1}$-$R_{D16}$ each is independently selected from any one of C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group or halogen.

Here $G_1$ and $G_2$ each is independently selected from O, S, N—$R_{G3}$ or $R_{G4}$—C—$R_{G5}$.

Here $R_{G1}$-$R_{G5}$ each is independently selected from any one of C1-C10 (for example, C2, C3, C4, C5, C6, C7, C8 or C9) linear or branched alkyl group, C6-C20 (for example, C7, C9, C10, C12, C14, C15, C17 or C19.) aryl group, C6-C20 (for example, C7, C9, C10, C12, C14, C15, C17 or C19.) heteroaryl group, C1-C10 (for example, C2, C3, C4, C5, C6, C7, C8 or C9) alkoxyl group, C6-C20 (for example, C7, C9, C10, C12, C14, C15, C17 or C19.) arylamine group, C3-C20 (for example, C4, C6, C8, C10, C12, C14, C16 or C18.) cycloalkyl group, and halogen.

Here $d_1$, $d_2$, $d_3$, $d_5$, $d_6$, and $d_{15}$ each is independently an integer of 0 to 5, for example, 0, 1, 2, 3, 4 or 5.

Here $d_4$, $d_7$, $d_8$, $d_9$, $d_{10}$, $d_{11}$, $d_{13}$, and $d_{16}$ are each independently an integer of 0 to 4, for example, 0, 1, 2, 3 or 4.

Here $d_{12}$ and $d_{14}$ each is independently an integer of 0 to 3, for example, 0, 1, 2 or 3.

In one embodiment, $D_1$ and $D_2$ each is independently selected from any one of the following groups:

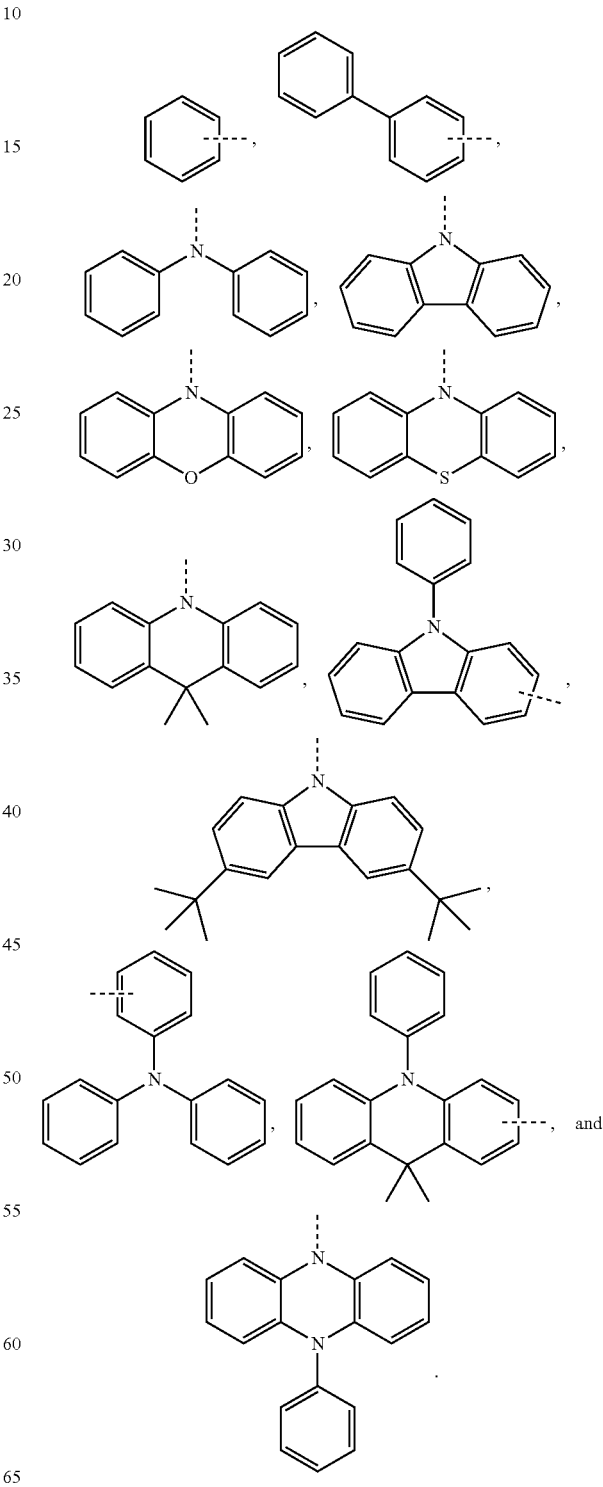

Wherein, dotted line represents linking position of a group.

Here $D_1$ and $D_2$ described in the present disclosure are electron-donating groups, which form a D-A charge transfer effect with backbone structure and electron acceptors $A_1$ and $A_2$ through chemical bonds, reducing the overlap between HOMO and LUMO, so that the HOMO and LUMO energy levels can be effectively separated and an energy level difference $\Delta E_{ST}$ between the triplet and the singlet is reduced, achieving efficient reverse crossing of energy from the triplet to the singlet, endowing the compounds of the present disclosure with typical TADF characteristics, and achieving high luminous efficiency.

In one embodiment, $m_1$ and $m_2$ are both 0.

In one embodiment, $L_1$, $L_2$, $L_3$ and $L_4$ each is independently selected from a single bond or a C6-C20 (for example, C7, C9, C10, C12, C14, C15, C17 or C19.) phenylene group.

In the compounds of the present invention, when $X_1$ and $X_2$ are both N, $n_3$ and $n_4$ are both 1, $L_1$, $L_2$, $L_3$, $L_4$ and the skeleton structure of indolocarbazole together with an electron donor and an electron acceptor form two light-emitting subunits $D_1$-$L_1$-$X_1$-$L_3$-$A_1$ and $D_2$-$L_2$-$X_2$-$L_4$-$A_2$, so that the molecular structure has a large rigid distortion, HOMO and LUMO energy levels are effectively separated, and an energy level difference between the triplet state and the singlet states is reduced. Moreover, the compound has properties of dual emission nuclei and bipolar characteristics, which can improve oscillator strength and luminous efficiency, effectively transport electrons and holes, and in turn improve luminous performance of OLED devices.

In one embodiment, the compound is selected from any one of the following compounds M1 to M134:

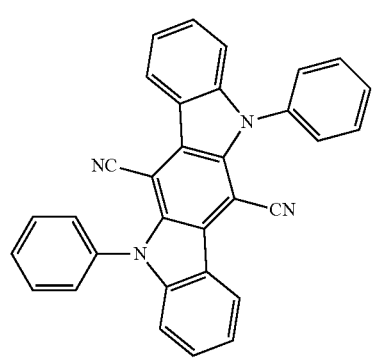

M1

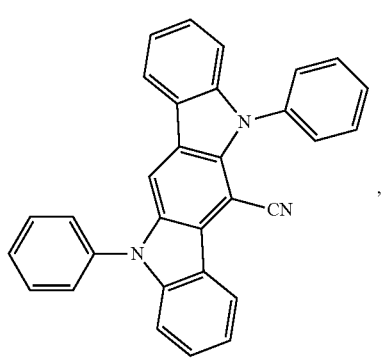

M2

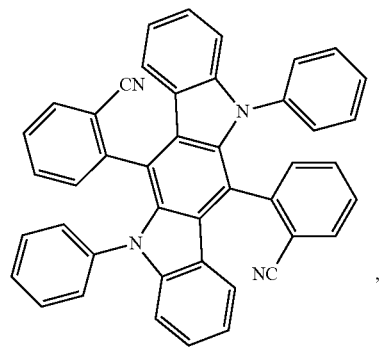

M3

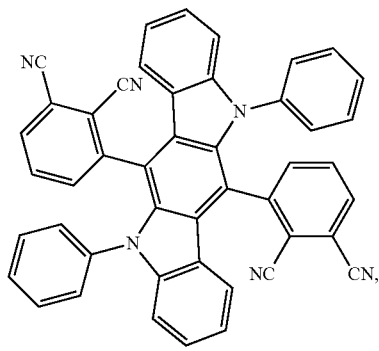

M4

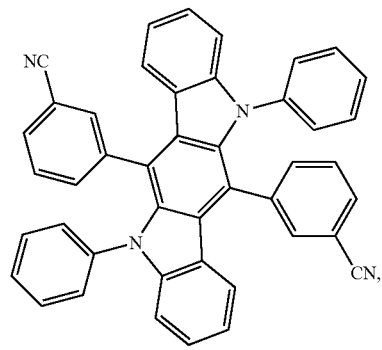

M5

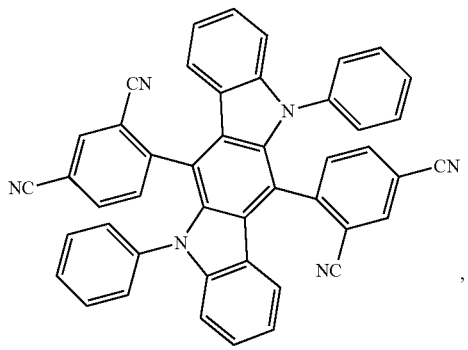

M6

-continued
| M7 | M8 |
|---|---|
| 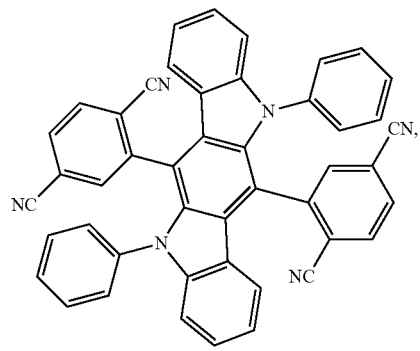 | 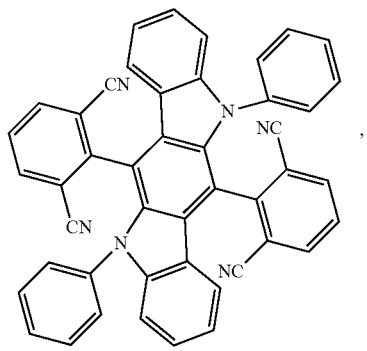 |
| M9 | M10 |
| 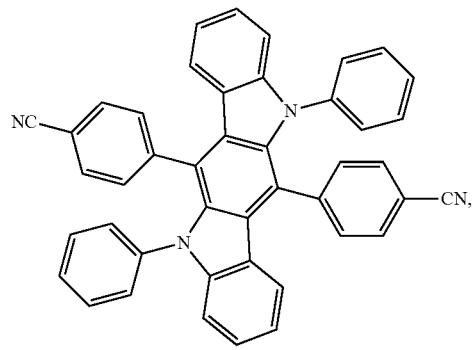 | 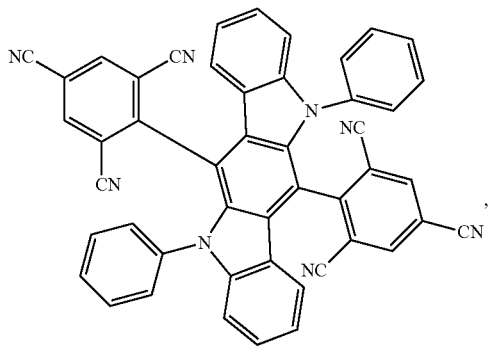 |
| M11 | M12 |
| 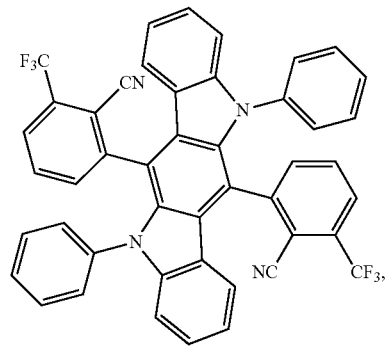 | 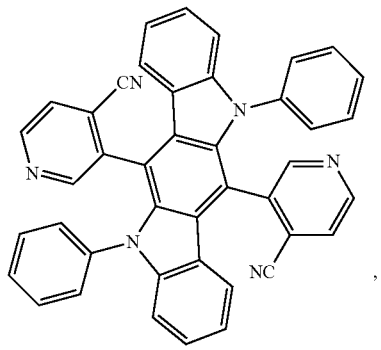 |
| M13 | M14 |
| 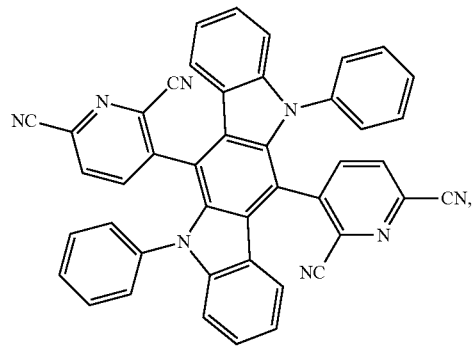 | 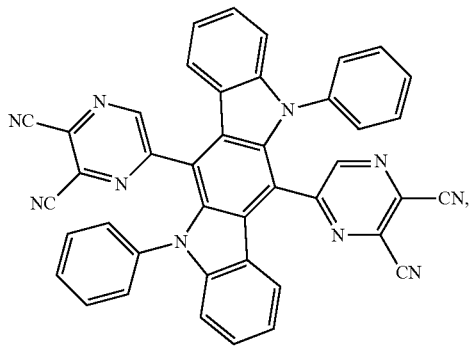 |

-continued
M15
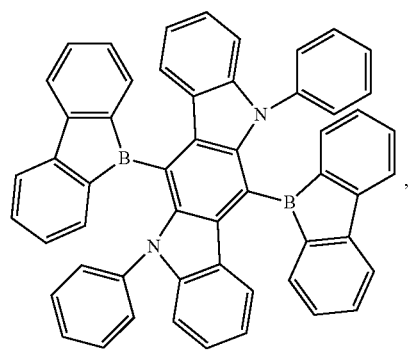,
M16
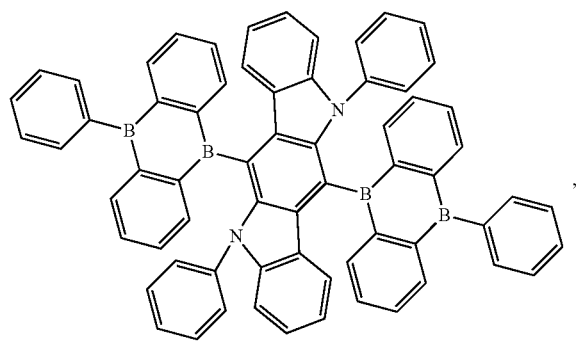,
M17
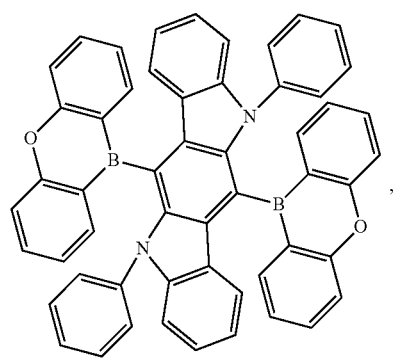,
M18
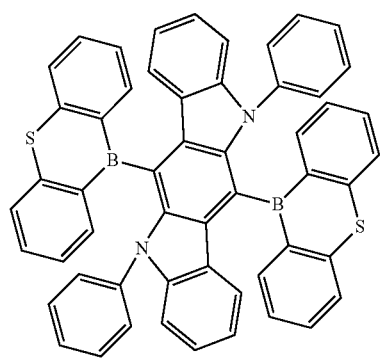,
M19
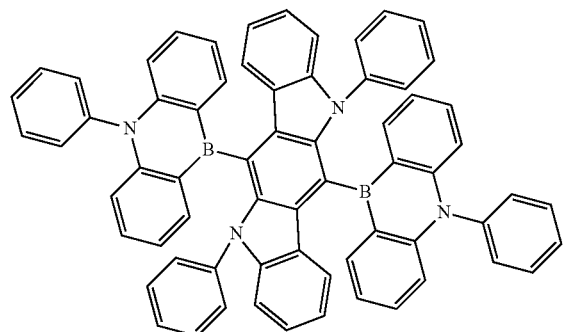,
M20
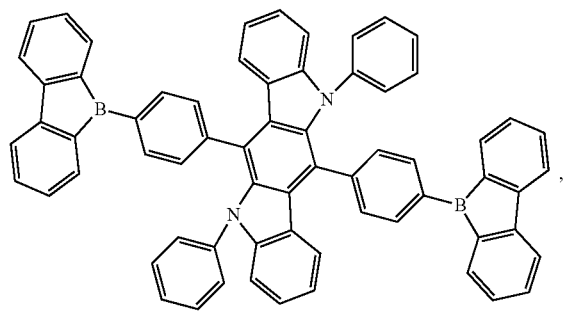,
M21
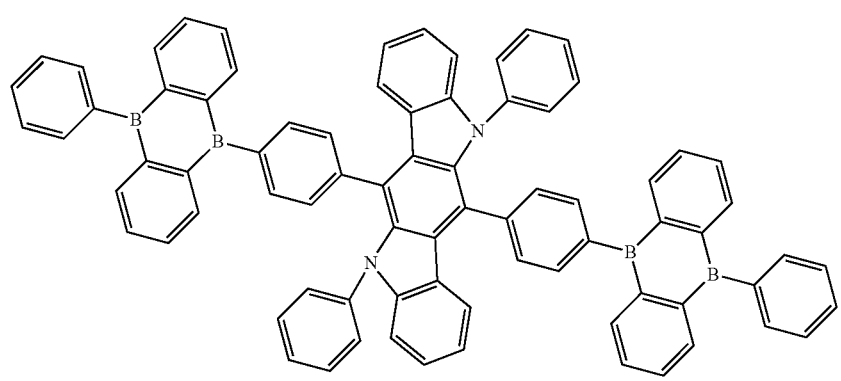, -continued
M26
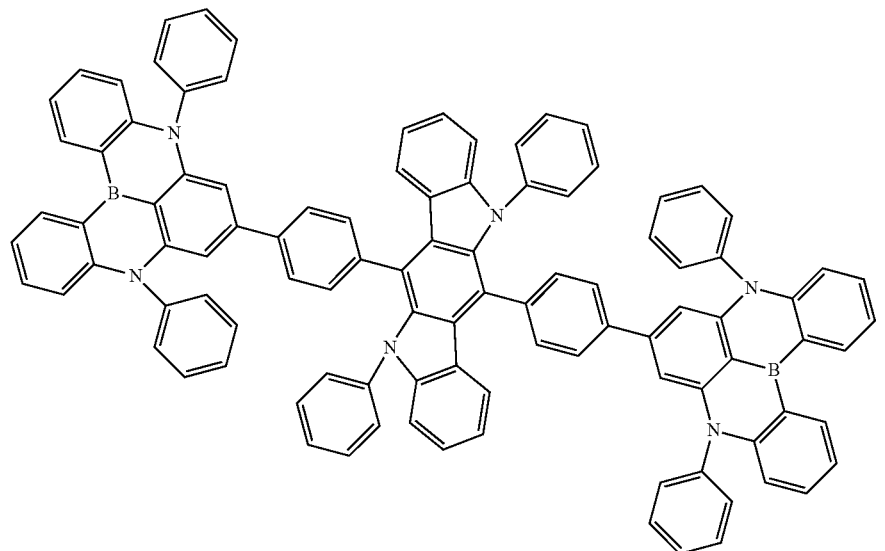
M27
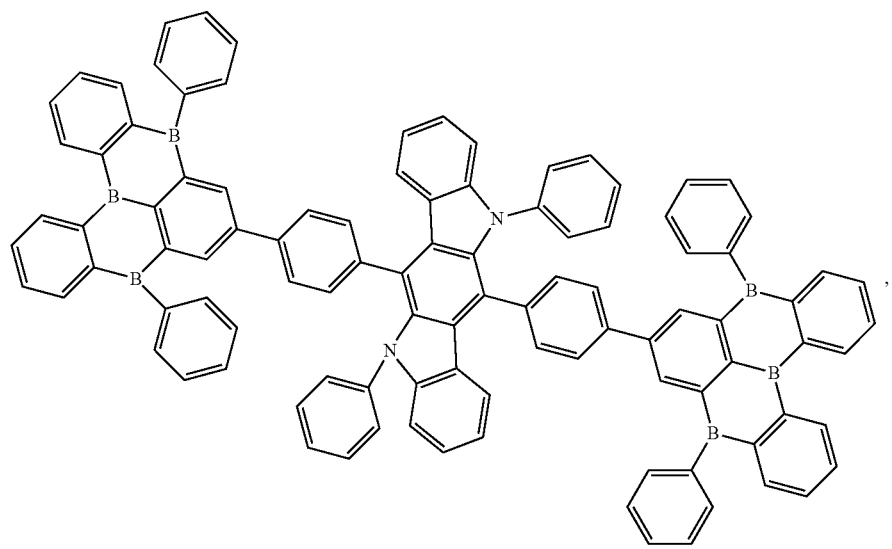
M28
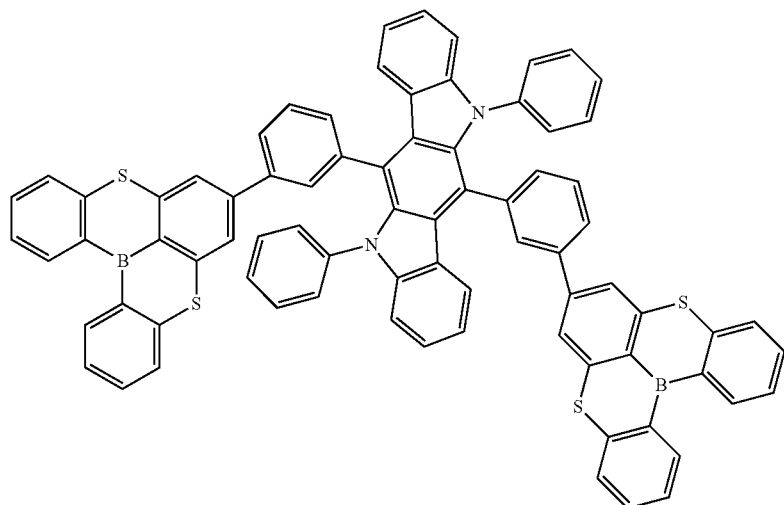

M29
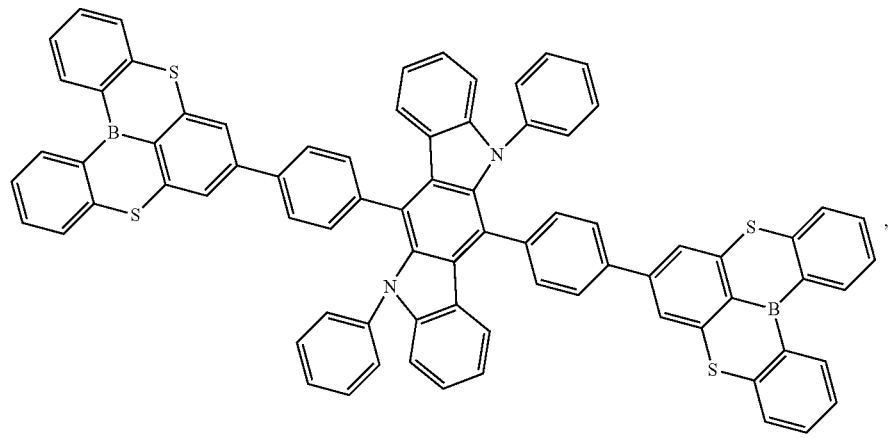
M30
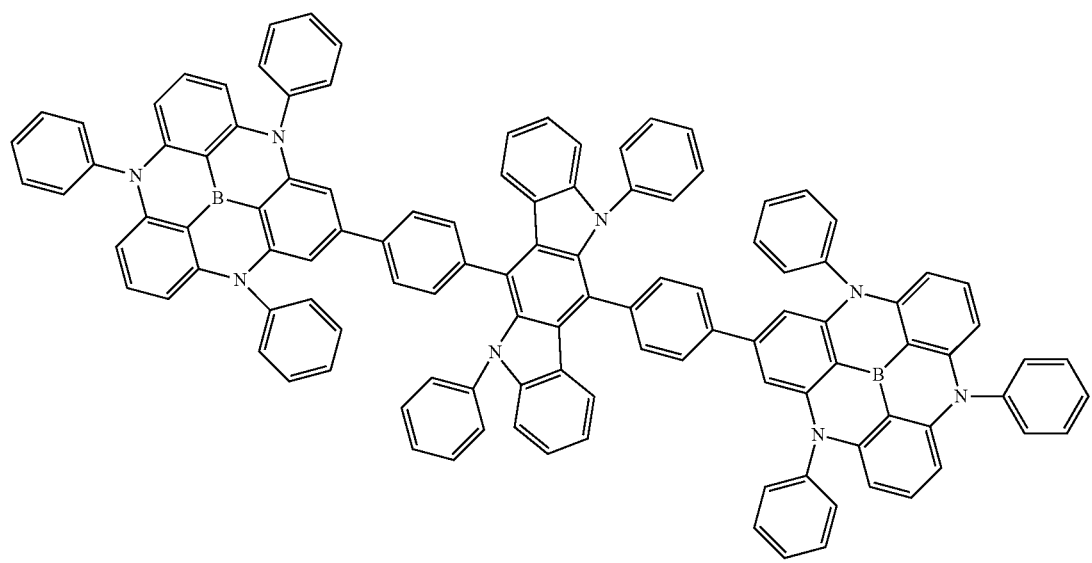
M31
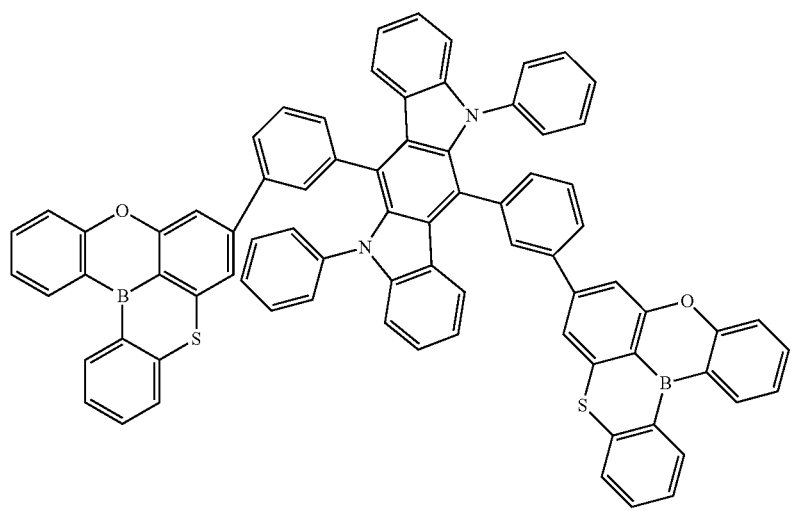

-continued
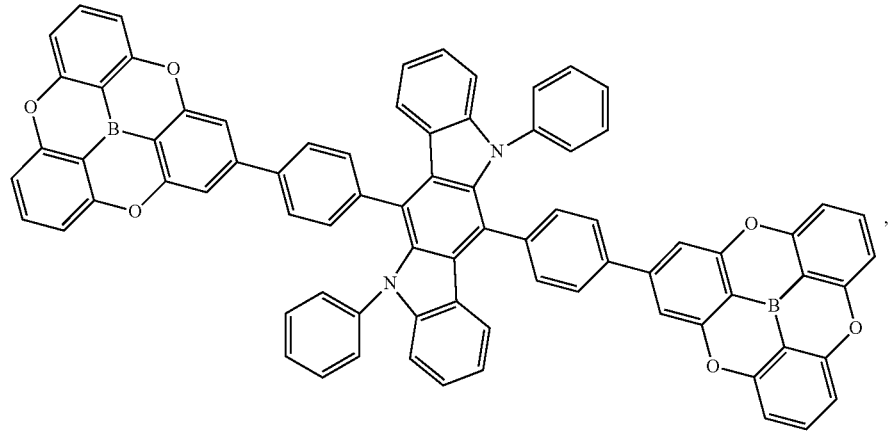
M32
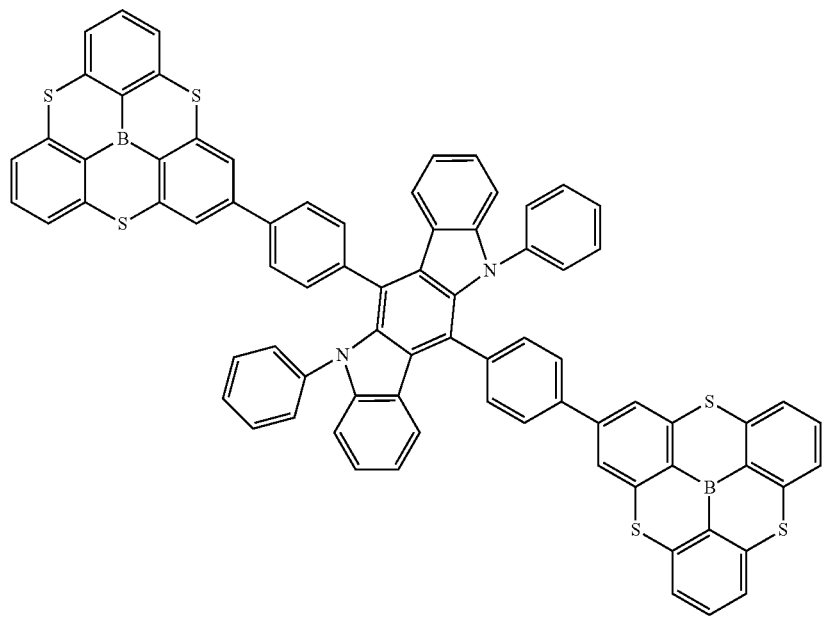
M33
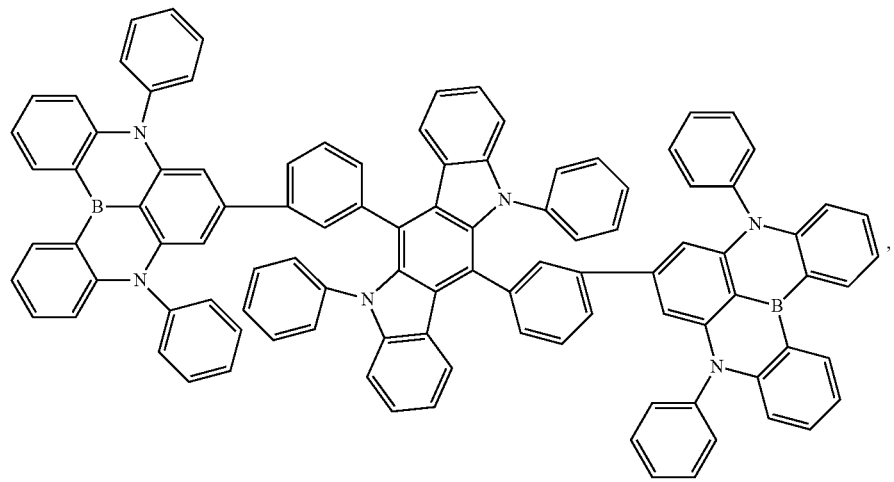
M34

-continued
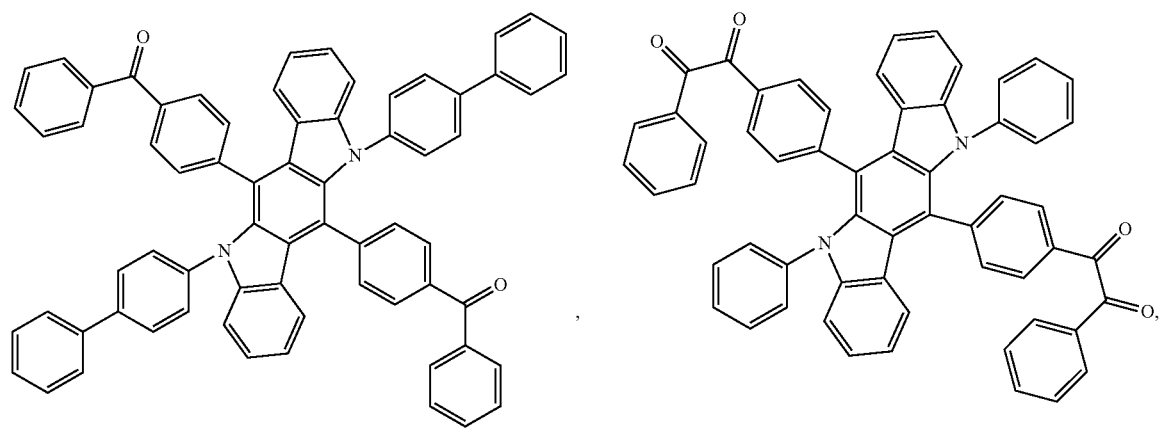
M35
M36
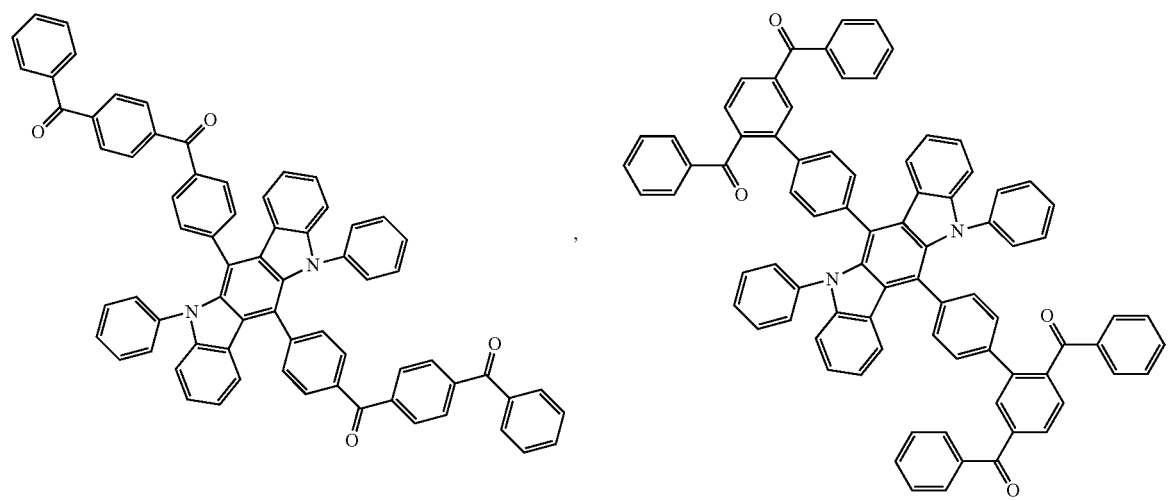
M37
M38
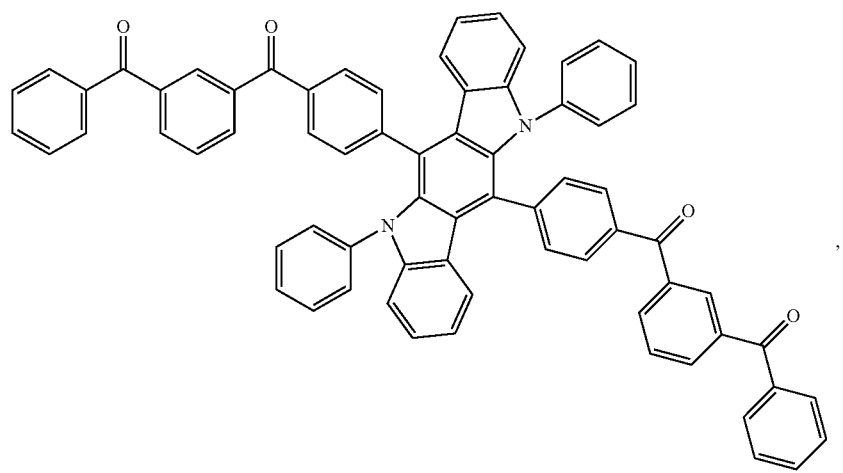
M39

-continued
M40
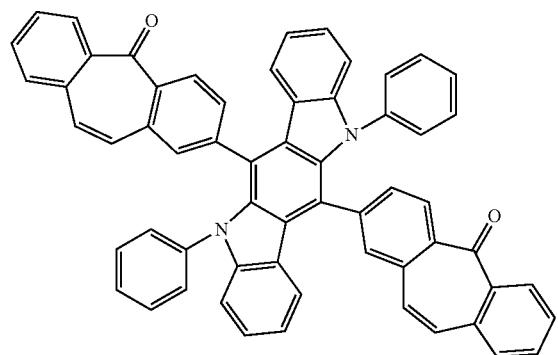
M41
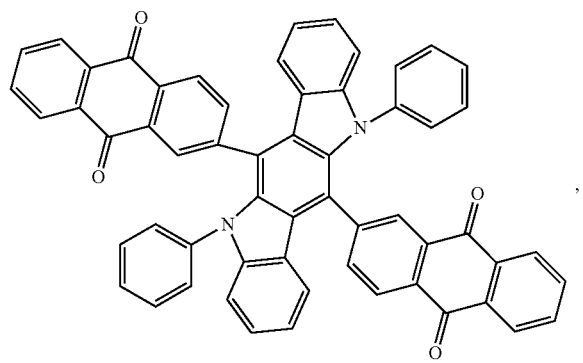
M42
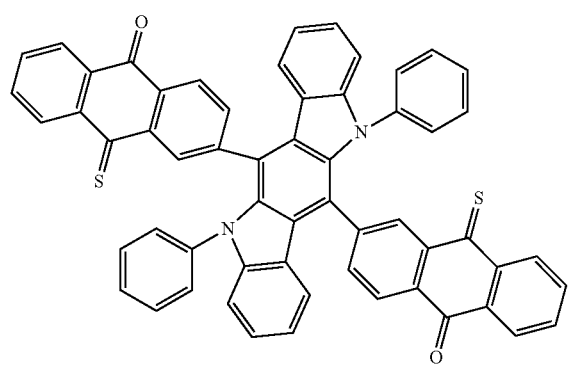
M43
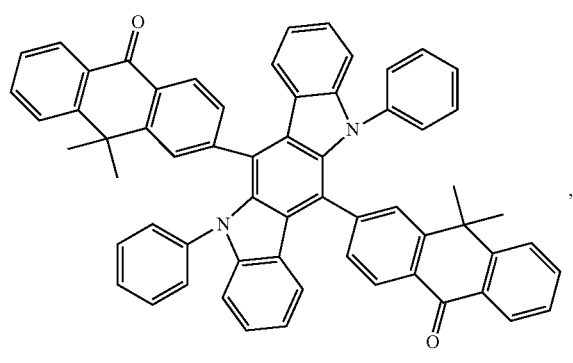
M44
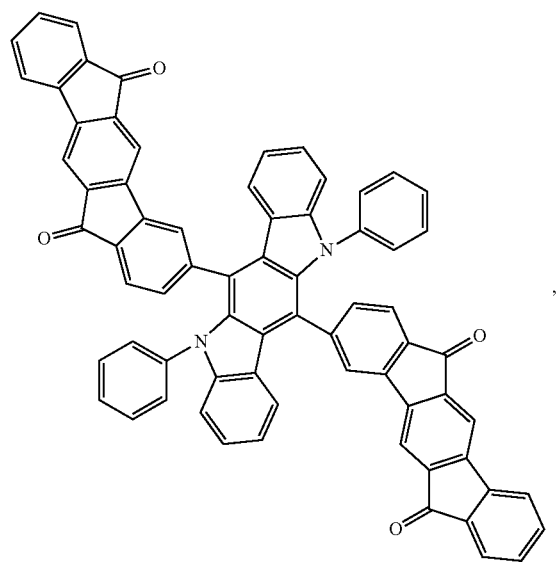
M45
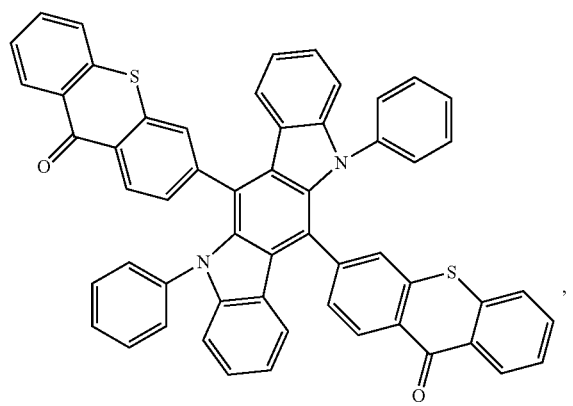

-continued
M46
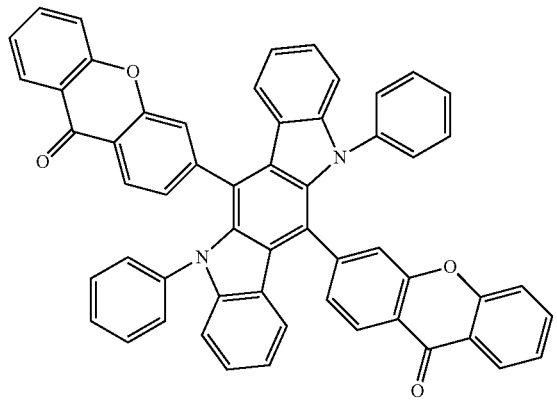,
M47
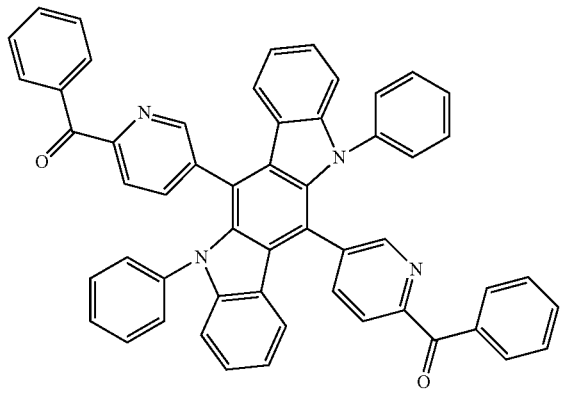,
M48
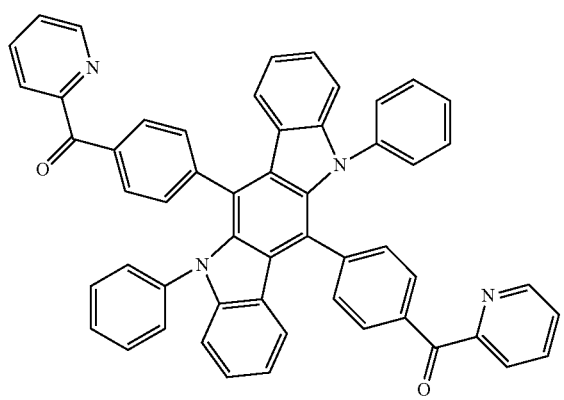,
M49
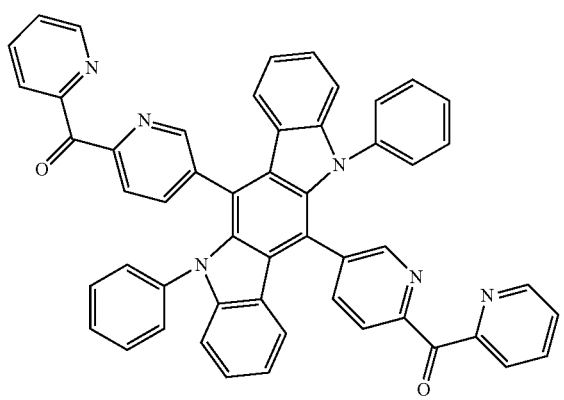,
M50
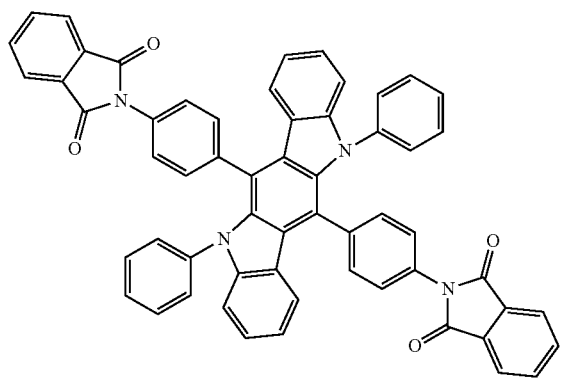,
M51
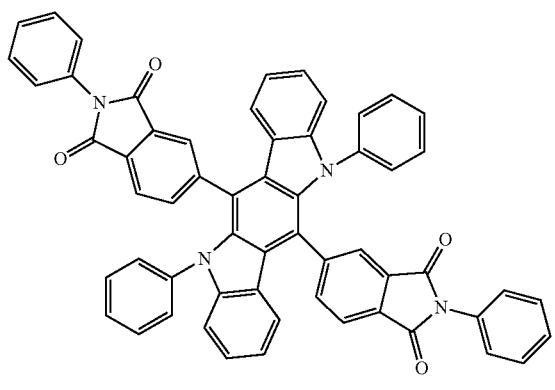,
M52
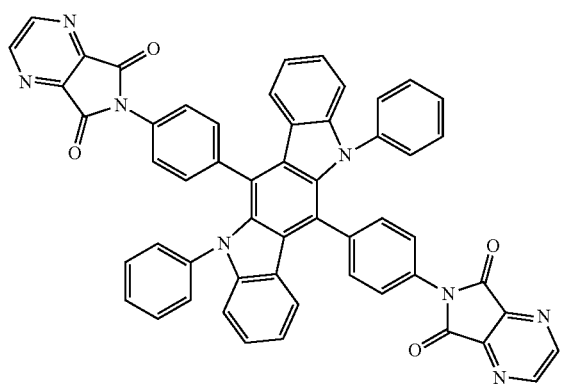,
M53
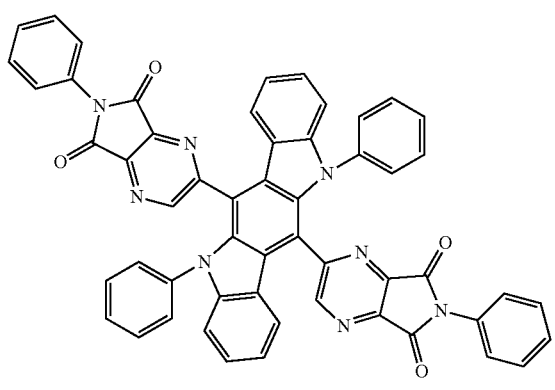, M54
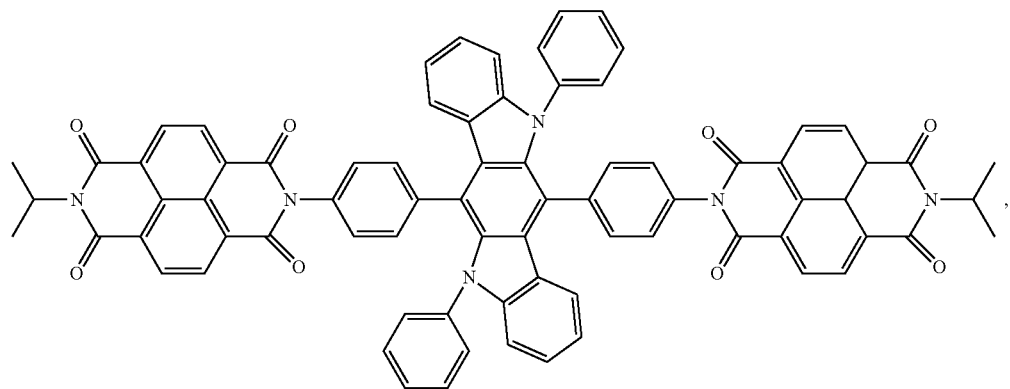
M55
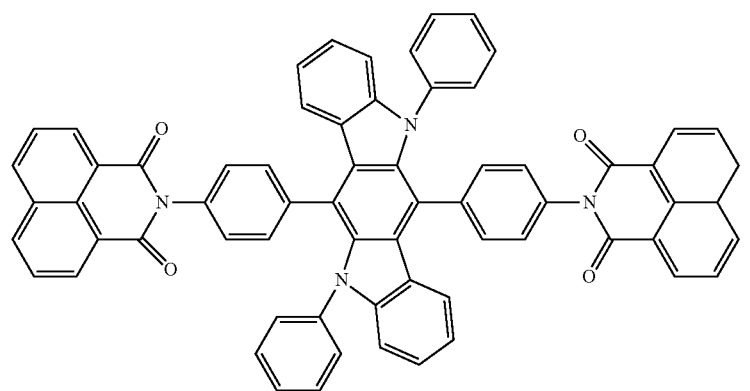
M56
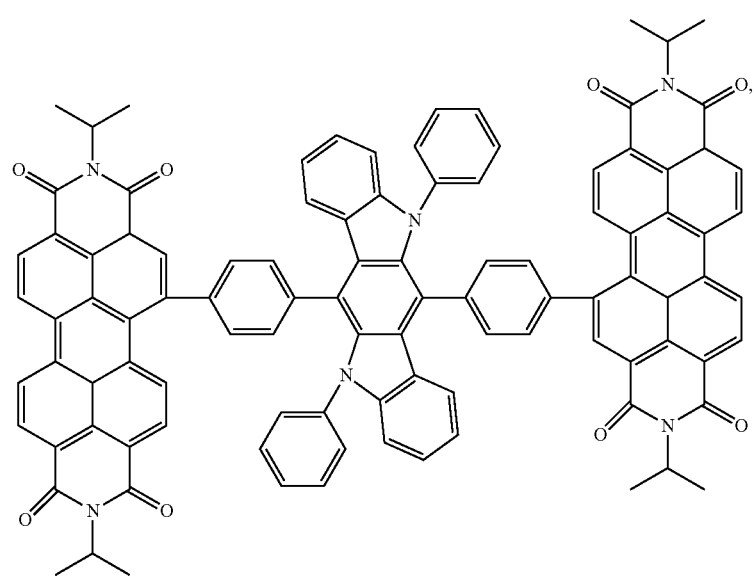

-continued
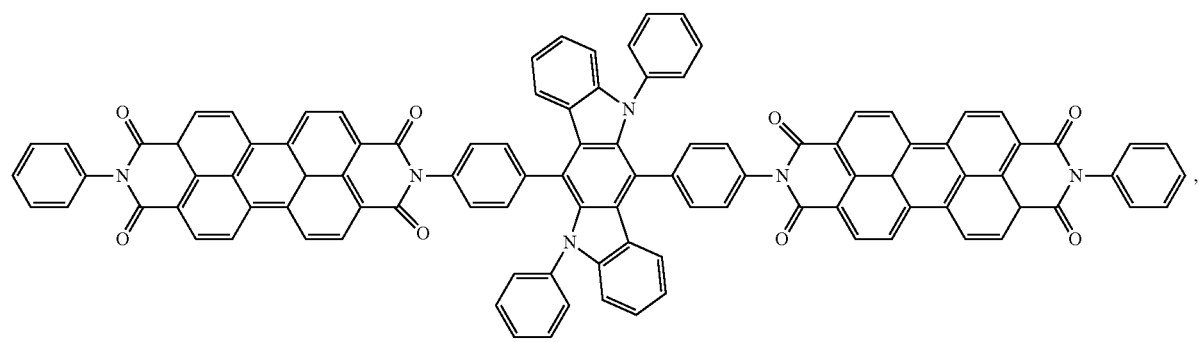
M57
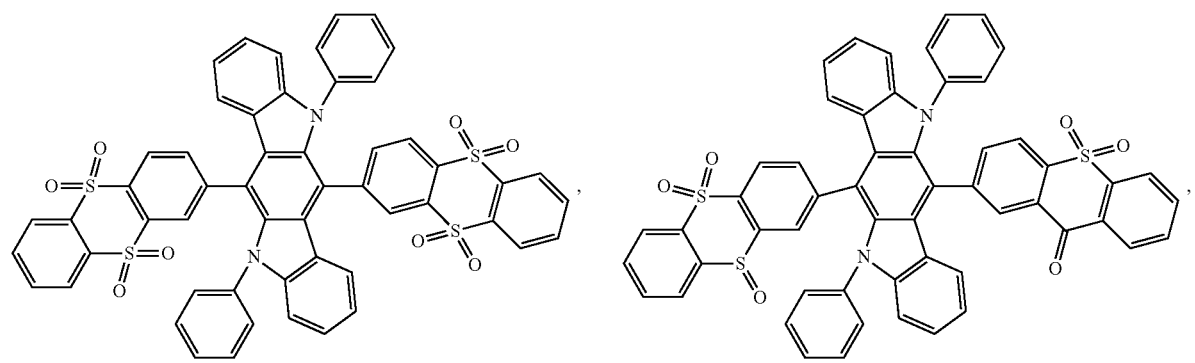
M58    M59
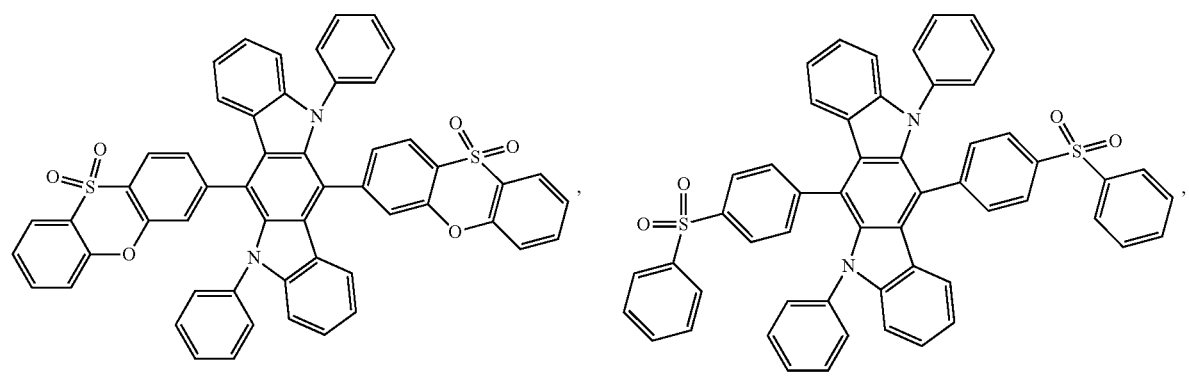
M60    M61

-continued
M62
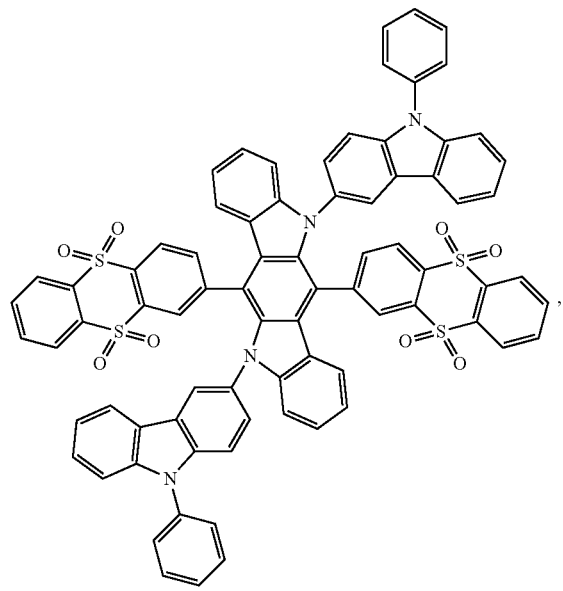
M63
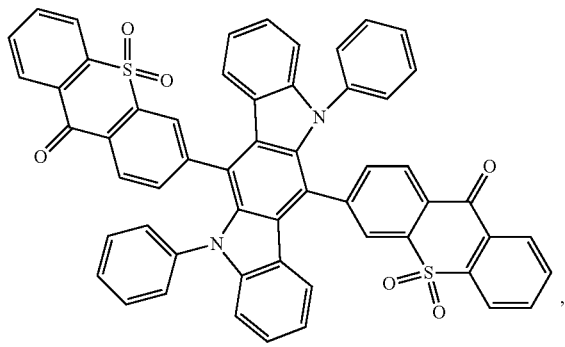
M64
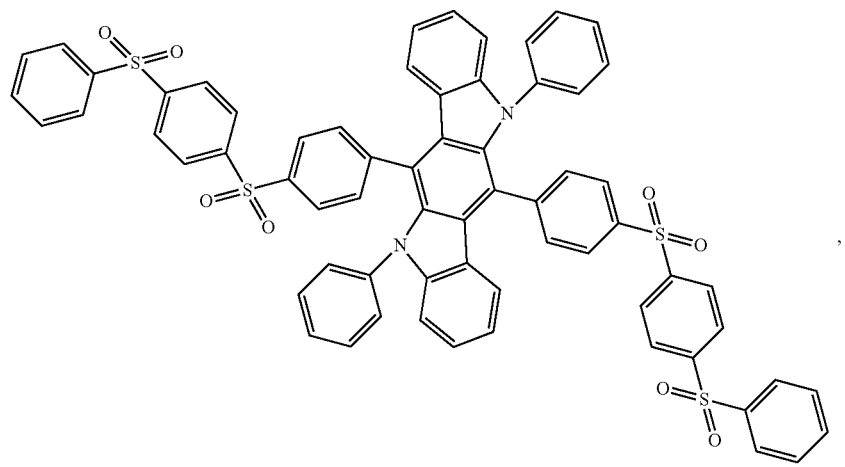
M65
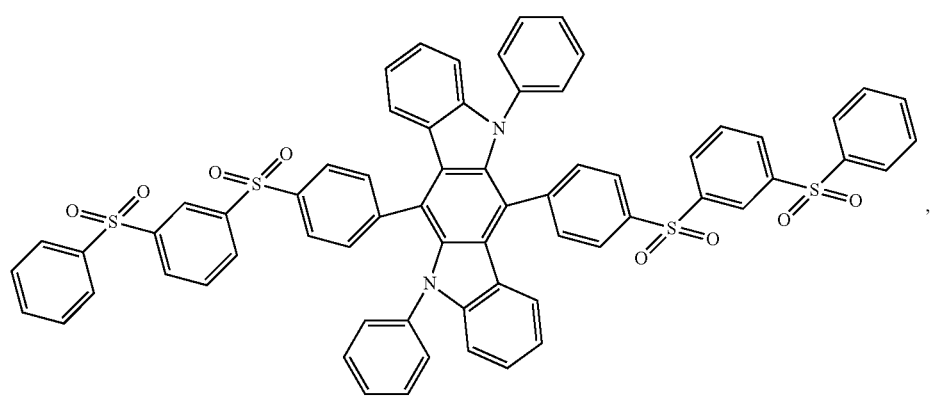

-continued
M66
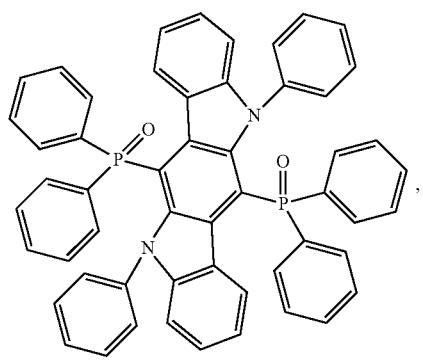
M67
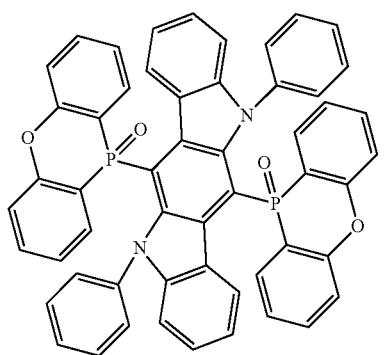
M68
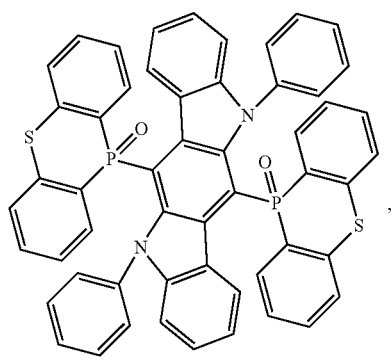
M69
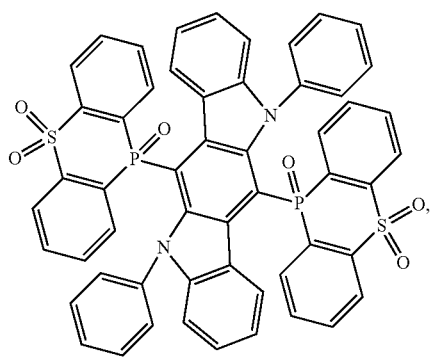
M70
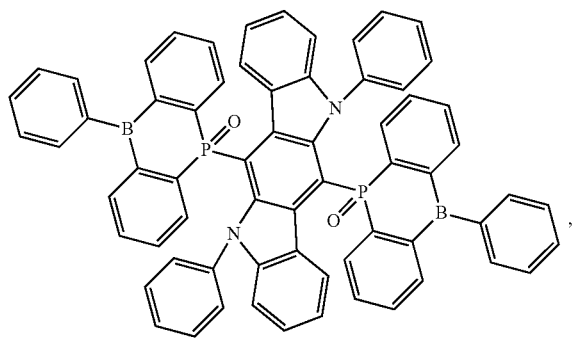
M71
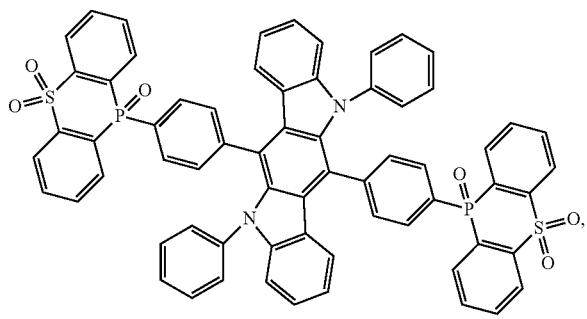

-continued
M72 M73
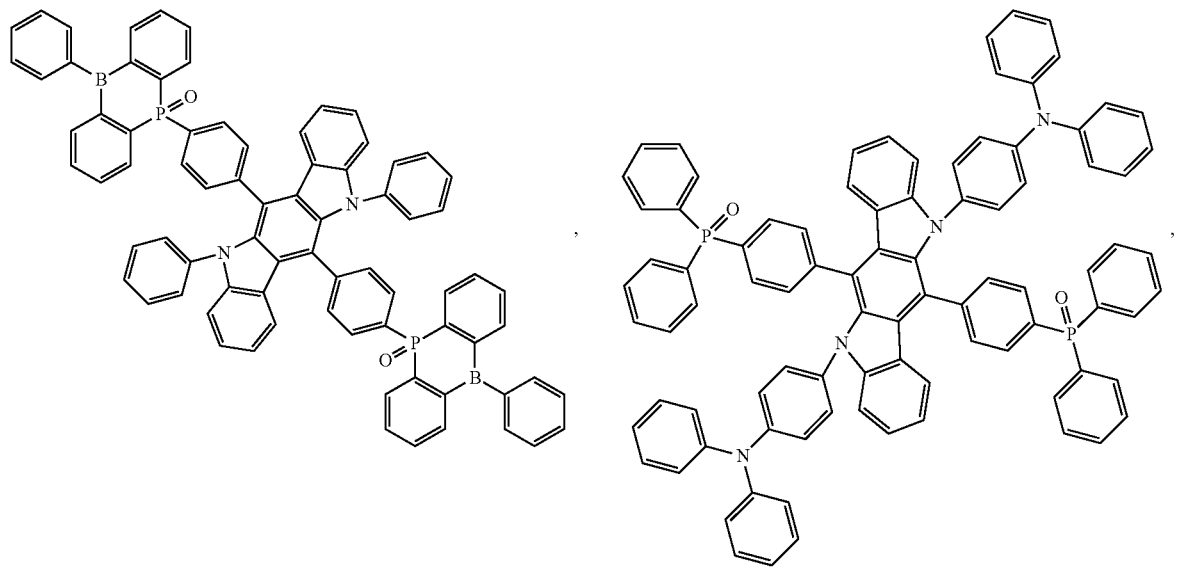
M74 M75
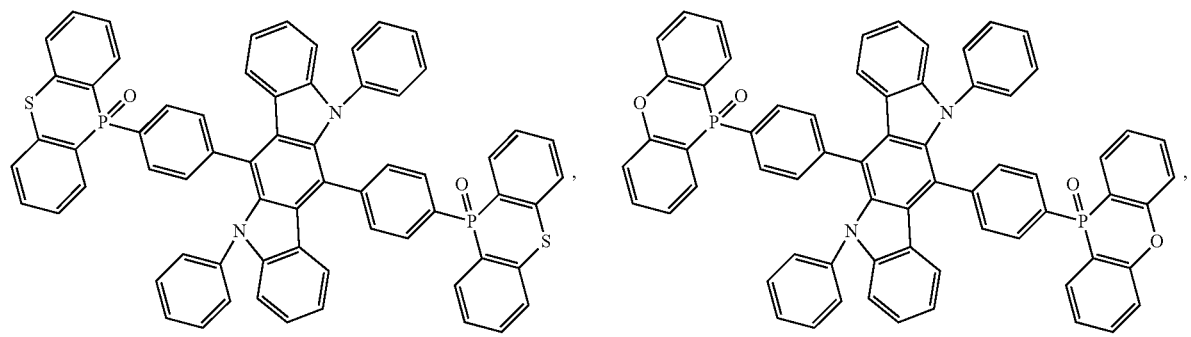
M76 M77
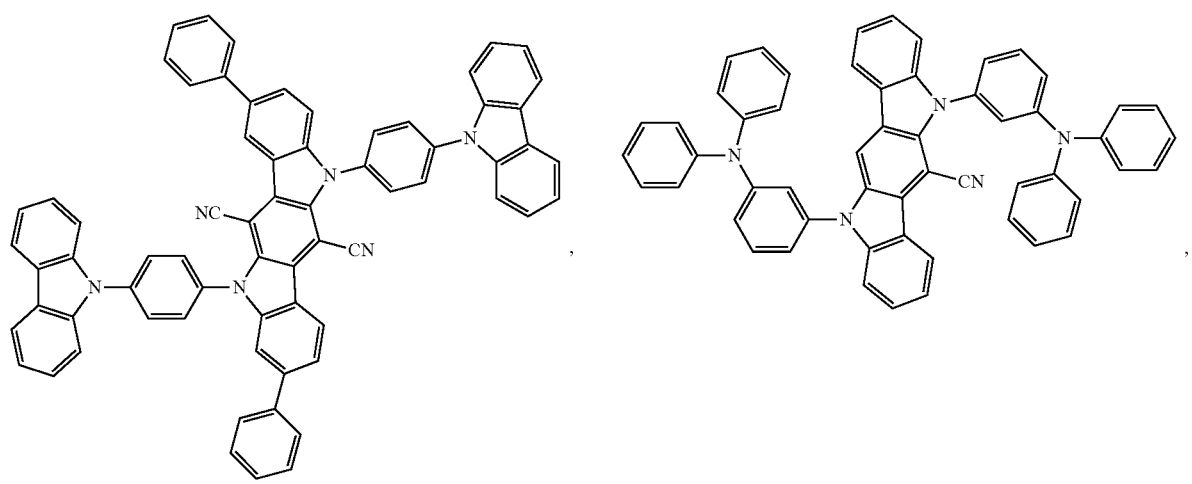

-continued
M78 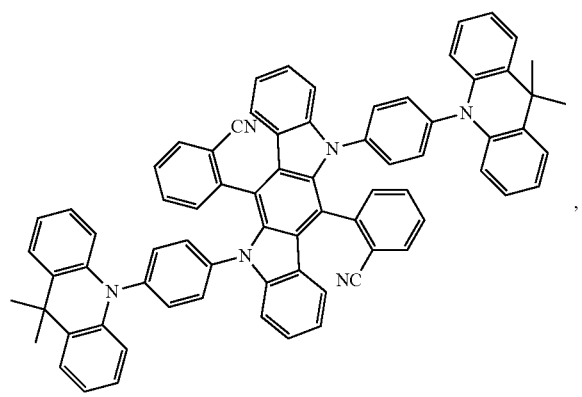
M79 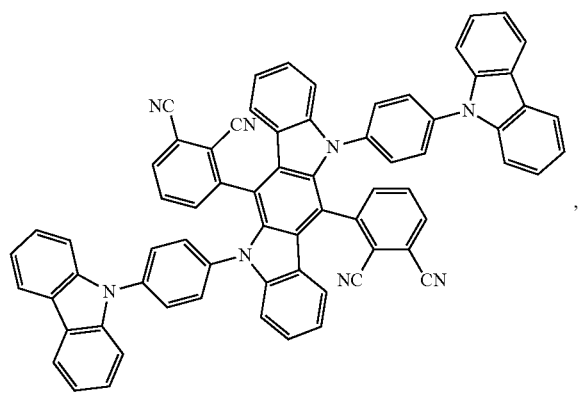
M80 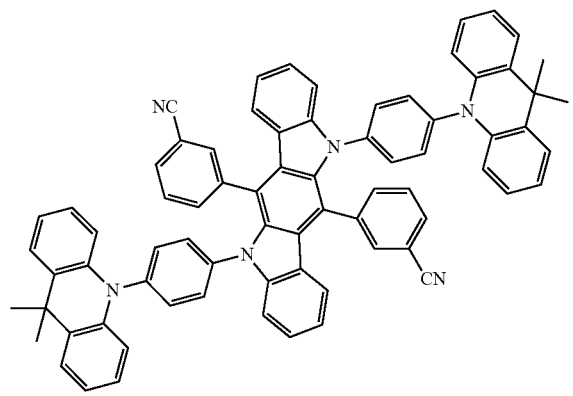
M81 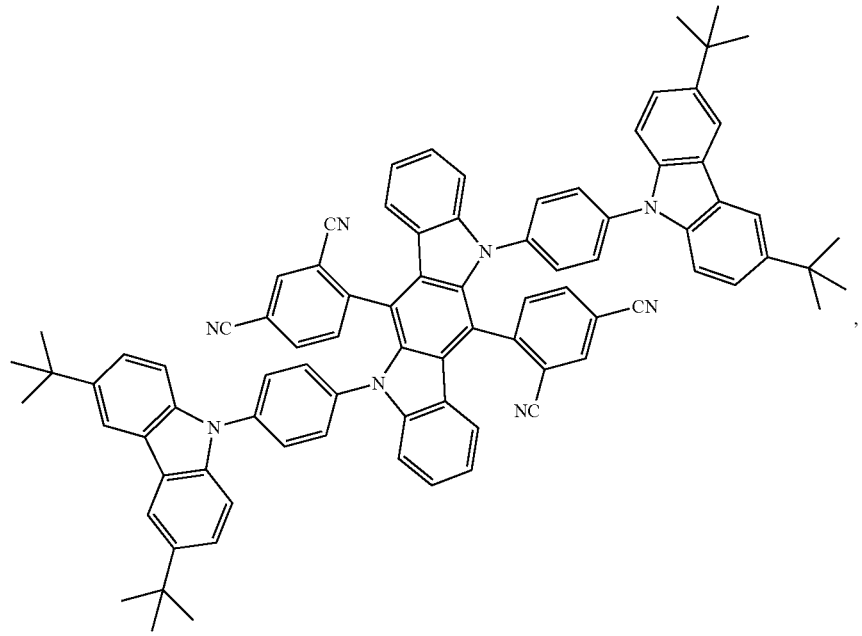

-continued
M82
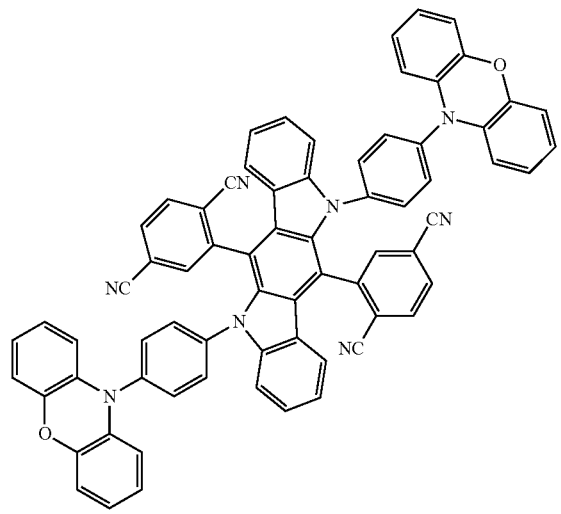
M83
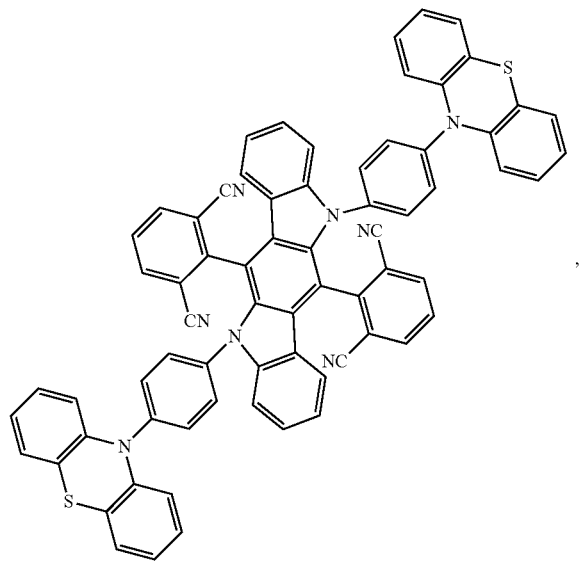
M84
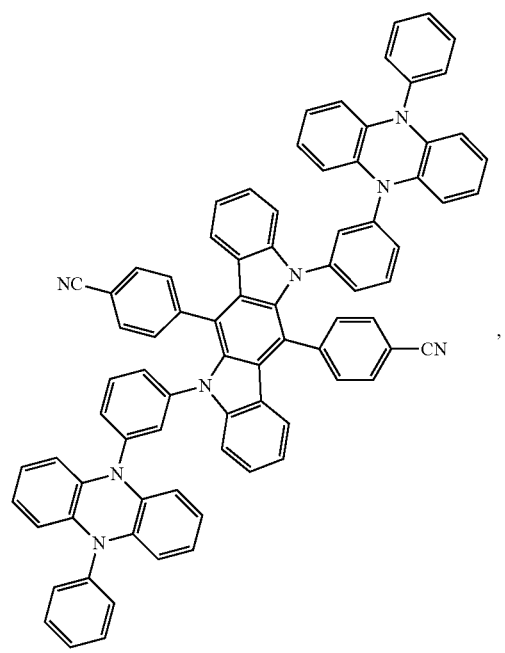
M85
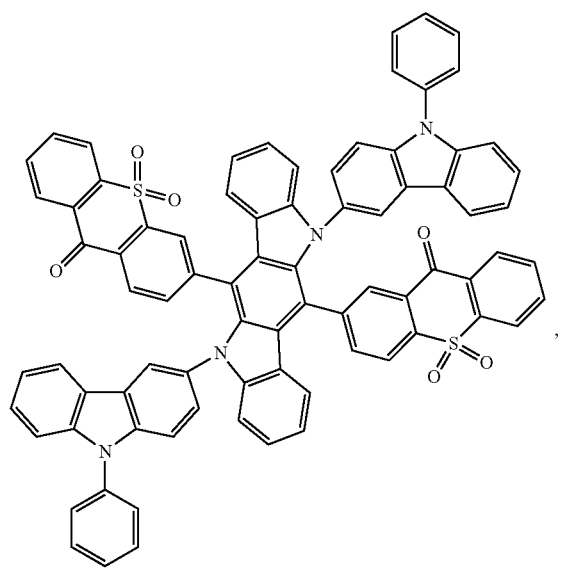

-continued
M86
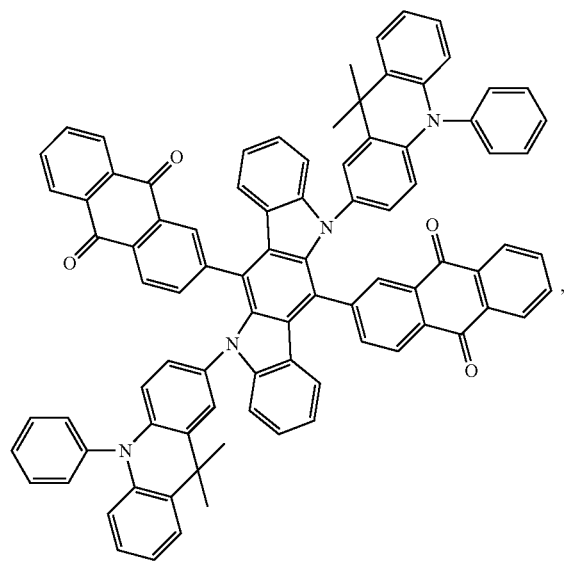
M87
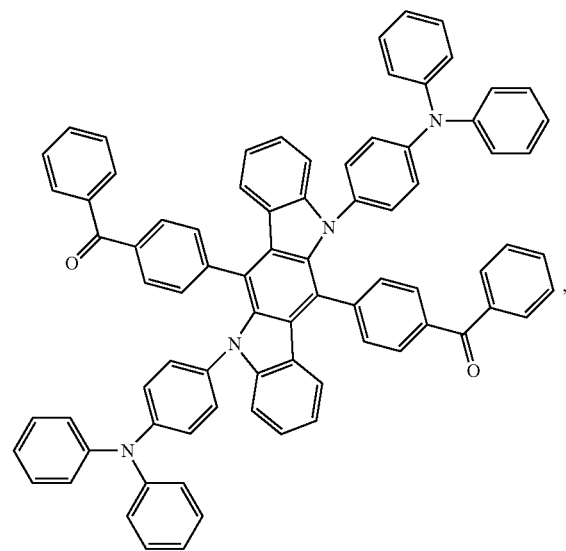
M88
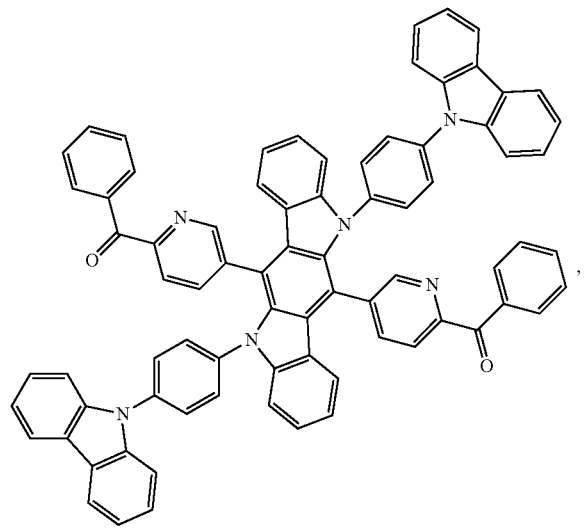
M89
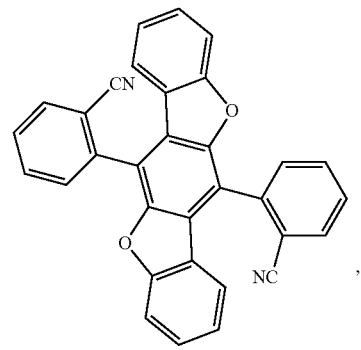
M90
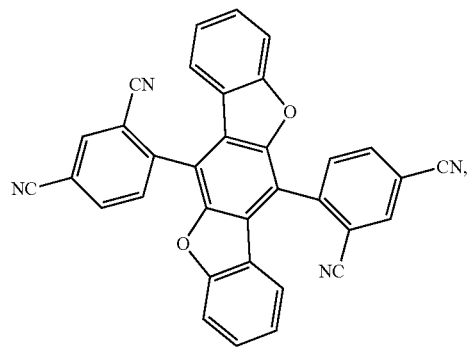
M91
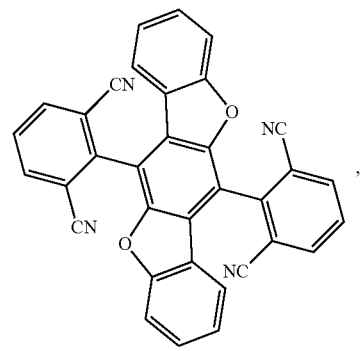

-continued
M92
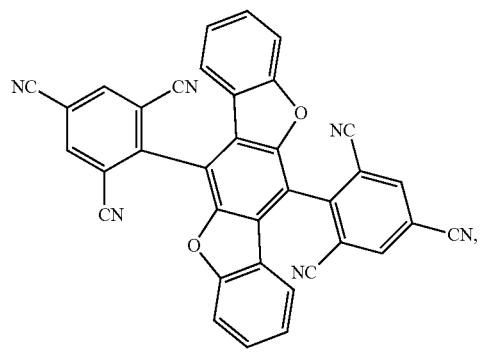
M93
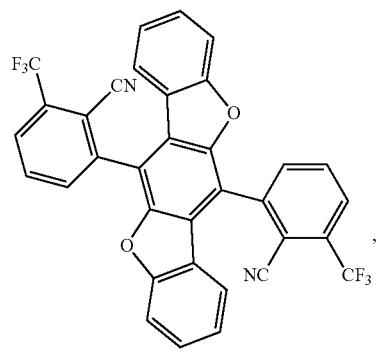
M94
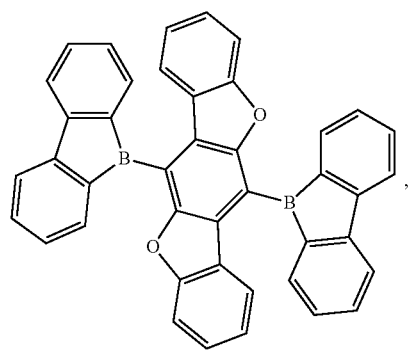
M95
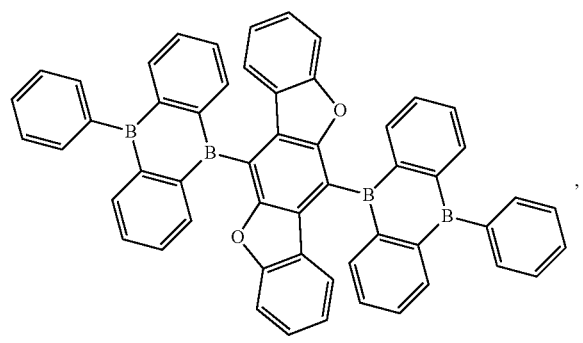
M96
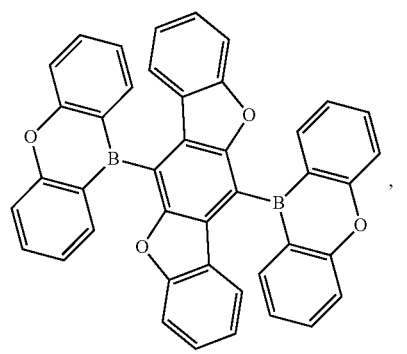
M97
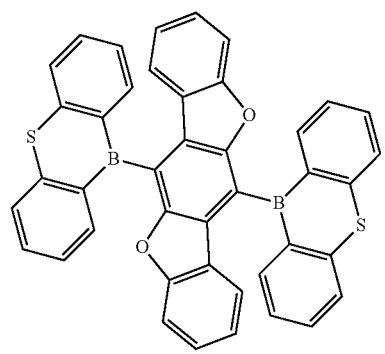
M98
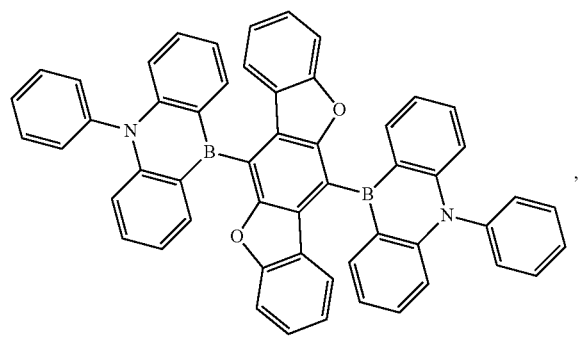

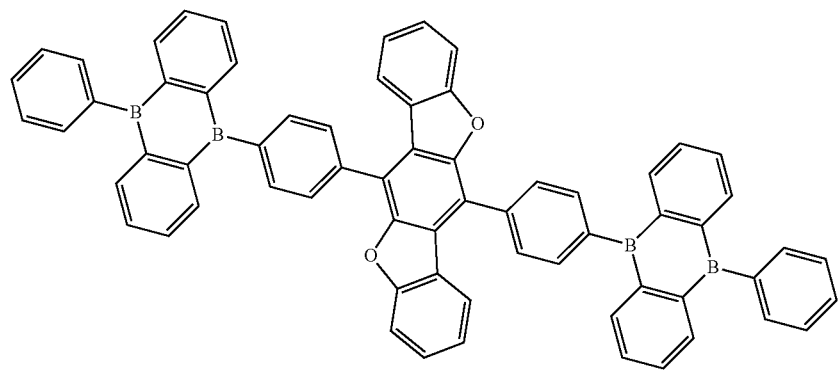
M99
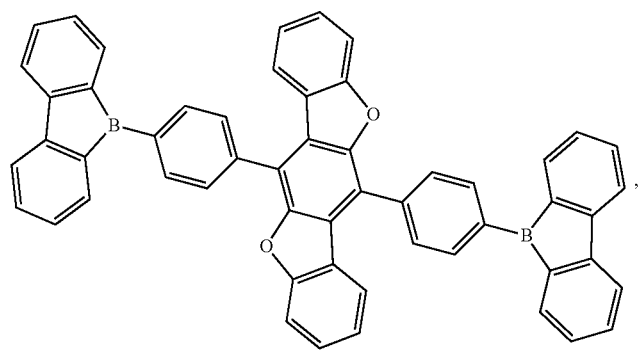
M100
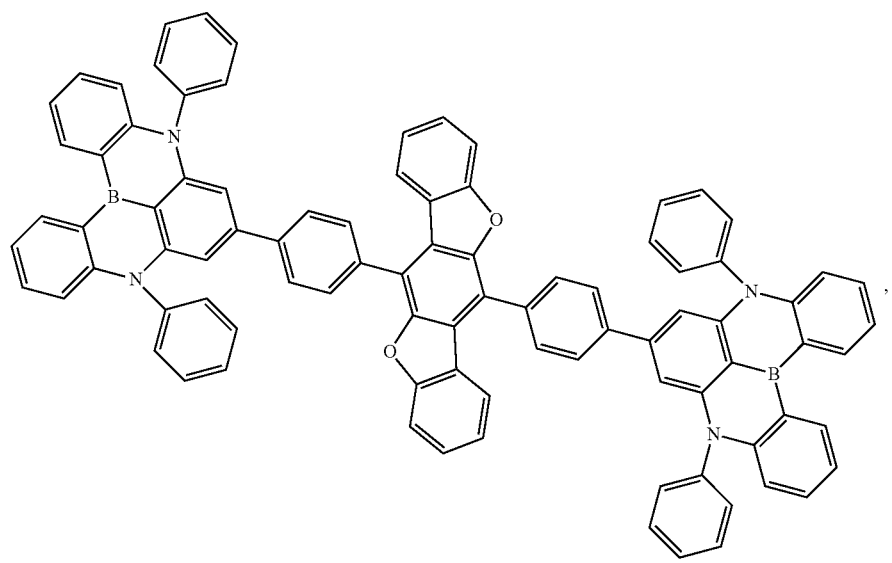
M101

-continued
M102
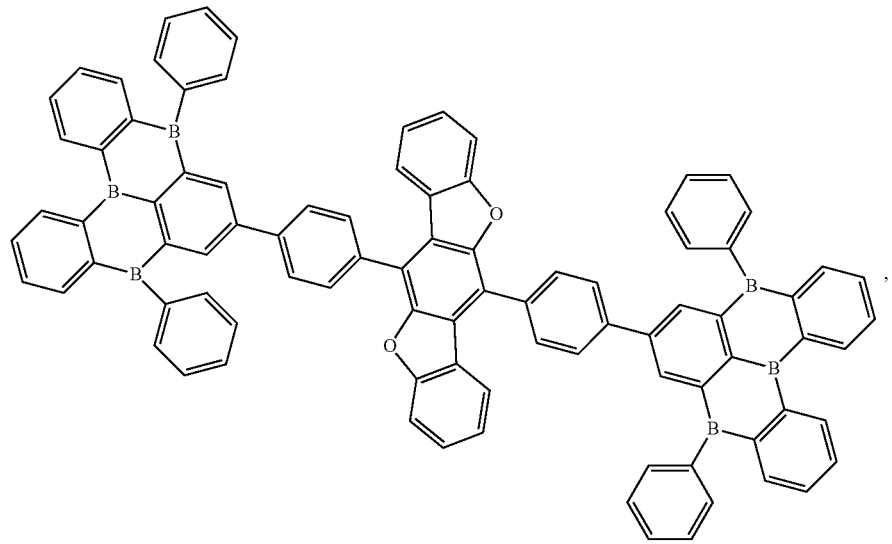
M103
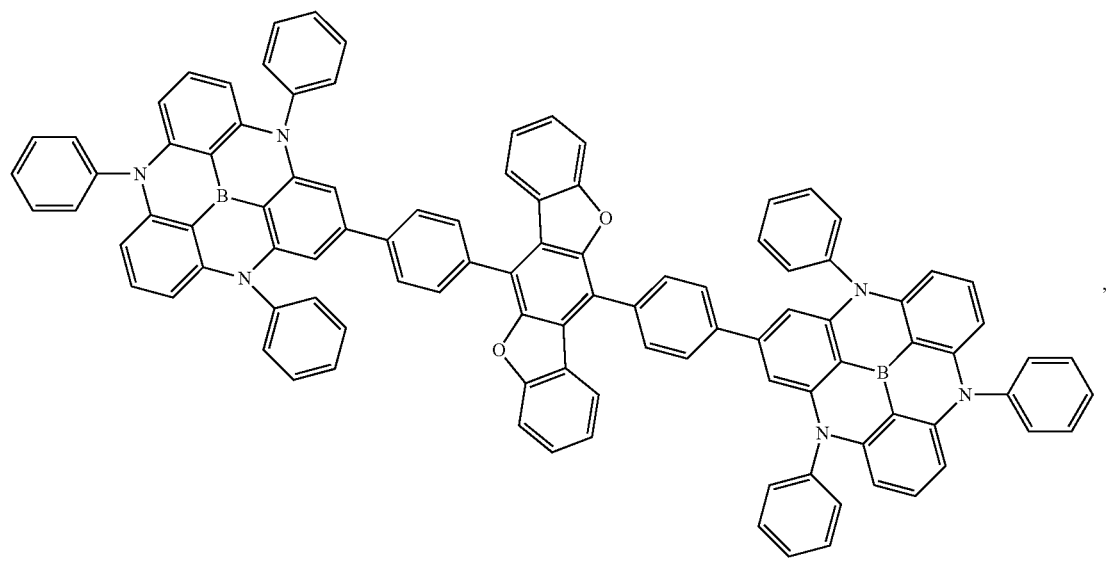
M104
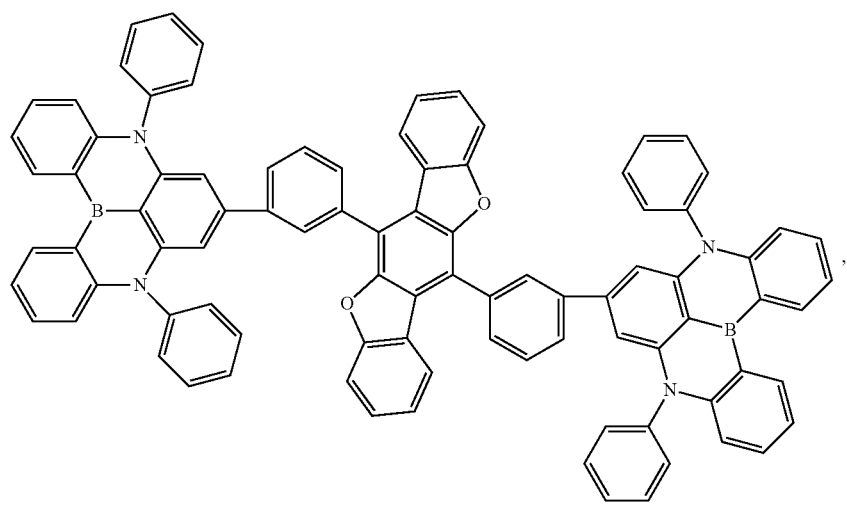

-continued
M105
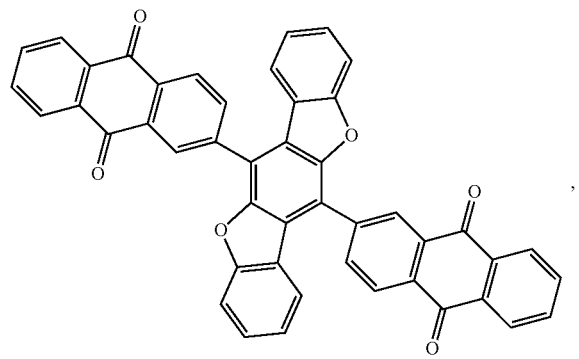
M106
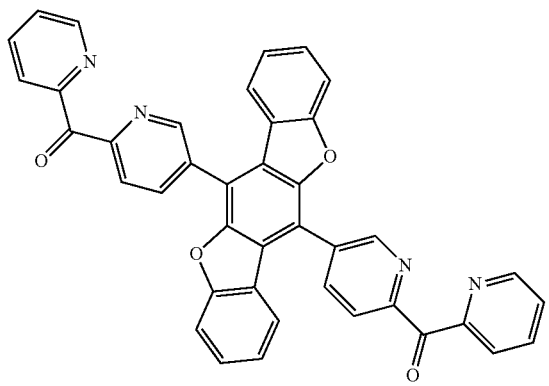
M107
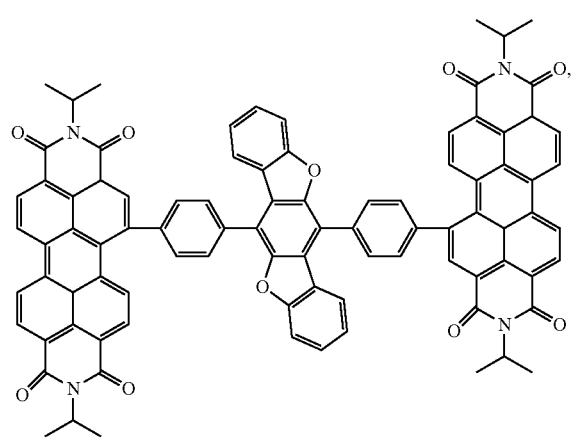
M108
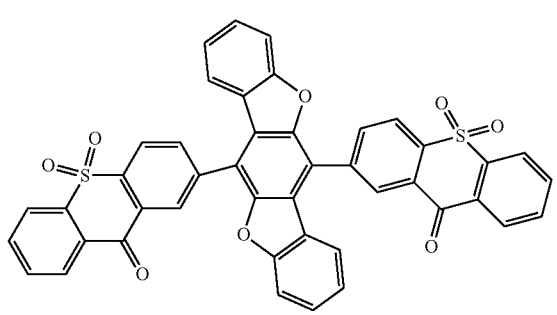
M109
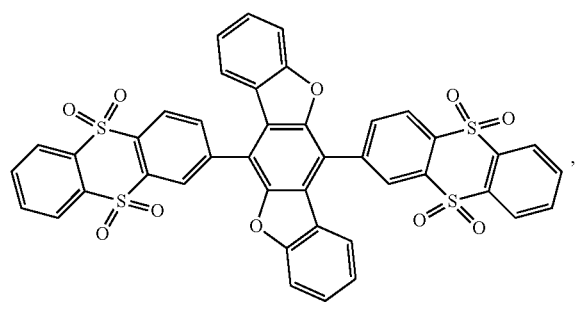
M110
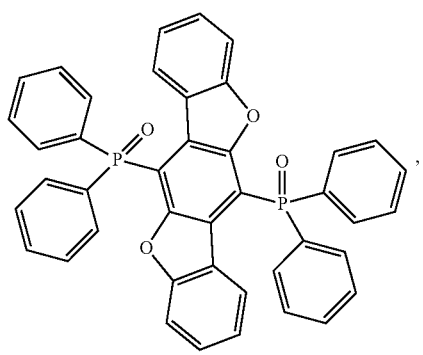
M111
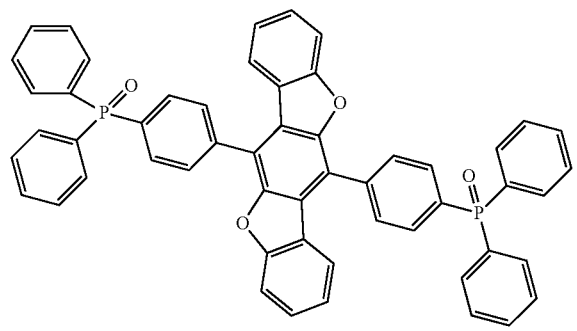
M112
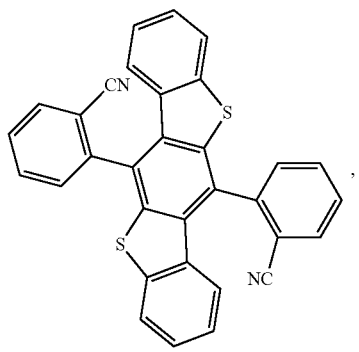

-continued
M113
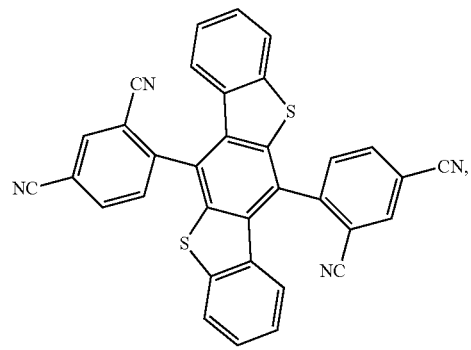
M114
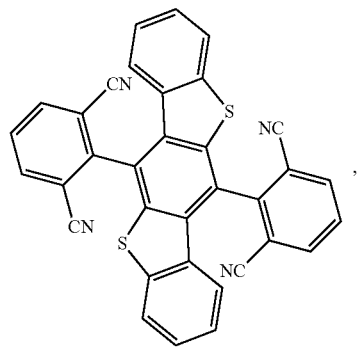
M115
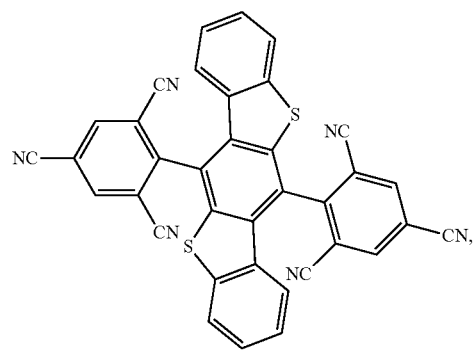
M116
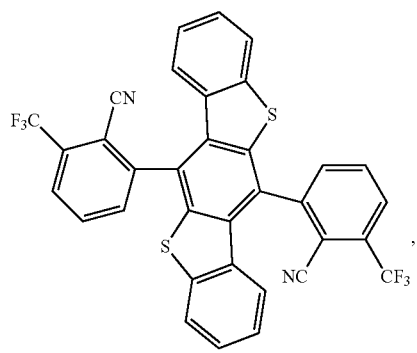
M117
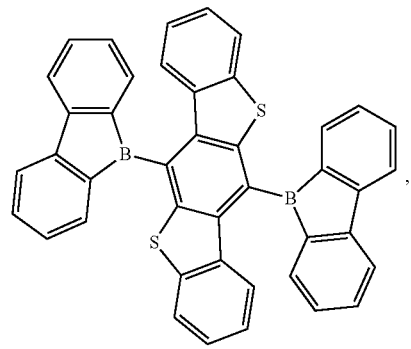
M118
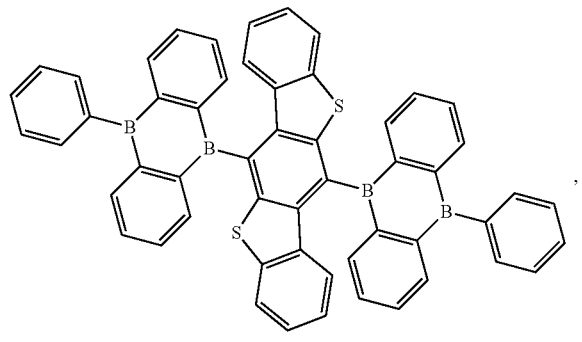
M119
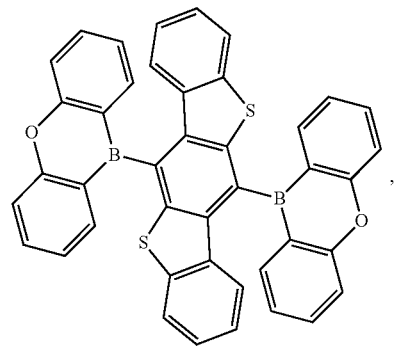
M120
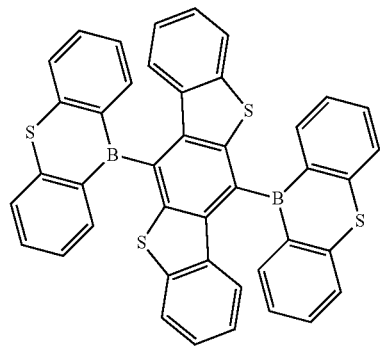

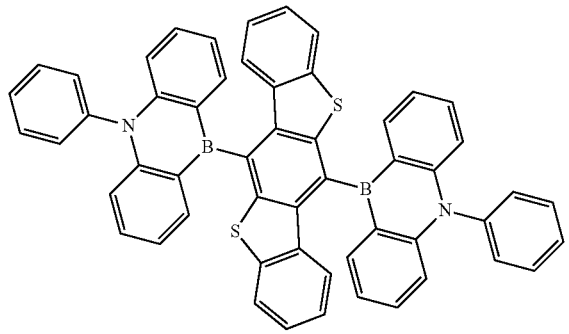
M121
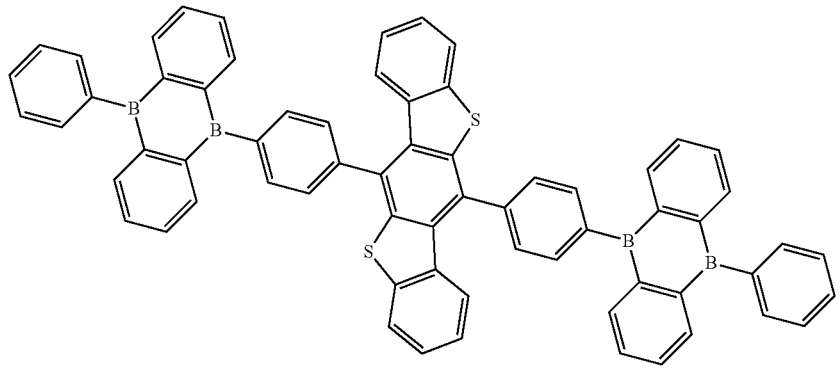
M122
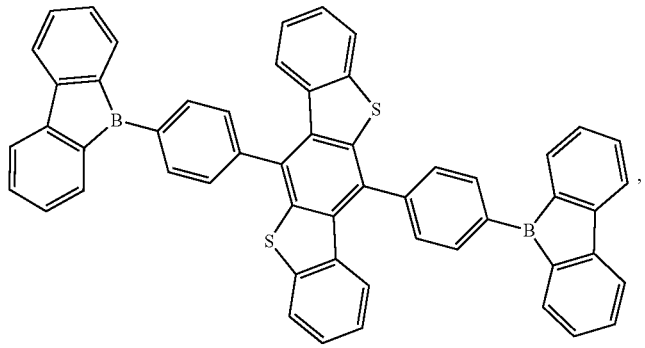
M123
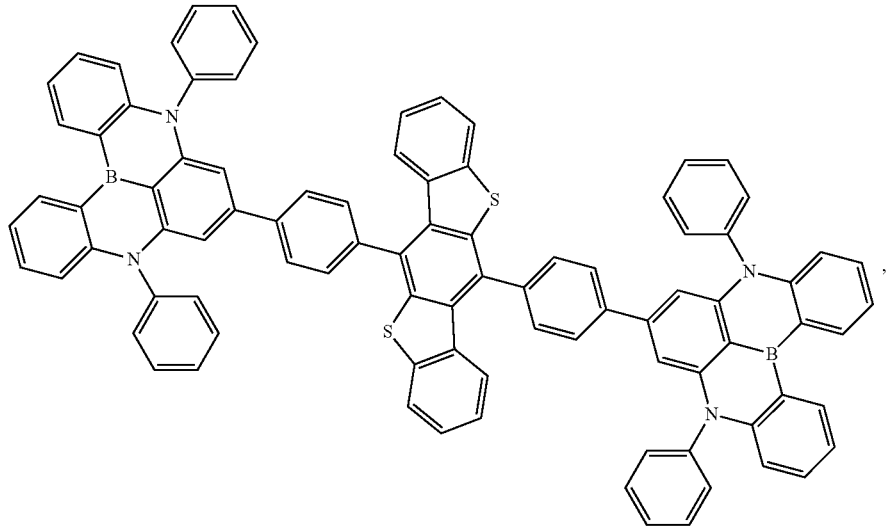
M124

M125
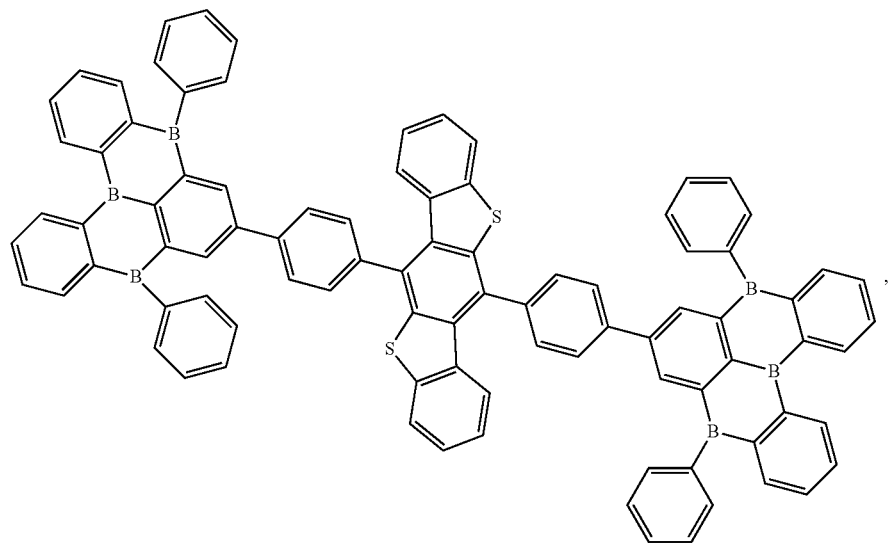
M126
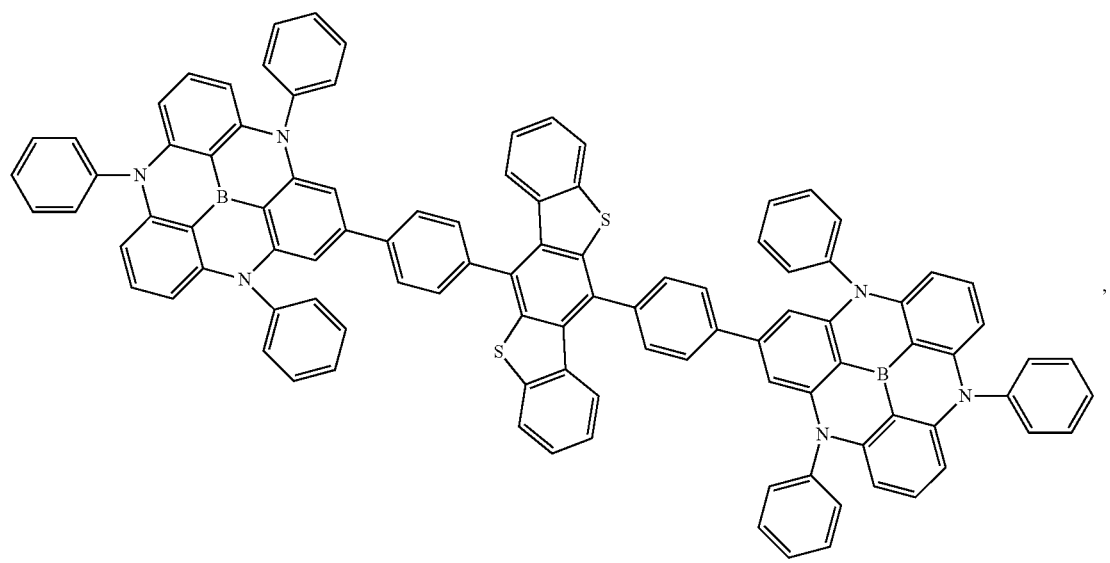
M127
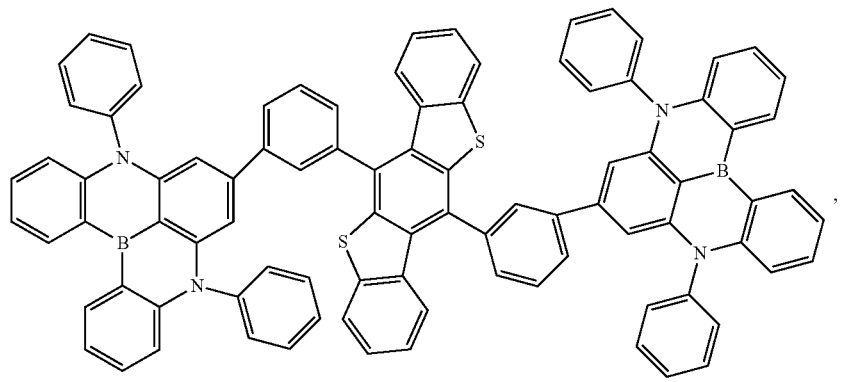

-continued
M128
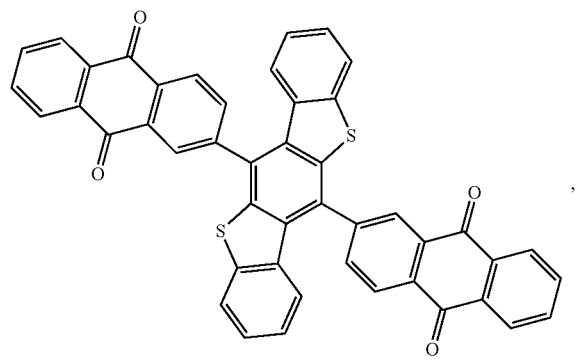,
M129
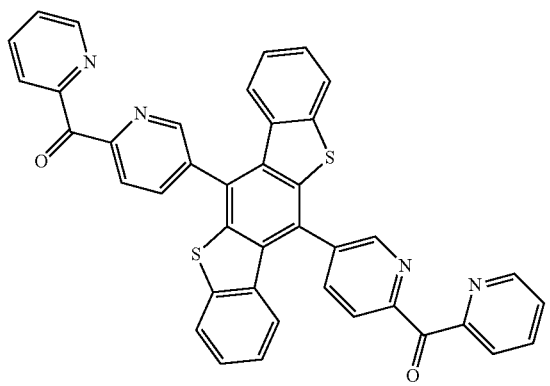,
M130
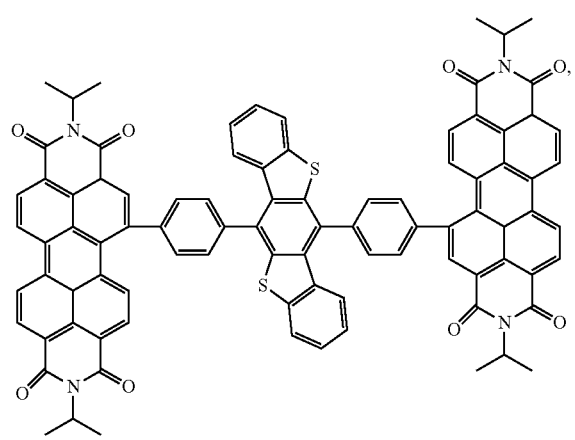,
M131
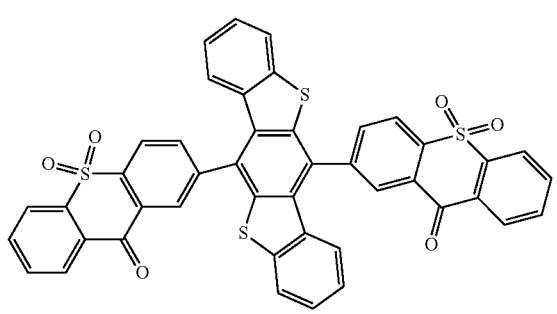,
M132
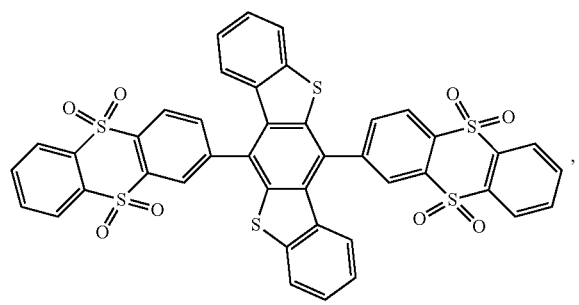,
M133
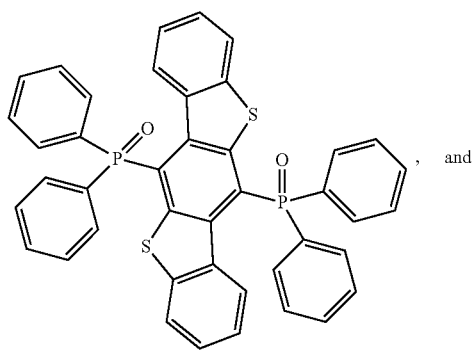, and
M134
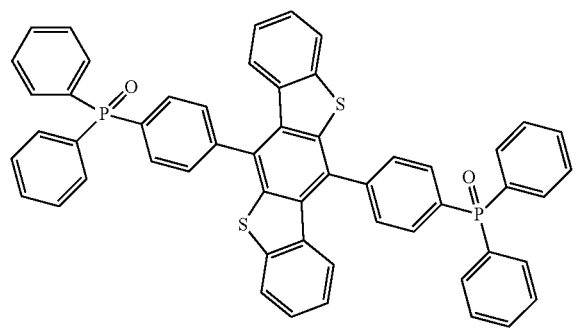.

The second aspect of the present disclosure is to provide a display panel comprising an OLED device, the OLED device comprises an anode, a cathode, and at least one organic thin film layer between the anode and the cathode, the organic thin film layer comprises a light emitting layer, and any one or a combination of at least two of a hole transport layer, a hole injection layer, an electron blocking layer, a hole blocking layer, an electron transport layer, and an electron injection layer.

The light emitting layer includes the compound as described above, and the compound is used as any one of a host material, a doping material, and a co-doping material.

In one embodiment, the light-emitting layer comprises a host material and a doping material, and the host material comprises the compound as described above.

In the OLED device according to the present disclosure, the anode material may be a metal, a metal oxide or a conductive polymer; wherein the metal includes copper, gold, silver, iron, chromium, nickel, manganese, palladium, platinum, or the alloys thereof, the metal oxide includes indium tin oxide (ITO), indium zinc oxide (IZO), zinc oxide, or indium gallium zinc oxide (IGZO), and the conductive polymer includes polyaniline, polypyrrole, or poly (3-methylthiophene). In addition to the material and combinations thereof as described above which facilitate hole injection, other materials known to be suitable as an anode can be included.

In the OLED device, the cathode material may be a metal or a multilayer metal material; wherein the metal includes aluminum, magnesium, silver, indium, tin, titanium, or alloys thereof, and the multilayer metal material includes LiF/Al, LiO$_2$/Al, or BaF$_2$/Al. In addition to the material and combinations thereof as described above which facilitate electron injection, other materials known to be suitable as cathodes can be included.

In the OLED device, the organic thin film layer includes at least one light emitting layer (EML) and any one or a combination of at least two of a hole transport layer (HTL), a hole injection layer (HIL), an electron blocking layer (EBL), a hole blocking layer (HBL), an electron transport layer (ETL) and an electron injection layer (EIL) disposed on both sides of the light emitting layer, wherein the hole/electron injection and transport layer may be a carbazole compound, an arylamine compound, a benzimidazole compound, or a metal compound.

A schematic diagram of the OLED device is shown in FIG. 1. The OLED device includes an anode 101 and a cathode 102, a light emitting layer 103 disposed between the anode 101 and the cathode 102, a first organic thin film layer 104 and a second organic thin film layer 105 are provided on both sides of the light emitting layer 103, the first organic thin film layer 104 is any one or a combination of at least two of a hole transport layer (HTL), a hole injection layer (HIL), or an electron blocking layer (EBL), and the second organic thin film layer 105 is any one or a combination of at least two of a hole blocking layer (HBL), an electron transport layer (ETL) or an electron injection layer (EIL).

The OLED device can be prepared by the following method: forming an anode on a transparent or non-transparent smooth substrate, forming an organic thin layer on the anode, and forming a cathode on the organic thin layer. Wherein, the organic thin layer can be formed by known film-forming methods such as evaporation, sputtering, spin coating, dipping, and ion plating.

The third aspect of the present disclosure is to provide an electronic device comprising the display panel as described above.

The compound having a structure represented by Formula I provided by the present disclosure are exemplarily prepared by the following synthetic route:

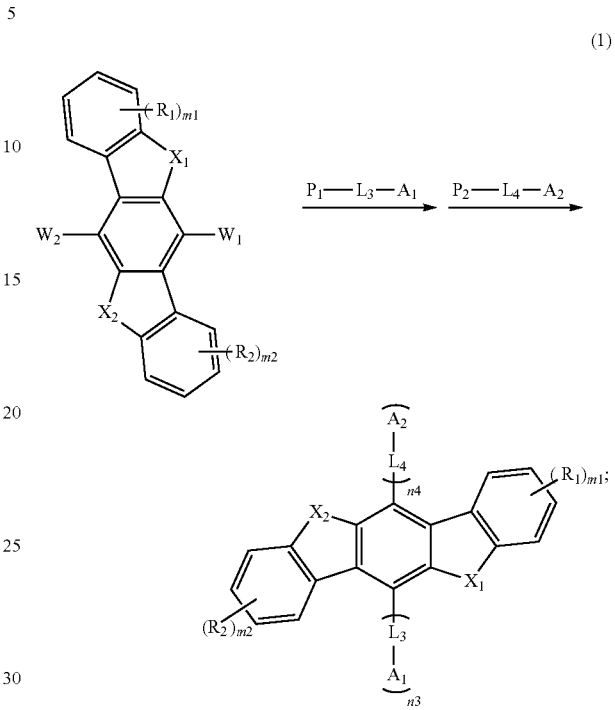

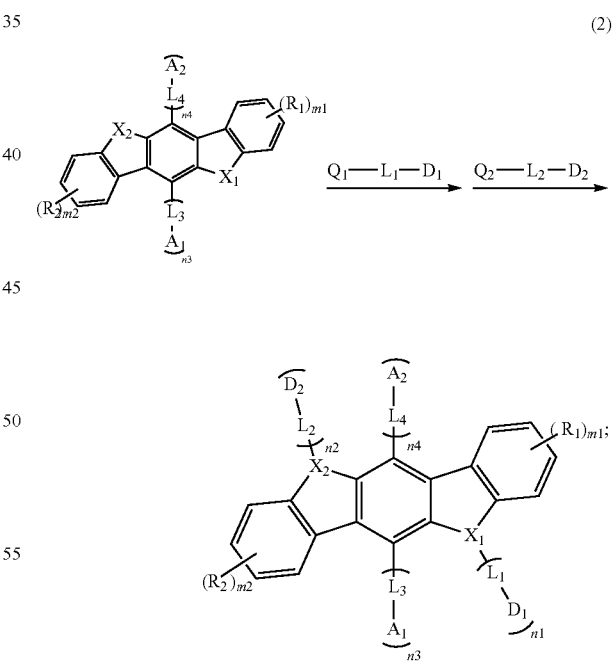

In the above steps (1) and (2), $n_1$, $n_2$, $n_3$, $n_4$, $X_1$, $X_2$, $D_1$, $D_2$, $L_1$, $L_2$, $L_3$, $L_4$, $A_1$, $A_2$, $R_1$, $R_2$, $m_1$, and $m_2$ have the same defined range as in the above Formula I; $W_1$, $W_2$, $Q_1$, and $Q_2$ each is independently halogen-based reactive groups (for example, Br.), $P_1$ and $P_2$ each is independently boron- or tin-containing reactive groups.

Example 1

This Example provides a compound having the following structure:

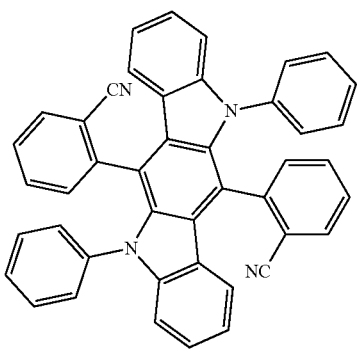

M3

Here its preparation method includes the following steps:

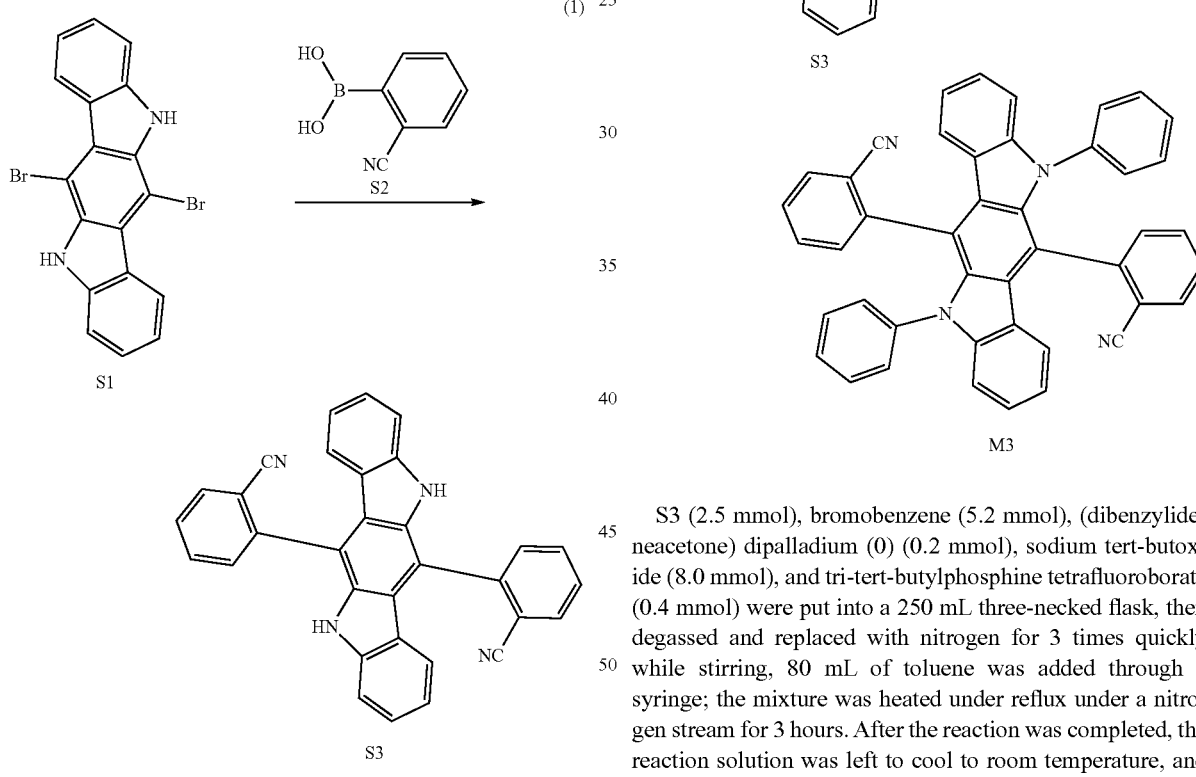

Under nitrogen protection, compound S1 (1.5 mmol), S2 (3.2 mmol), [Pd$_2$(dba)$_3$].CHCl$_3$ (0.05 mmol) and HP(tBu)$_3$.BF$_4$ (0.1 mmol) were added to a 100 mL two-necked flask, then 30 mL of toluene (passing N$_2$ for 15 min in advance to remove oxygen) was injected therein, and then 2.5 mL of a 1 M K$_2$CO$_3$ aqueous solution (passing N$_2$ for 15 min in advance to remove oxygen) was added dropwise and stirred at room temperature overnight. After the reaction was completed, 20 mL of deionized water was added, and then a few drops of 2 M HCl was added dropwise; the mixture was extracted with dichloromethane, the organic phase was collected, and dried with anhydrous Na$_2$SO$_4$. The dried solution was filtered, and the solvent was removed on a rotary evaporator to obtain a crude product. The crude product was purified by a silica gel column chromatography, and finally purified to obtain the intermediate product S14 (1.28 mmol, yield: 85%).

The structure of S3 was tested: MALDI-TOF-MS (m/z) obtained by Matrix assisted laser desorption ionization time-of-flight mass spectrometry: C$_{32}$H$_{18}$N$_4$, calculated value: 458.2, found value: 458.4.

S3 (2.5 mmol), bromobenzene (5.2 mmol), (dibenzylideneacetone) dipalladium (0) (0.2 mmol), sodium tert-butoxide (8.0 mmol), and tri-tert-butylphosphine tetrafluoroborate (0.4 mmol) were put into a 250 mL three-necked flask, then degassed and replaced with nitrogen for 3 times quickly while stirring, 80 mL of toluene was added through a syringe; the mixture was heated under reflux under a nitrogen stream for 3 hours. After the reaction was completed, the reaction solution was left to cool to room temperature, and then water was added thereto. The reaction solution was extracted with dichloromethane and washed with saturated brine. After the organic layer was dried over anhydrous sodium sulfate, the solvent was distilled off and refined using column chromatography to obtain the target product M3 (2.04 mmol, yield: 82%).

The structure of M3 was tested: MALDI-TOF-MS (m/z) obtained by Matrix assisted laser desorption ionization time-of-flight mass spectrometry: C$_{44}$H$_{26}$N$_4$, calculated value: 610.2, found value: 610.5;

Elemental analysis calculated value: C 86.53, H 4.29, N 9.17; found value: C 86.56, H 4.21, N 9.15.

Example 2

This Example provides a compound having the following structure:

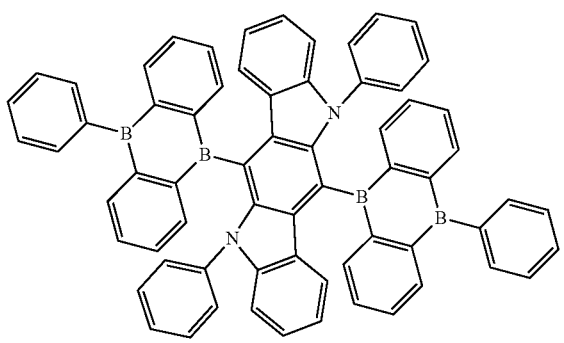

M16 its preparation method includes the following steps:

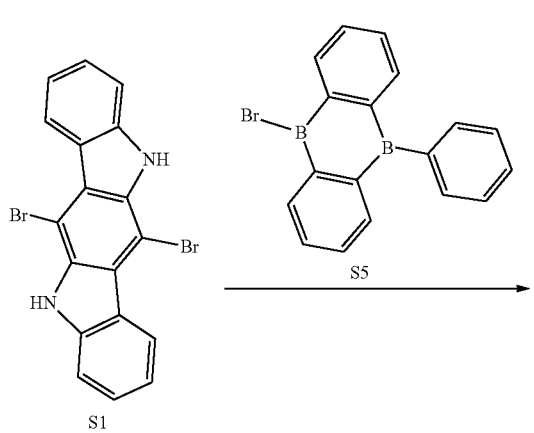

(1)

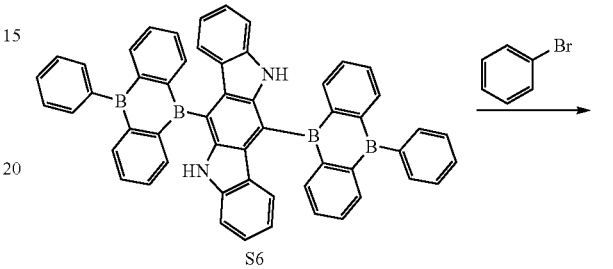

(2)

Under a condition of −78° C., S1 (1.8 mmol) was dissolved in diethyl ether (100 mL), and then n-BuLi (3.9 mmol) in n-hexane was added dropwise; the reaction solution was continuously stirred for 2 h, slowly warmed to room temperature and stirred at room temperature for 1 h. The reaction solution was cooled to −78° C. again, and 90 mL of S5 (3.8 mmol) in toluene was added dropwise while stirring; the mixture was slowly warmed to room temperature and stirred overnight. All solvents were removed by distillation under reduced pressure, and the crude product was collected. The crude product was washed with methanol (3×40 mL) and pentane (3×40 mL), and the crude product was collected again. The crude product was purified by a silica gel column chromatography using a mixed solvent of n-hexane and chloroform in a volume ratio of 5:1 as the eluent, and finally purified to obtain intermediate S6 (0.97 mmol, yield: 54%).

The structure of S6 was tested: MALDI-TOF-MS (m/z) obtained by Matrix assisted laser desorption ionization time-of-flight mass spectrometry: $C_{54}H_{36}B_4N_2$, calculated value: 756.3, found value: 756.5;

Here S6 (3.0 mmol), S4 (6.2 mmol), (dibenzylideneacetone) dipalladium (0) (0.24 mmol), sodium tert-butoxide (10.0 mmol), and tri-tert-butylphosphine tetrafluoroborate (0.48 mmol) were put into a 250 mL three-necked flask, then degassed and replaced with nitrogen for 3 times quickly while stirring, 100 mL of toluene was added through a syringe. The mixture was heated under reflux for 3 hours under a stream of nitrogen. After the reaction was completed, the reaction solution was left to cool to room temperature, and then water was added to the reaction solution. The reaction solution was extracted with dichloromethane and washed with saturated brine. After the organic layer was dried over anhydrous sodium sulfate, the solvent was distilled off and refined using column chromatography to obtain the target product M16 (2.34 mmol, yield: 78%).

The structure of M16 was tested: MALDI-TOF-MS (m/z) obtained by Matrix assisted laser desorption ionization time-of-flight mass spectrometry: $C_{66}H_{44}B_4N_2$, calculated value: 908.4, found value: 908.5;

Elemental analysis calculated values are: C 87.27, H 4.88, B 4.76, N 3.08; found value: C 87.30, H 4.90, B 4.73, N 3.06.

Example 3

This Example provides a compound having the following structure:

M35

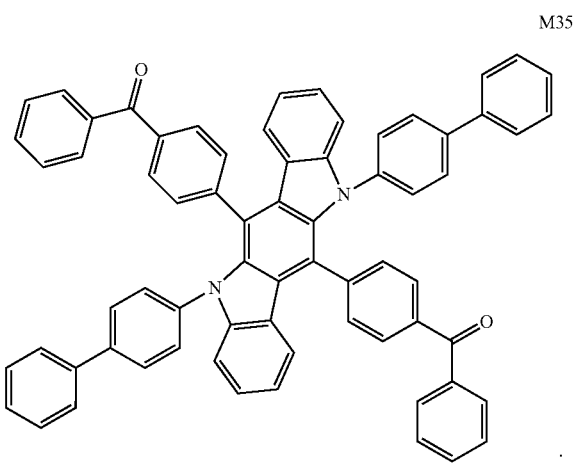 [SMILES: O=C(c1ccccc1)c1ccc(-c2c3c4ccccc4n(-c4ccc(-c5ccccc5)cc4)c3c(-c3ccc(C(=O)c4ccccc4)cc3)c3c4ccccc4n(-c4ccc(-c5ccccc5)cc4)c23)cc1]

Its preparation method includes the following steps:

(1)

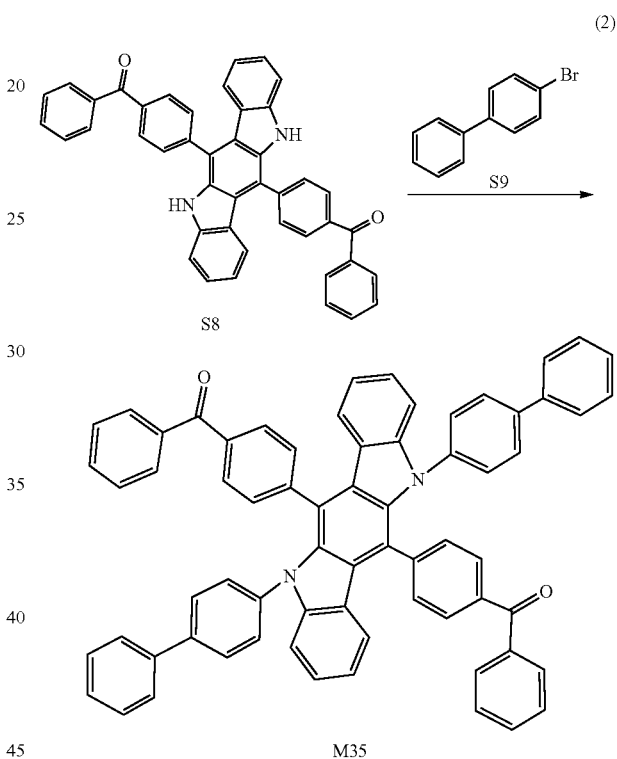

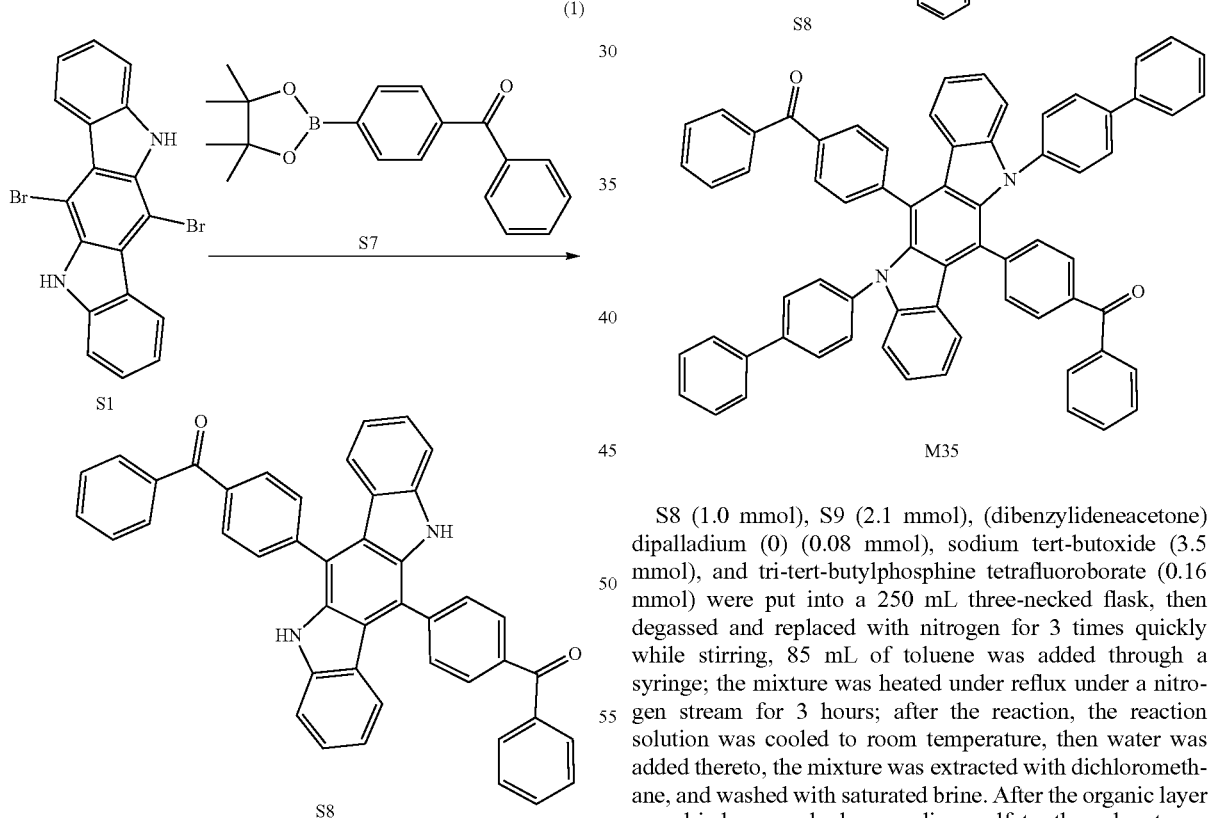

Under nitrogen protection, compound S1 (2.25 mmol), S7 (4.8 mmol), [Pd$_2$(dba)$_3$]·CHCl$_3$ (0.1 mmol) and HP(tBu)$_3$·BF$_4$ (0.2 mmol) were added to a 250 mL two-necked flask, then 60 mL of toluene (passing N$_2$ for 15 min in advance to remove oxygen) was injected therein, and then 4 mL of a 1 M K$_2$CO$_3$ aqueous solution (passing N$_2$ for 15 min in advance to remove oxygen) was added dropwise and stirred at room temperature overnight. After the reaction was completed, 35 mL of deionized water was added, and then a few drops of 2 M HCl was added dropwise; the mixture was extracted with dichloromethane, the organic phase was collected, and dried with anhydrous Na$_2$SO$_4$. The dried solution was filtered, and the solvent was removed on a rotary evaporator to obtain a crude product. The crude product was purified by a silica gel column chromatography, and finally purified to obtain the intermediate S8 (1.87 mmol, yield: 83%).

The structure of S8 was tested: MALDI-TOF-MS (m/z) obtained by Matrix assisted laser desorption ionization time-of-flight mass spectrometry: C$_{44}$H$_{28}$N$_2$O$_2$, calculated value: 616.2, found value: 616.4.

S8 (1.0 mmol), S9 (2.1 mmol), (dibenzylideneacetone) dipalladium (0) (0.08 mmol), sodium tert-butoxide (3.5 mmol), and tri-tert-butylphosphine tetrafluoroborate (0.16 mmol) were put into a 250 mL three-necked flask, then degassed and replaced with nitrogen for 3 times quickly while stirring, 85 mL of toluene was added through a syringe; the mixture was heated under reflux under a nitrogen stream for 3 hours; after the reaction, the reaction solution was cooled to room temperature, then water was added thereto, the mixture was extracted with dichloromethane, and washed with saturated brine. After the organic layer was dried over anhydrous sodium sulfate, the solvent was distilled off and refined using column chromatography to obtain the target product M35 (0.85 mmol, yield: 85%).

The structure of M35 was tested: MALDI-TOF-MS (m/z) obtained by Matrix assisted laser desorption ionization time-of-flight mass spectrometry: C$_{68}$H$_{44}$N$_2$O$_2$, calculated value: 920.3, found value: 920.5.

Elemental analysis calculated value: C 88.67, H 4.81, N 3.04, O 3.47; found value: C 88.70, H 4.83, N 3.01, O3.45.

Example 4

This Example provides a compound having the following structure:

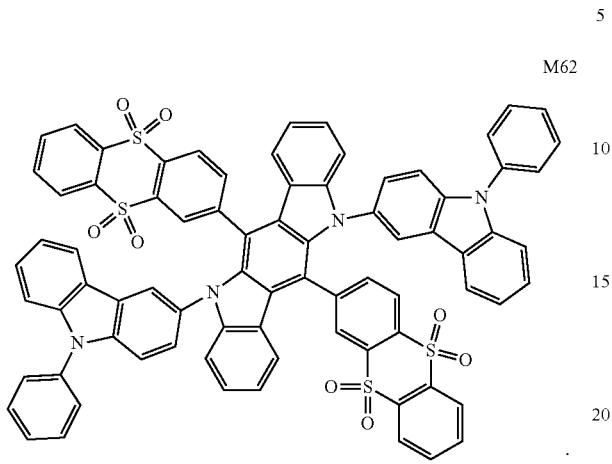

M62

Here its preparation method includes the following steps:

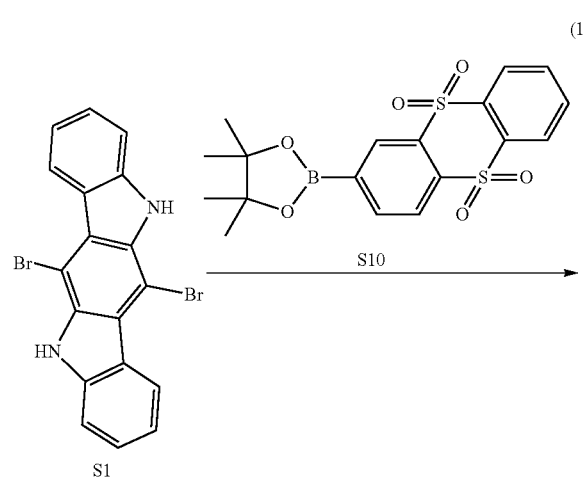

(1)

Under nitrogen protection, compound S1 (1.9 mmol), S10 (4.1 mmol), [Pd$_2$(dba)$_3$].CHCl$_3$ (0.1 mmol) and HP(tBu)$_3$.BF$_4$ (0.2 mmol) were added to a 250 mL two-necked flask; then 75 mL of toluene (passing N$_2$ for 15 min in advance to remove oxygen) was injected therein, and then 4.5 mL of a 1 M K$_2$CO$_3$ aqueous solution (passing N$_2$ for 15 min in advance to remove oxygen) was added dropwise and stirred at room temperature overnight. After the reaction was completed, 35 mL of deionized water was added, and then a few drops of 2 M HCl was added dropwise; the mixture was extracted with dichloromethane, the organic phase was collected, and dried with anhydrous Na$_2$SO$_4$. The dried solution was filtered, and the solvent was removed on a rotary evaporator to obtain a crude product. The crude product was purified by a silica gel column chromatography, and finally purified to obtain the intermediate S11 (1.43 mmol, yield: 75%).

The structure of S11 was tested: MALDI-TOF-MS (m/z) obtained by Matrix assisted laser desorption ionization time-of-flight mass spectrometry: C$_{42}$H$_{24}$N$_2$O$_8$S$_4$, calculated value: 812.0, found value: 812.2.

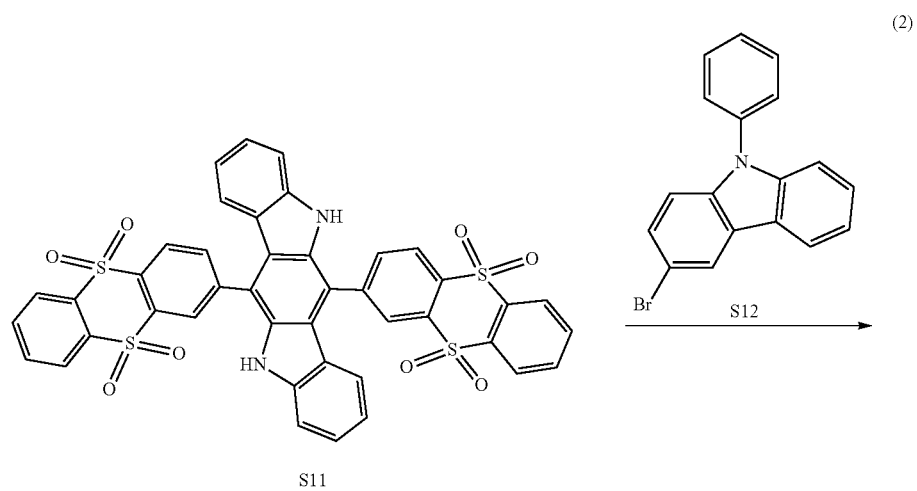

(2)

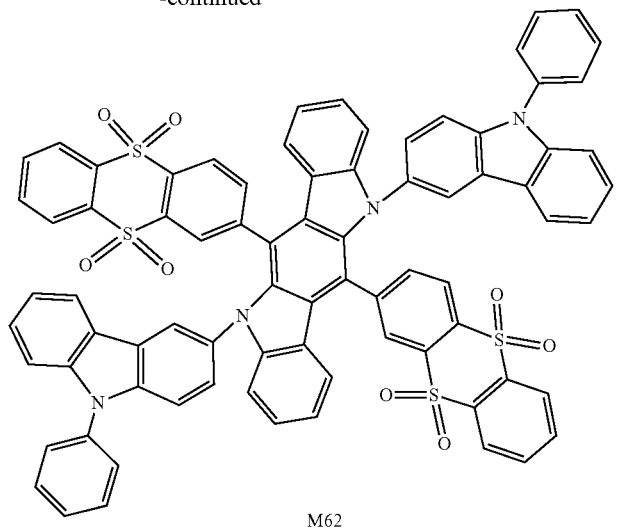

M62

S11 (1.3 mmol), S12 (2.7 mmol), (dibenzylideneacetone) dipalladium (0) (0.1 mmol), sodium tert-butoxide (4.6 mmol), and tri-tert-butylphosphine tetrafluoroborate (0.2 mmol) were put into a 250 mL three-necked flask, then degassed and replaced with nitrogen for 3 times quickly while stirring, 100 mL of toluene was added through a syringe. The mixture was heated under reflux under a nitrogen stream for 3 hours. After the reaction was completed, the reaction solution was left to cool to room temperature, and then water was added to the reaction solution. The reaction solution was extracted with dichloromethane and washed with saturated brine. After the organic layer was dried over anhydrous sodium sulfate, the solvent was distilled off and refined using column chromatography to obtain the target product M62 (1.07 mmol, yield: 82%).

The structure of M62 was tested: MALDI-TOF-MS (m/z) obtained by Matrix assisted laser desorption ionization time-of-flight mass spectrometry: $C_{78}H_{46}N_4O_8S_4$, calculated value: 1294.2, found value: 1294.5;

Elemental analysis calculated value: C 72.32, H 3.58, N 4.32, O 9.88, S 9.90; found value: C 72.35, H 3.60, N 4.30, O 9.86, S 9.89.

Example 5

This Example provides a compound having the following structure:

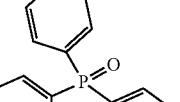

M73

Here its preparation method includes the following steps:

(1)

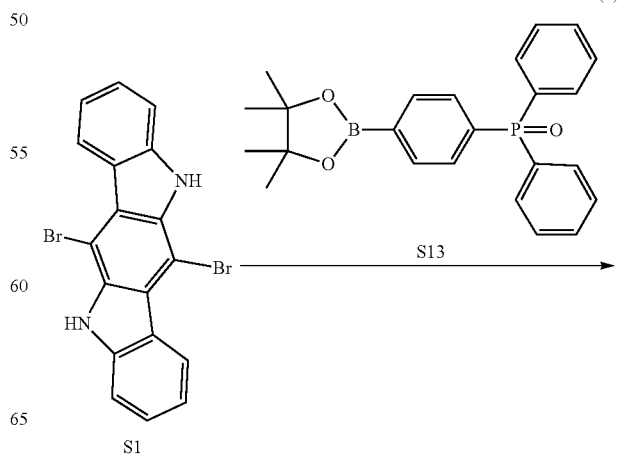

S1    S13

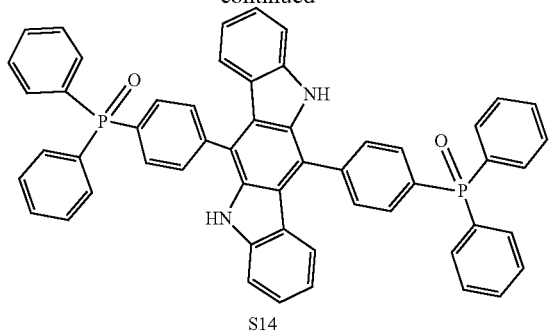

S14

Under nitrogen protection, compound S1 (2.3 mmol), S13 (4.9 mmol), [Pd$_2$(dba)$_3$].CHCl$_3$ (0.12 mmol) and HP(tBu)$_3$.BF$_4$ (0.24 mmol) were added to a 250 mL two-necked flask; then 85 mL of toluene (passing N$_2$ for 15 min in advance to remove oxygen) was injected therein, and then 6 mL of a 1 M K$_2$CO$_3$ aqueous solution (passing N$_2$ for 15 min in advance to remove oxygen) was added dropwise and stirred at room temperature overnight. After the reaction was completed, 45 mL of deionized water was added, and then a few drops of 2 M HCl was added dropwise; the mixture was extracted with dichloromethane, the organic phase was collected, and dried with anhydrous Na$_2$SO$_4$. The dried solution was filtered, and the solvent was removed on a rotary evaporator to obtain a crude product. The crude product was purified by a silica gel column chromatography, and finally purified to obtain the intermediate S14 (1.8 mmol, yield: 78%).

The structure of S14 was tested: MALDI-TOF-MS (m/z) obtained by Matrix assisted laser desorption ionization time-of-flight mass spectrometry: C$_{54}$H$_{38}$N$_2$O$_2$P$_2$, calculated value: 808.2, found value: 808.3.

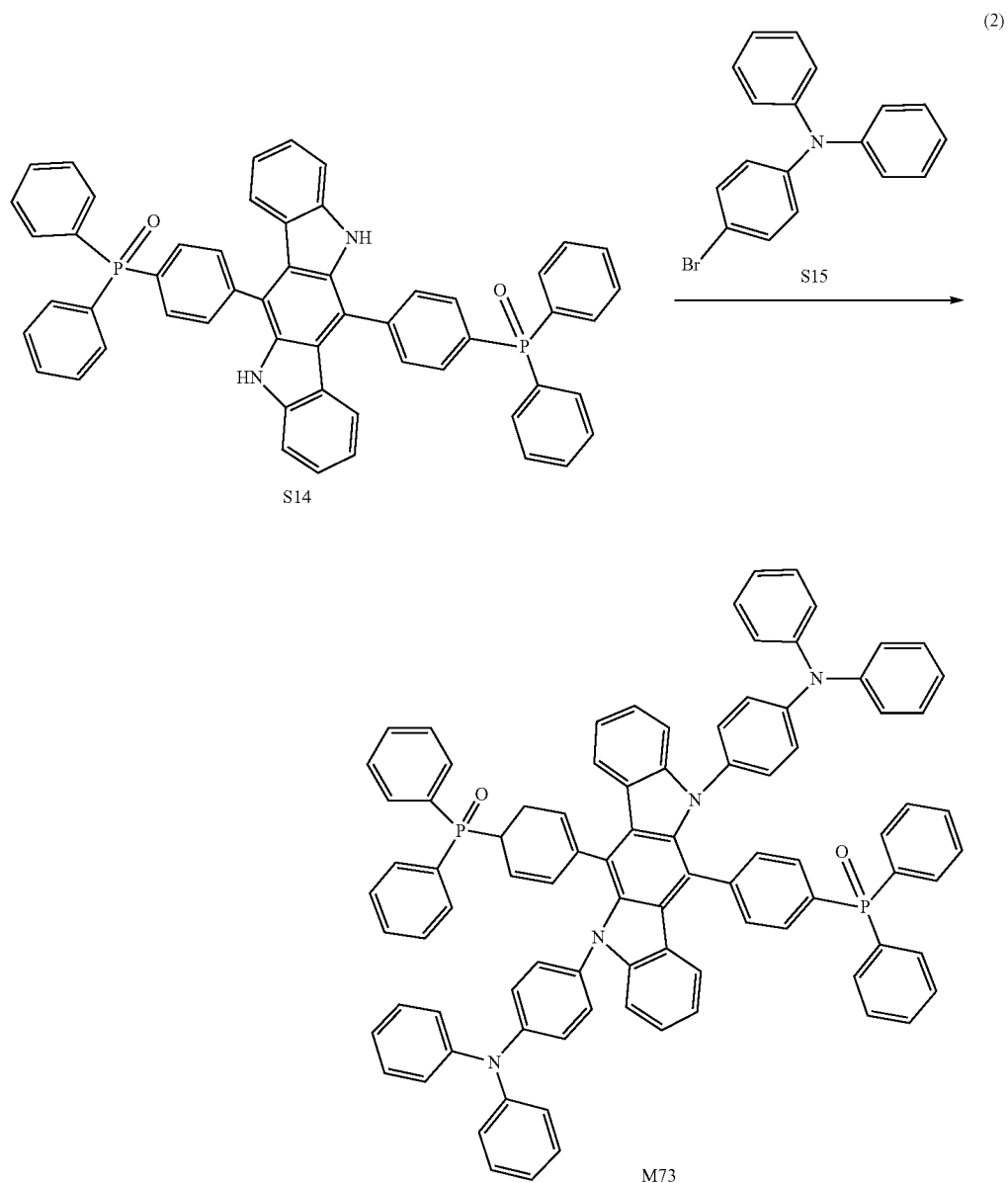

(2)

S14 (1.95 mmol), S15 (4.1 mmol), (dibenzylideneacetone) dipalladium (0) (0.15 mmol), sodium tert-butoxide (7 mmol), and tri-tert-butylphosphine tetrafluoroborate (0.3 mmol) were put into a 500 mL three-necked flask, then degassed and replaced with nitrogen for 3 times quickly while stirring, 150 mL of toluene was added through a syringe; the mixture was heated under reflux under a nitrogen stream for 3 hours; after the reaction, the reaction solution was cooled to room temperature, then water was added thereto, the mixture was extracted with dichloromethane, and washed with saturated brine. After the organic layer was dried over anhydrous sodium sulfate, the solvent was distilled off and refined using column chromatography to obtain the target product M73 (1.46 mmol, yield: 75%).

The structure of M73 was tested: MALDI-TOF-MS (m/z) obtained by Matrix assisted laser desorption ionization time-of-flight mass spectrometry: $C_{90}H_{64}N_4O_2P_2$, calculated value: 1294.4, found value: 1294.5;

Elemental analysis calculated value: C 83.44, H 4.98, N 4.32, O 2.47, P 4.78; found value: C 83.47, H 5.01, N 4.30, O 2.45, P 4.76.

Example 6

This Example provides a compound having the following structure:

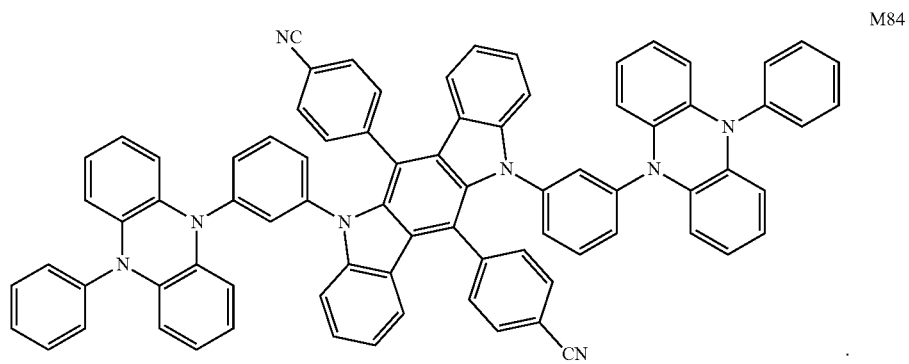

M84

Here its preparation method includes the following steps:

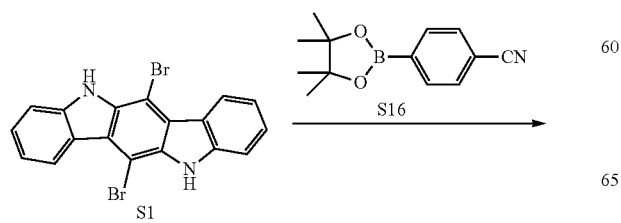

(1)

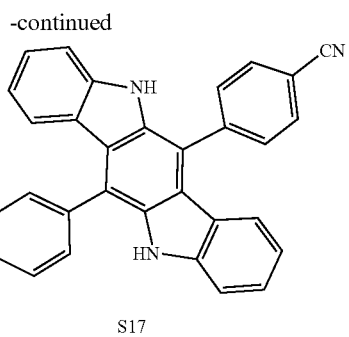

S17

Under nitrogen protection, compound S1 (2.5 mmol), S16 (5.3 mmol), [Pd$_2$(dba)$_3$].CHCl$_3$ (0.15 mmol) and HP(tBu)$_3$.BF$_4$ (0.30 mmol) were added to a 250 mL two-necked flask; then 90 mL of toluene (passing N$_2$ for 15 min in advance to remove oxygen) was injected therein, and then 8 mL of a 1 M K$_2$CO$_3$ aqueous solution (passing N$_2$ for 15 min in advance to remove oxygen) was added dropwise and stirred at room temperature overnight. After the reaction was completed, 60 mL of deionized water was added, and a few drops of 2 M HCl were further added dropwise. The mixture was extracted with dichloromethane, the organic phase was collected, and dried over anhydrous Na$_2$SO$_4$. The dried solution was filtered, and the solvent was removed on a rotary evaporator to obtain a crude product. The crude product was purified by a silica gel column chromatography, and finally purified to obtain the intermediate S17 (1.80 mmol, yield: 72%).

The structure of S17 was tested: MALDI-TOF-MS (m/z) obtained by Matrix assisted laser desorption ionization time-of-flight mass spectrometry: $C_{32}H_{18}N_4$, calculated value: 458.2, found value: 458.3.

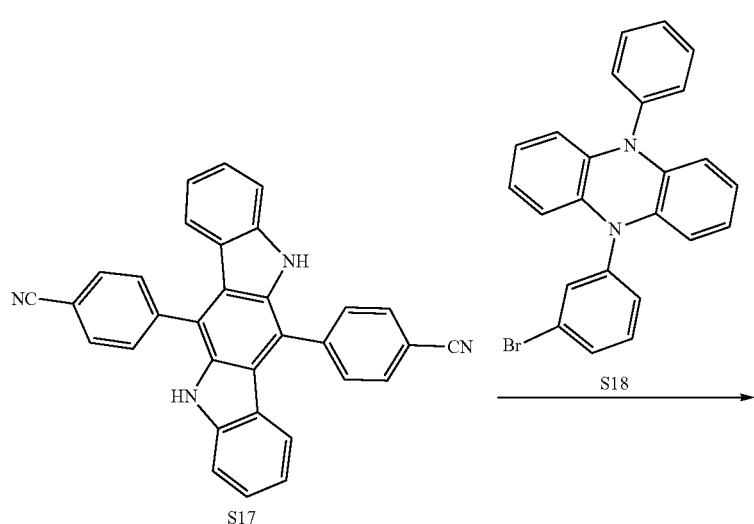

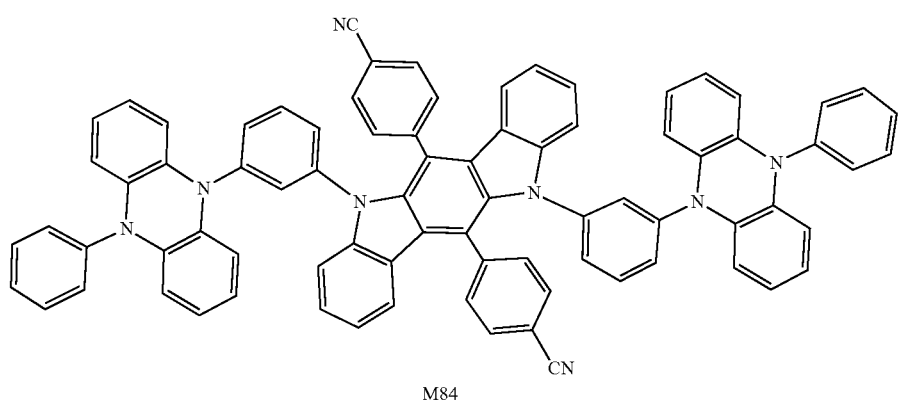

S17 (1.46 mmol), S18 (3.08 mmol), (dibenzylideneacetone) dipalladium (0) (0.12 mmol), sodium tert-butoxide (5.5 mmol), and tri-tert-butylphosphine tetrafluoroborate (0.24 mmol) were put into a 500 mL three-necked flask, then degassed and replaced with nitrogen for 3 times quickly while stirring, 120 mL of toluene was added through a syringe. The mixture was heated under reflux for 3 hours under a stream of nitrogen. After the reaction was completed, the reaction solution was left to cool to room temperature, and then water was added to the reaction solution. The reaction solution was extracted with dichloromethane and washed with saturated brine. After the organic layer was dried over anhydrous sodium sulfate, the solvent was distilled off and refined using column chromatography to obtain the target product M84 (1.05 mmol, yield: 72%).

The structure of M84 was tested: MALDI-TOF-MS (m/z) obtained by Matrix assisted laser desorption ionization time-of-flight mass spectrometry: $C_{80}H_{50}N_8$, calculated value: 1122.4; found value: 1122.4;

Elemental analysis calculated value: C 85.54, H 4.49, N 9.98; found value: C 85.58, H 4.47, N 9.96.

(2)

Example 7

This Example provides a compound having the following structure:

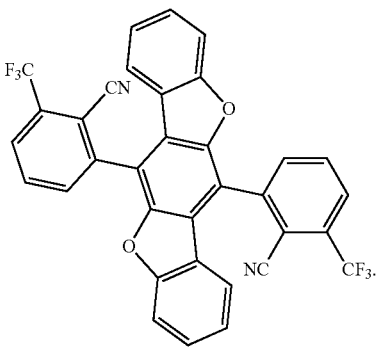

M93

The preparation method thereof is as follows:

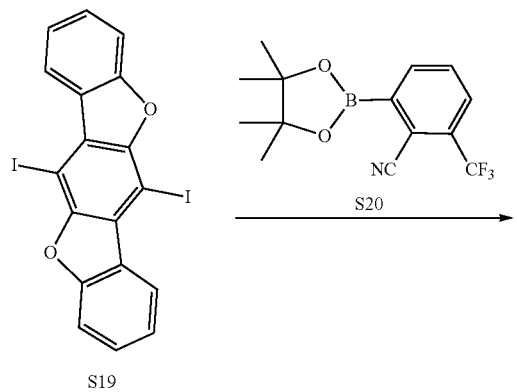

S19

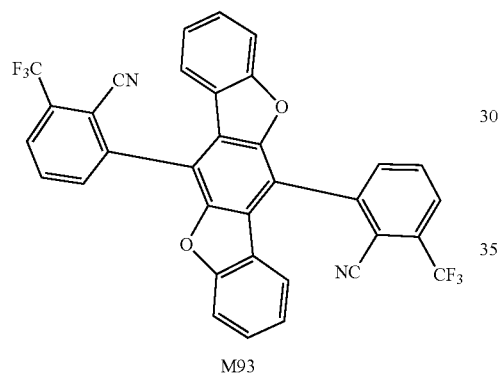

M93

Under nitrogen protection, compound S19 (1.75 mmol), S20 (3.7 mmol), [Pd$_2$(dba)$_3$].CHCl$_3$ (0.1 mmol) and HP(tBu)$_3$.BF$_4$ (0.2 mmol) were added to a 250 mL two-necked flask; then 80 mL of toluene (passing N$_2$ for 15 min in advance to remove oxygen) was injected therein, and then 6 mL of a 1 M K$_2$CO$_3$ aqueous solution (passing N$_2$ for 15 min in advance to remove oxygen) was added dropwise and stirred at room temperature overnight. After the reaction was completed, 45 mL of deionized water was added, and a few drops of 2 M HCl were further added dropwise. The mixture was extracted with dichloromethane, the organic phase was collected, and dried over anhydrous Na$_2$SO$_4$. The dried solution was filtered, and the solvent was removed on a rotary evaporator to obtain a crude product. The crude product was purified by a silica gel column chromatography, and finally purified to obtain the target product M93 (1.2 mmol, yield: 69%).

The structure of M93 was tested: MALDI-TOF-MS (m/z) obtained by Matrix assisted laser desorption ionization time-of-flight mass spectrometry: C$_{34}$H$_{14}$F$_6$N$_2$O$_2$, calculated value: 596.1, found value: 596.3;

Elemental analysis calculated value: C 68.46, H 2.37, F 19.11, N 4.70, O 5.36; found value: C 68.50, H 2.39, F 19.09, N 4.68, O 5.34.

Application Example 1

This application example provides an OLED device, which in sequence includes: a substrate, an ITO anode, a hole injection layer, a first hole transport layer, a second hole transport layer, a light emitting layer, a first electron transport layer, a second electron transport layer, and a cathode (silver electrode).

The preparation of the OLED device includes the following steps:

(1) cutting the glass substrate into a size of 50 mm×50 mm×0.7 mm, sonicating in acetone, isopropanol and deionized water for 30 minutes, respectively, and then exposing to ozone for about 10 minutes for cleaning; mounting the obtained glass substrate with ITO anode to a vacuum deposition apparatus;

(2) vacuum-evaporating the hole injection layer material compound 1 on the ITO anode layer to a thickness of 10 nm under a vacuum degree of 2×10$^{-6}$ Pa;

(3) evaporating compound 2 on the hole injection layer as the first hole transport layer to a thickness of 100 nm;

(4) vacuum-evaporating compound 3 on the first hole transport layer as a second hole transport layer to a thickness of 10 nm;

(5) vacuum-evaporating a layer of light-emitting layer on the second hole transport layer, wherein compound 4 was used as a host material of the light-emitting layer, and compound M15 provided by the present disclosure was used as a doping material (light-emitting material) of the light-emitting layer, the doping ratio was 8% and the thickness was 30 nm;

(6) vacuum-evaporating compound 5 on the light-emitting layer as a first electron transport layer to a thickness of 10 nm;

(7) vacuum-evaporating compound 6 on the first electron transport layer as a second electron transport layer to a thickness of 30 nm;

(8) vacuum-evaporating a silver electrode on the second electron transport layer as a cathode to a thickness of 15 nm.

compound1

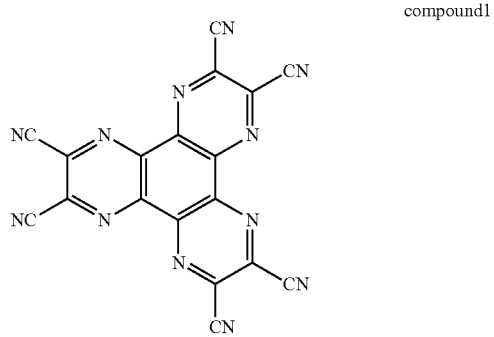

compound2 compound3 compound4 compound5 compound6

Ir(ppy)₃

Ir(piq)₂(acac)

Application Example 2

This application example differs from the application example 1 in that M15 in the step (5) is replaced with an equal amount of M16.

Application Example 3

This application example differs from the application example 1 in that M15 in the step (5) is replaced with an equal amount of M17.

Application Example 4

This application example differs from the application example 1 in that M15 in the step (5) is replaced with an equal amount of M58.

Application Example 5

This application example differs from the application example 1 in that M15 in the step (5) is replaced with an equal amount of M62

Application Example 6

The difference between this application example and application example 1 is that the host material compound 4 in step (5) is replaced with M67 provided by the present disclosure, and the guest material M15 is replaced with a red light emitting material Ir(piq)$_2$(acac).

Application Example 7

The difference between this application example and application example 1 is that the host material compound 4 in step (5) is replaced with M93 provided by the present disclosure, and the guest material M15 is replaced with a green light emitting material Ir(ppy)$_3$.

Comparative Example 1

The difference between this comparative example and application example 1 is that M15 in step (5) is replaced with an equal amount of comparative compound 1.

Comparative Example 2

The difference between this comparative example and application example 1 is that M15 in step (5) is replaced with an equal amount of comparative compound 2.

Comparative Example 3

The difference between this comparative example and application example 1 is that M15 in step (5) is replaced with an equal amount of comparative compound 3.

Comparative Example 4

The difference between this comparative example and application example 1 is that M15 in step (5) is replaced with an equal amount of comparative compound 4.

comparative compound 1

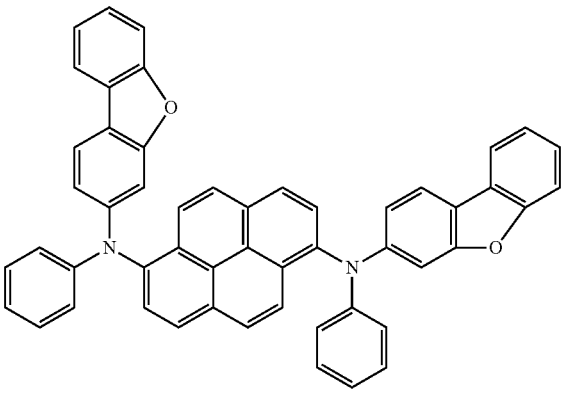

comparative compound 2

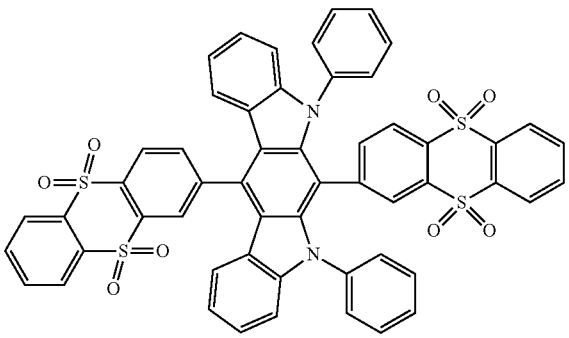

comparative compound 3

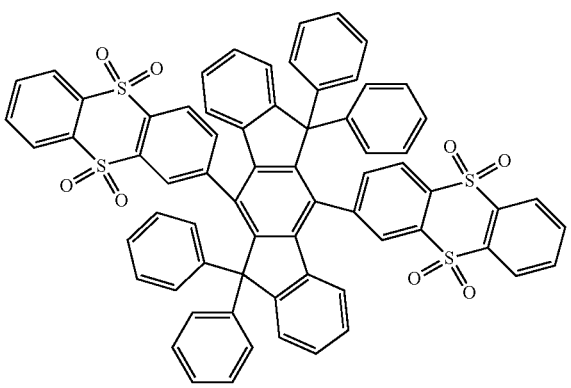

comparative compound 4

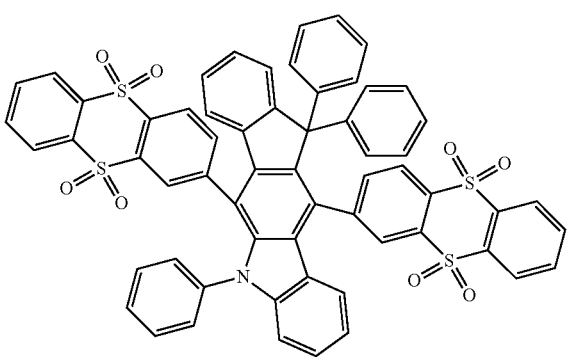

Performance Test:
(1) Simulation Calculation of Compounds:
Using the density functional theory (DFT), for the compounds provided by the present disclosure, the Gaussian 09 program package (Guassian Inc.) was used to optimize and calculate the distribution condition of molecular frontier orbitals HOMO and LUMO at the B3LYP/6-31G (d) calculation level. At the same time, based on the time-dependent density functional theory (TD-DFT), singlet energy level $S_1$ and triplet energy level $T_1$ of a compound molecule were simulated and calculated. The results are shown in Table 1.

TABLE 1

| Compounds | HOMO (eV) | LUMO (eV) | $E_g$ (eV) | $S_1$ (eV) | $T_1$ (eV) | $\Delta E_{ST}$ (eV) |
|---|---|---|---|---|---|---|
| M15 | −5.11 | −2.90 | 2.21 | 1.88 | 1.86 | 0.02 |
| M16 | −5.13 | −2.61 | 2.52 | 2.13 | 2.03 | 0.10 |
| M17 | −5.07 | −2.10 | 2.97 | 2.62 | 2.56 | 0.06 |
| M58 | −5.45 | −2.65 | 2.80 | 2.49 | 2.46 | 0.03 |
| M62 | −5.61 | −2.75 | 2.86 | 2.57 | 2.53 | 0.04 |
| M67 | −5.69 | −2.36 | 3.33 | 2.92 | 2.35 | 0.57 |
| M93 | −6.52 | −2.60 | 3.92 | 3.56 | 2.60 | 0.96 |

It can be concluded from the data in Table 1 that compounds M15, M16, M17, M58, and M62 provided by the present disclosure have lower $\Delta E_{ST}$ (<0.3 eV), obvious thermally activated delayed fluorescent characteristics, and are suitable to be used as high-efficiency luminescent material in a light-emitting layer in an OLED device.

Figure 2:
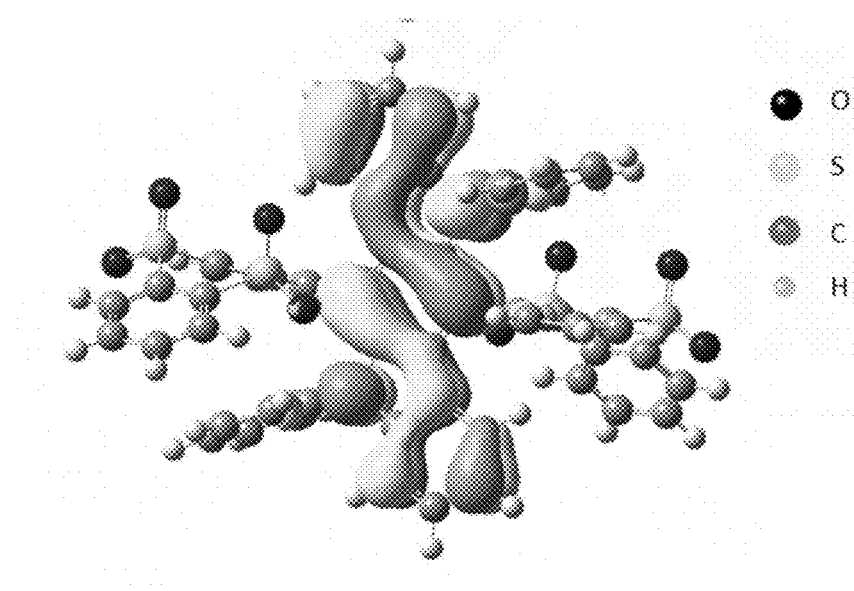
FIG. 2 is a schematic diagram of HOMO distribution of compound M58 provided by the present disclosure.
Figure 3:
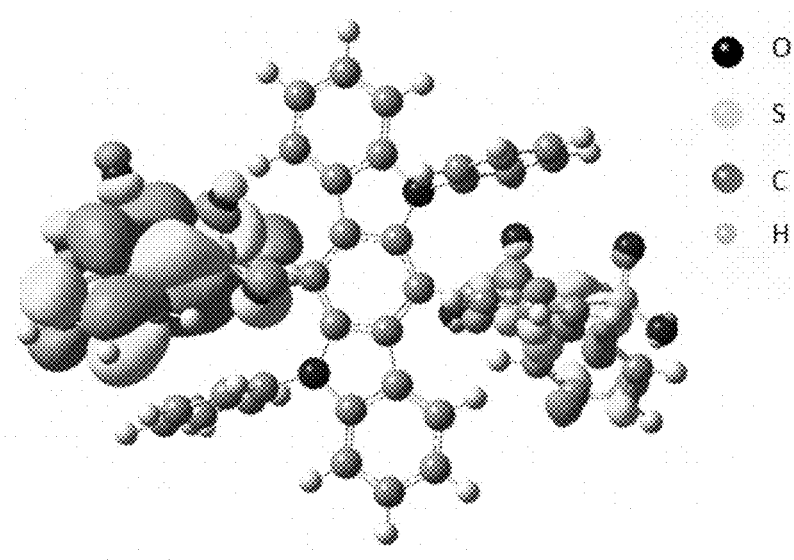
FIG. 3 is a schematic diagram of LUMO distribution of compound M58 provided by the present disclosure.

HOMO and LUMO energy levels of the compounds provided by the present disclosure are calculated by Gaussian simulation, wherein HOMO and LUMO distribution diagrams of compound M58 provided by the present disclosure are shown in FIG. 2 and FIG. 3, respectively. As can be seen from FIGS. 2 and 3, the HOMO and LUMO of M58 have better spatial separation, which helps to reduce $\Delta E_{ST}$.

The compound provided by the present disclosure has a characteristic of bipolarity, which is beneficial to the transport of holes and electrons, meanwhile has appropriate triplet energy levels and singlet energy levels (for example, M67, and M93.), so that the compounds according to the present disclosure can also be used as a host material in a light-emitting layer.

(2) Performance Evaluation of OLED Devices:

Current of the OLED device at different voltages was measured with a Keithley 2365A digital nanovoltmeter, and then current density at different voltages of the OLED device was obtained by dividing the current by the light-emitting area; the OLED device was tested for luminance and radiant energy flux density at different voltages using a Konicaminolta CS-2000 spectroradiometer. According to current density and luminance of the OLED device at different voltages, working voltage ($V_{on}$) and current efficiency (Cd/A) at the same current density (10 mA/cm$^2$) were obtained; lifetime T95 was obtained by measuring the time when brightness of the OLED device reached 95% of the initial brightness (under 500 nit test conditions); test datas are shown in Table 2.

TABLE 2

| OLED device | Light-emitting material | $V_{on}$(V) | Current efficiency (Cd/A) | Lifetime T95(h) |
|---|---|---|---|---|
| Application example 1 | M15 | 3.36 | 18.8 | 78 |
| Application example 2 | M16 | 3.28 | 16.8 | 92 |
| Application example 3 | M17 | 3.25 | 16.0 | 86 |
| Application example 4 | M58 | 3.85 | 15.2 | 45 |
| Application example 5 | M62 | 3.76 | 15.6 | 43 |
| Comparative Example 1 | Comparative Compound 1 | 4.30 | 7.5 | 40 |
| Comparative Example 2 | Comparative Compound 2 | 4.02 | 12.8 | 38 |
| Comparative Example 3 | Comparative Compound 3 | 3.96 | 8.2 | 46 |
| Comparative Example 4 | Comparative Compound 4 | 3.92 | 10.6 | 42 |

It can be obtained from the data in Table 2 that in the application examples 1 to 5, the OLED device prepared based on the compound provided by the present disclosure as a guest material of the light-emitting layer has achieved good device performance, has excellent luminous efficiency, and long working life of the device. The OLED devices provided in the application examples 1 to 5 of the present disclosure have an operating voltage lower than 3.9 V, a current efficiency of 15.2 to 18.8 cd/A, and a lifetime T95 higher than 43 h, or even up to 92 h.

Compared with the comparative device (Comparative Example 1) using classic blue fluorescent material comparative compound 1 as a fluorescent dopant, current efficiency CE of devices using compounds M17, M58, and M62 provided by the present disclosure as the blue light guest materials is significantly higher than that of the device in Comparative Example 1, this is mainly benefit from TADF characteristics of the compound per se of the present disclosure, which has a lower $\Delta E_{ST}$ (<0.3 eV), and there is an efficient photophysical process of reverse intersystem crossing between the singlet and triplet states. Triplet excitons forbidden by traditional fluorescent molecules (e.g., BCzVBi) can be used to emit light, thereby improving the efficiency of the device, and in turn improving working life of the device.

Compared with Comparative Compound 2, Comparative Compound 3, and Comparative Compound 4, the compound M58 provided by the present disclosure has the highest luminous efficiency. As can be seen from the molecular chemical structure, the two N atoms of Comparative Compound 2 face the same direction. The electron accepting group on the side far from the N atom cannot form a sufficient space charge transfer function with the core unit indolocarbazole, and cannot effectively achieve dual emission nuclei, which reduces luminous efficiency. Comparative Compound 3 and Comparative Compound 4 differ from compound M58 of the present disclosure in that one or two N atoms in M58 are replaced with a C atom, which reduces properties of the electron donor of the entire molecule and reduces charge transfer effect between electron donors and the electron acceptors, causing TADF effect of the entire molecule and luminous efficiency to decrease.

In conclusion, based on molecular structure design, in the compound provided by the present disclosure, D-A charge transfer effect forms through chemical bonds, and due to space distance design between electron donor and electron acceptor, a space charge transfer effect forms, so that HOMO and LUMO can form an effective separation in the molecule, reducing $\Delta E_{ST}$, enabling an energy level difference $\Delta E_{st} = E_{S1} - E_{T1} \leq 0.30$ eV, and realizing an efficient physical process of reverse intersystem crossing, so that the compound has typical TADF characteristics; the compound provided by the present disclosure can have two D-A light-emitting sub-units in one molecule, which have the property of a double emission nucleus, effectively improving oscillator strength and luminous efficiency; at the same time, the bipolar characteristics of the compound are conducive to transporting electrons and holes. Therefore, the compound provided by the present disclosure is highly suitable as a material for a light-emitting layer of an OLED device, widens the light-emitting layer, and improves luminous efficiency and working life of the OLED device.

At the same time, the compounds provided by the present disclosure also have bipolar properties and good transport properties for both holes and electrons. They can also be used as host material of light-emitting layer, widening light-emitting area, improving luminous efficiency and working life of a device. Performance test results of an OLED device using the compound provided by the present disclosure as host material of the light emitting layer are shown in Table 3.

TABLE 3

| OLED device | Host material | Light-emitting material | $V_{on}(V)$ | Current efficiency (Cd/A) | Lifetime T95(h) |
|---|---|---|---|---|---|
| Application example 6 | M67 | Ir(piq)$_2$(acac) | 3.64 | 16.6 | 128 |
| Application example 7 | M93 | Ir(ppy)$_3$ | 3.65 | 65 | 75 |

As can be seen from the data in Table 3 that OLED devices using compounds M67 and M93 provided by the present disclosure as phosphorescent host materials also have high current efficiency, long lifetime of device, and low operating voltage. This is because the compounds provided by the present disclosure have bipolar properties and have good transport properties for both holes and electrons. They can widen light-emitting area, improve luminous efficiency and working life of the device. It can be seen that the compounds of the present disclosure are also suitable as green and red phosphorescent host materials.

Applicant has stated that although the present disclosure illustrates the compound of the present disclosure and a display panel and an electronic device including the compound through the above examples, the present disclosure is not limited to the above processing steps, that is to say, it is not meant that the present disclosure has to be implemented depending on the above processing steps. It will be apparent to those skilled in the art that any improvements made to the present disclosure, equivalent replacements and addition of adjuvant ingredients to the raw materials selected in the present disclosure, and selections of the specific implementations, all fall within the protection scope and the disclosure scope of the present disclosure.

What is claimed is:
1. A compound, comprising a structure as shown in Formula I:

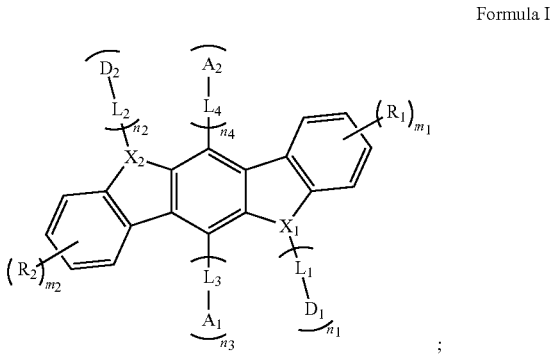

Formula I wherein each of $n_1$ and $n_2$ is independently set as 0 or 1, and each of $n_3$ and $n_4$ is independently set as 1;
wherein $X_1$ and $X_2$ each is independently selected from O, S or N;
when $X_1$ is O or S, $n_1$ is 0;
when $X_2$ is O or S, $n_2$ is 0;
wherein $D_1$ and $D_2$ each represents one donor in an electron-donating group, and is independently selected from any one of a C1 to C20 alkoxyl group, a substituted or unsubstituted C6 to C40 aryl group, a substituted or unsubstituted C3 to C40 heteroaryl group, and a substituted or unsubstituted C6 to C40 arylamine group;
wherein $L_1$, $L_2$, $L_3$ and $L_4$ each is independently selected from any one of a single bond, a C1 to C20 linear or branched alkylene group, a substituted or unsubstituted C6 to C30 arylene group, and a substituted or unsubstituted C3 to C30 heteroarylene group;
wherein $A_1$ and $A_2$ represent an electron-accepting group and each is independently selected from any one of a cyano group, a cyano-substituted C6 to C30 aromatic hydrocarbon group, a cyano-substituted C3 to C30 heteroaryl group, a substituted or unsubstituted C6 to C30 arylboron group, a substituted or unsubstituted C6 to C40 aryl keto group, a substituted or unsubstituted C4 to C40 heteroaryl keto group, a substituted or unsubstituted C6 to C30 arylsulfone group, and a substituted or unsubstituted C6 to C30 arylphosphonoxy group;
wherein when a substituent exists in the above groups, the substituent is selected from at least one of a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen; and
wherein $m_1$ and $m_2$ are both 0,
wherein the substituted or unsubstituted C6 to C40 aryl keto group or the substituted or unsubstituted C4 to C40 heteroaryl keto group is selected from any one of the following groups:

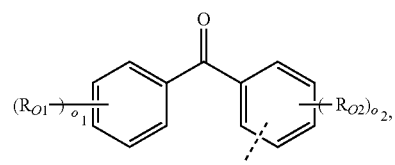

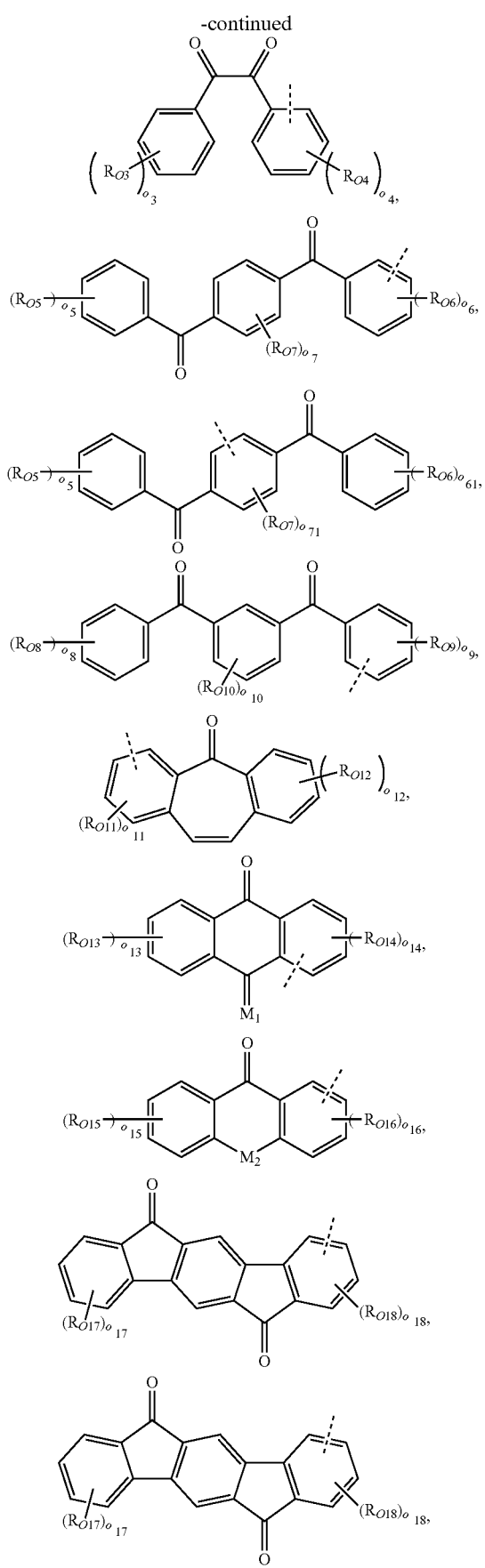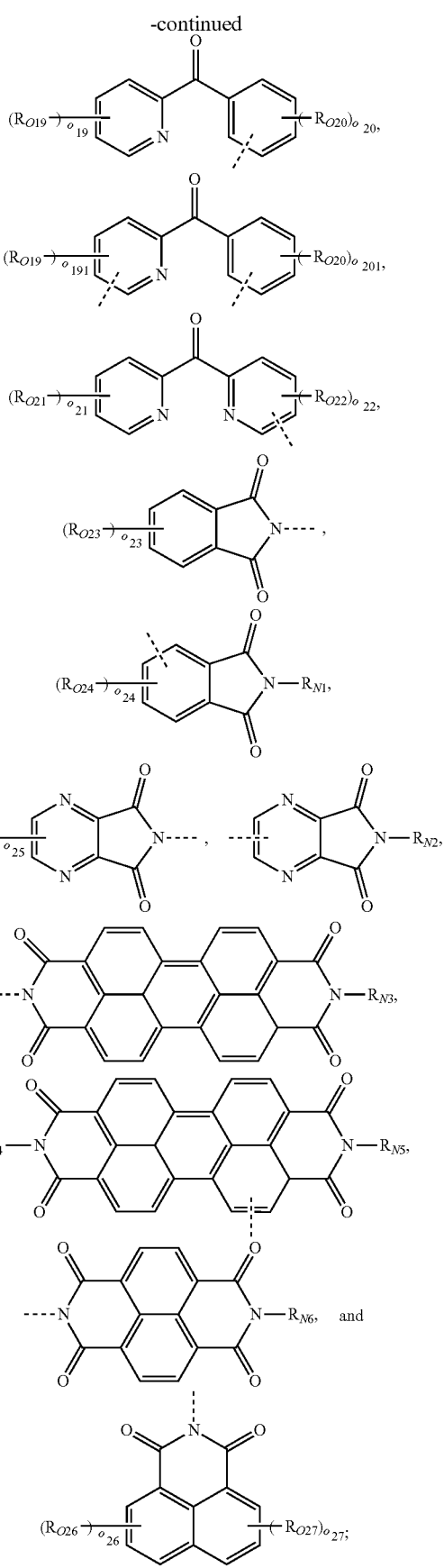

wherein, dotted line represents linking position of a group;

wherein $R_{O1}$-$R_{O26}$ each is independently selected from any one of a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen;

wherein $M_1$ is an oxygen atom (O) or a surfer atom (S);

wherein $M_2$ is selected from O, S or $R_{M1}$—C—$R_{M2}$, and $R_{M1}$ and $R_{M2}$ each is independently selected from any one of hydrogen, a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen;

wherein $R_{N1}$-$R_{N6}$ each is independently selected from any one of hydrogen, a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen;

wherein:

$o_1$, $o_3$, $o_5$, $o_{61}$, $o_8$, and $o_{201}$ each is independently an integer of 0 to 5;

$o_2$, $o_4$, $o_6$, $o_7$, $o_9$, $o_{10}$, $o_{12}$, $o_{13}$, $o_{15}$, $o_{17}$, $o_{19}$, $o_{20}$, $o_{21}$, and $o_{23}$ each is independently an integer of 0 to 4;

$o_{71}$, $o_{11}$, $o_{14}$, $o_{16}$, $o_{18}$, $o_{191}$, $o_{22}$, $o_{24}$, $o_{26}$, and $o_{27}$ each is independently an integer of 0 to 3; and $o_{25}$ is an integer of 0 to 2.

2. The compound according to claim 1, wherein the cyano-substituted C6 to C30 aromatic hydrocarbon group and the cyano-substituted C3 to C30 heteroaryl group are selected from any one of the following groups:

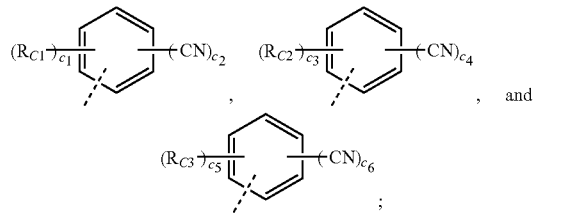

wherein, dotted line represents linking position of a group;

wherein $R_{C1}$, $R_{C2}$ and $R_{C3}$ each is independently selected from at least one of an unsubstituted or halogenated C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen;

and wherein:

$c_1$ is an integer of 0 to 4, $c_2$ is an integer of 1 to 3, and $c_1+c_2 \leq 5$;

$c_3$ is an integer of 0 to 3, $c_4$ is an integer of 1 to 3, and $c_3+c_4 \leq 4$; and $c_5$ is an integer of 0 to 2, $c_6$ is an integer of 1 to 3 and $c_5+c_6 \leq 3$.

3. The compound according to claim 2, wherein the cyano-substituted C6 to C30 aromatic hydrocarbon group and the cyano-substituted C3 to C30 heteroaryl group are selected from any one of the following groups:

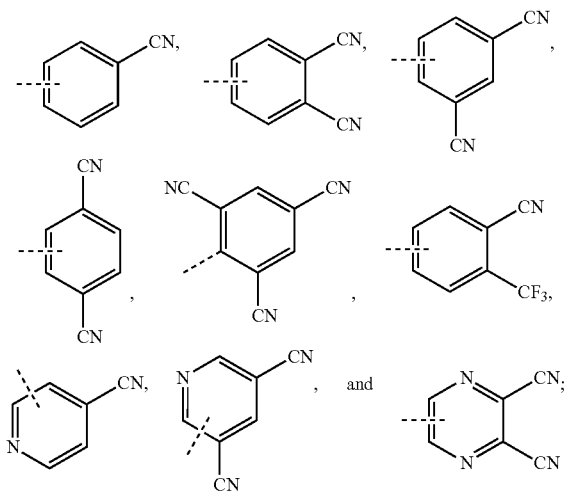

wherein, dotted line represents linking position of a group.

4. The compound according to claim 1, wherein the C6 to C30 arylboron group is selected from any one of the following groups:

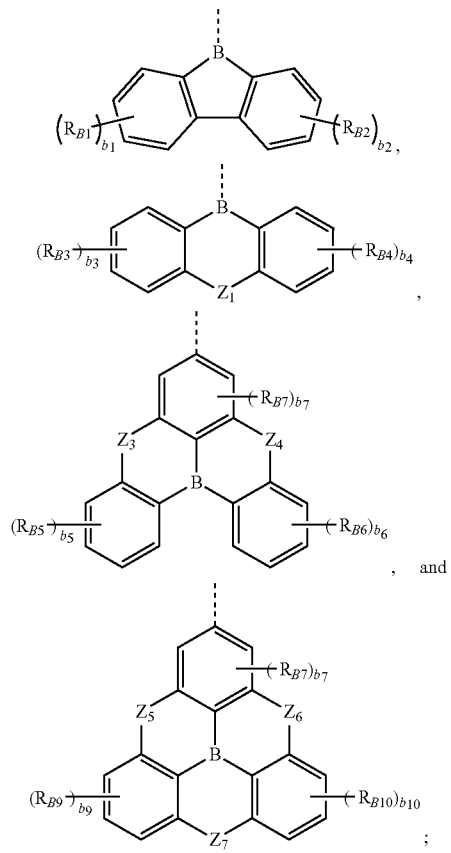

wherein, dotted line represents linking position of a group;

wherein $R_{B1}$-$R_{B10}$ each is independently selected from any one of a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen;

wherein $Z_1$-$Z_7$ each is independently selected from O, S, N—$R_{Z1}$ or B—$R_{Z2}$, $R_{Z1}$ and $R_{Z1}$ each is independently selected from any one of hydrogen, a C6 to C40 aryl group, a C1 to C10 linear or branched alkyl group, a C1 to C20 alkoxyl group, a C3 to C20 cycloalkyl group, a C3 to C20 heterocycloalkyl group, and a C3 to C40 heteroaryl group; and wherein:

$b_1$-$b_6$ each is independently an integer of 0 to 4;

$b_7$ and $b_8$ each is independently an integer of 0 to 2; and $b_9$ and $b_{10}$ each is independently an integer of 0 to 3.

5. The compound according to claim 4, wherein the C6 to C30 arylboron group is selected from any one of the following groups:

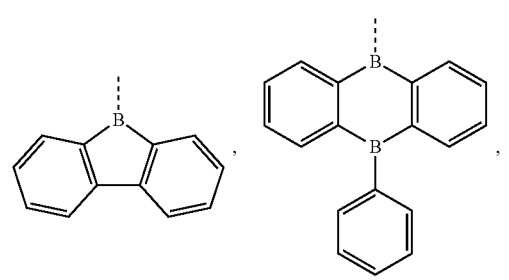

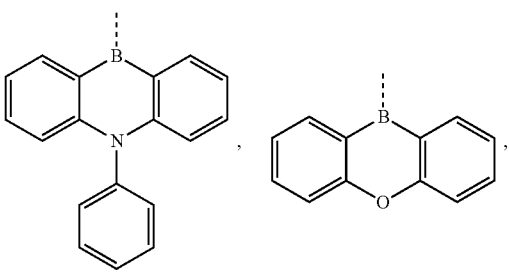

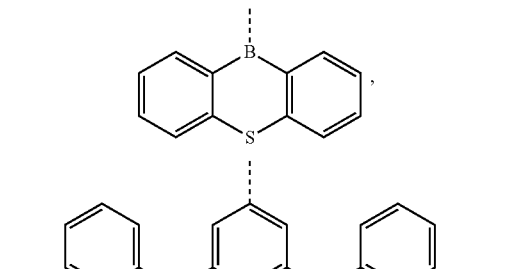

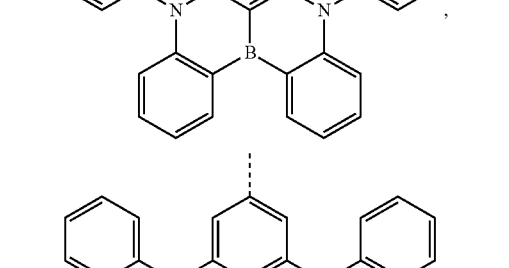

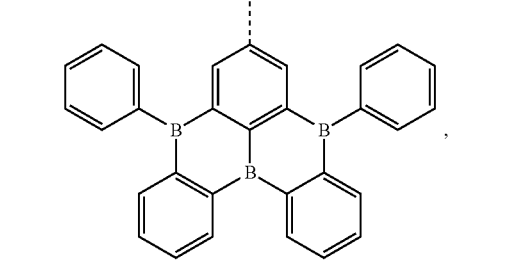

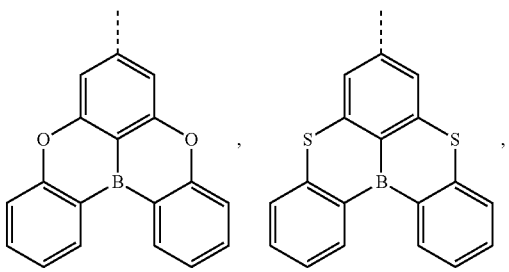

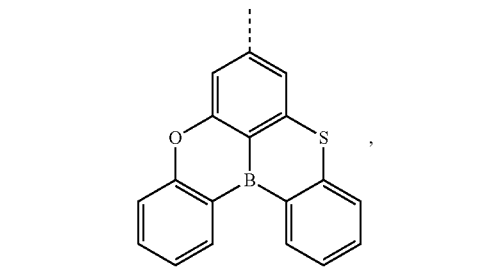

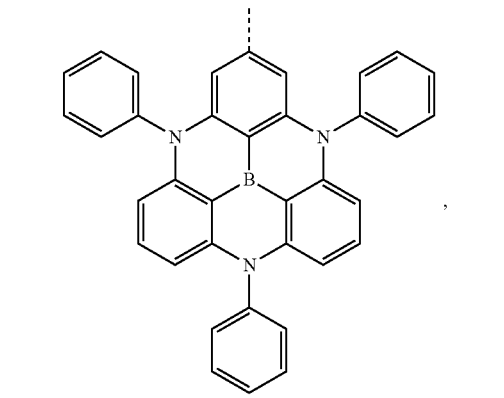

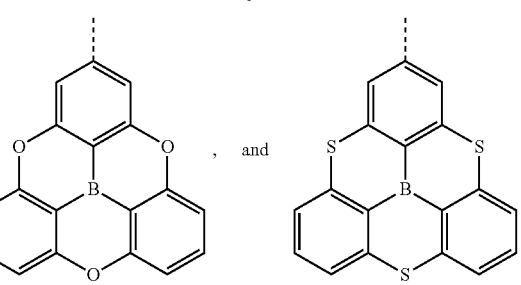

wherein, dotted line represents linking position of a group.

6. The compound according to claim 1, wherein the C6 to C40 aryl keto group and the substituted or unsubstituted C4 to C40 heteroaryl keto group are selected from any one of the following groups:

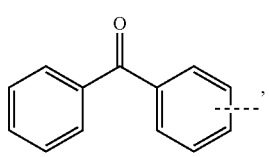

103
-continued
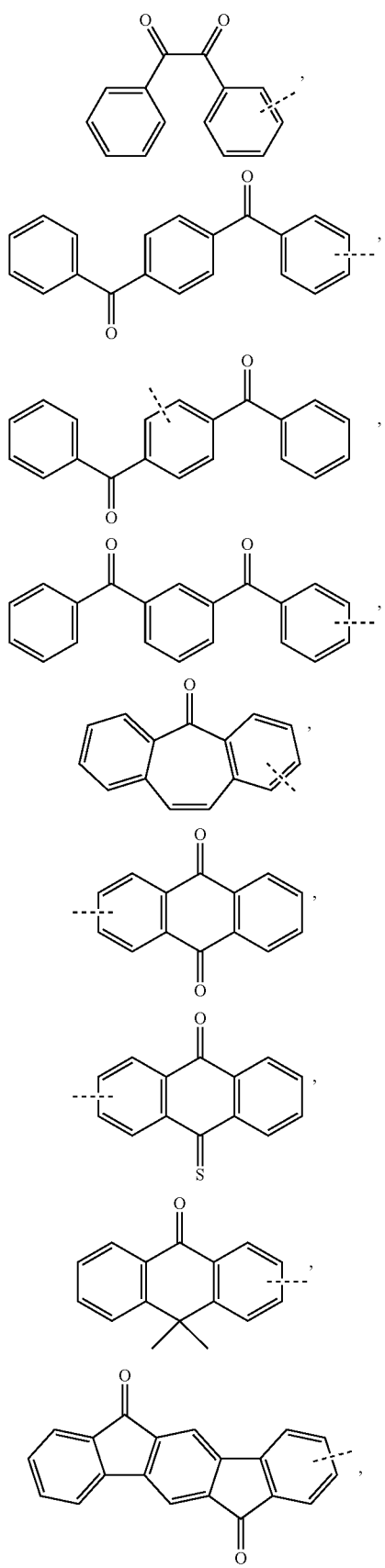
104
-continued
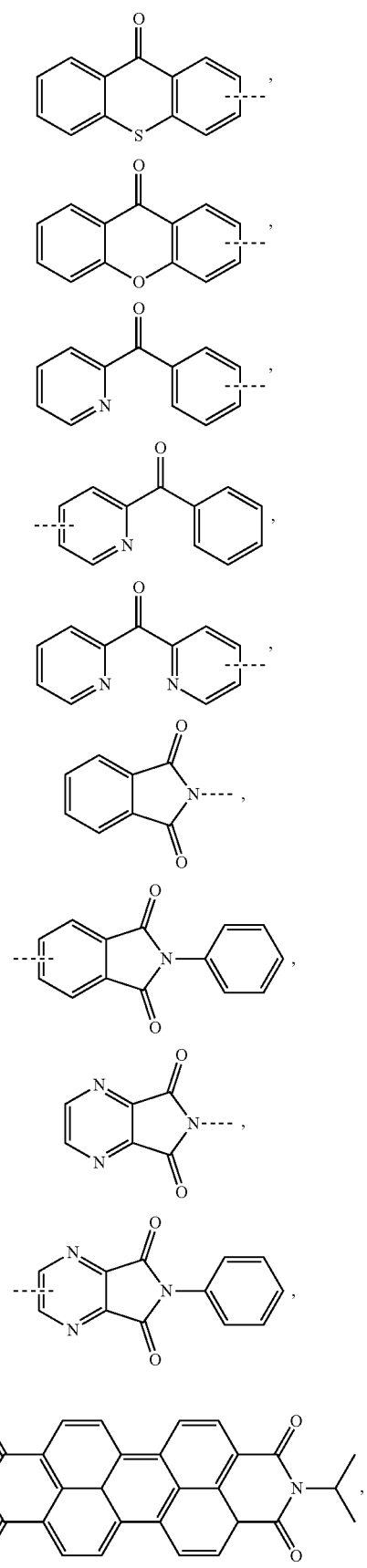

-continued

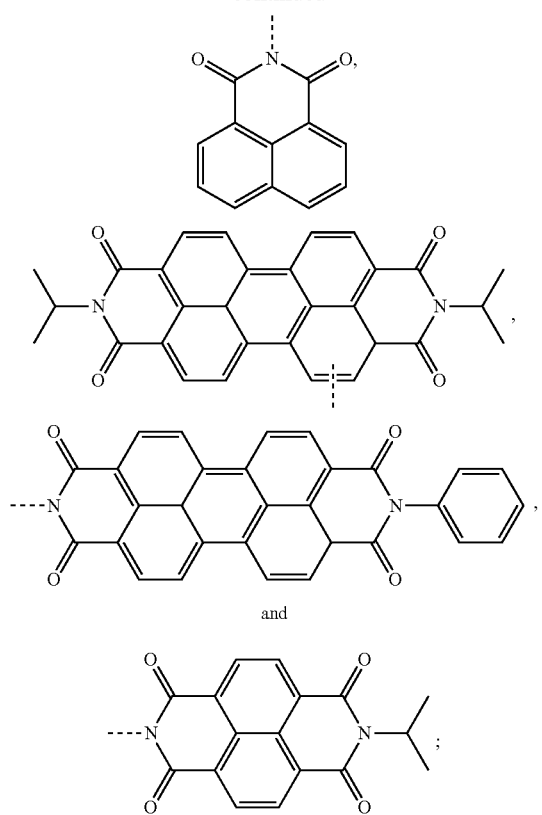

and wherein, dotted line represents linking position of a group.

7. The compound according to claim 1, wherein the C6 to C30 arylsulfone group is selected from any one of the following groups:

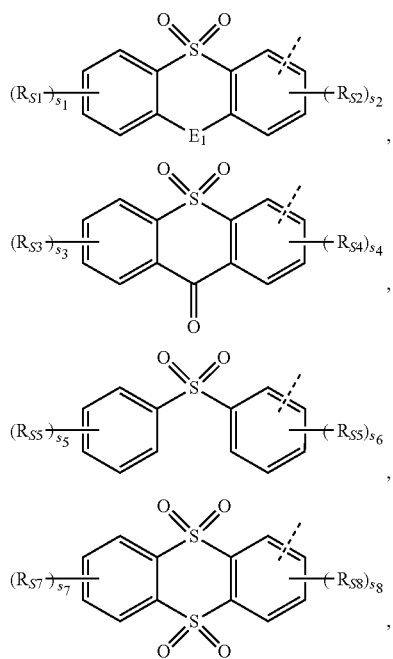

-continued

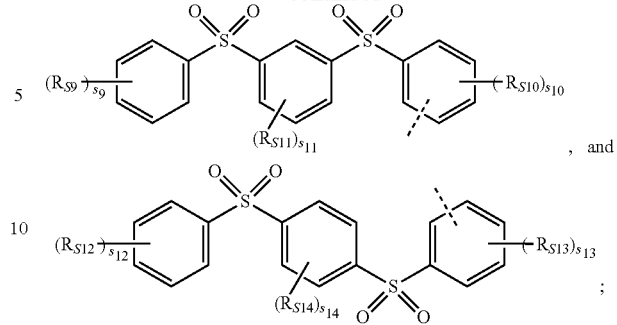

, and wherein, dotted line represents linking position of a group;
wherein $R_{S1}$-$R_{S14}$ each is independently selected from any one of a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen;
wherein $E_1$ is selected from O, S or $R_{E1}$—C—$R_{E2}$, and $R_{E1}$ and $R_{E2}$ each is independently selected from any one of hydrogen, a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen; and wherein:
$s_1$, $s_3$, $s_6$, $s_7$, $s_{10}$, $s_{11}$, $s_{13}$, and $s_{14}$ each is independently an integer of 0 to 4;
$s_2$, $s_4$, and $s_8$ each is independently an integer of 0 to 3; and
$s_5$, $s_9$, and $s_{12}$ each is independently an integer of 0 to 5.

8. The compound according to claim 1, wherein the C6 to C30 arylphosphonoxy group is selected from any one of the following groups:

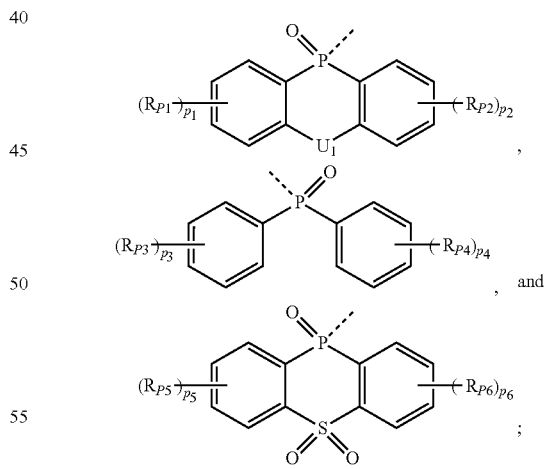

wherein, dotted line represents linking position of a group;
wherein $R_{P1}$-$R_{P6}$ each is independently selected from any one of a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen;
wherein $U_1$ is selected from O, S, N—$R_{U1}$, B—$R_{U2}$ or $R_{U3}$—C—$R_{U4}$, and wherein $R_{U1}$-$R_{U4}$ each is independently selected from any one of hydrogen, a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen; and wherein:

$p_1$, $p_2$, $p_5$, and $p_6$ each is independently an integer of 0 to 4; and $p_3$ and $p_4$ each is independently an integer of 0 to 5.

9. The compound according to claim 1, wherein $X_1$ and $X_2$ are both N, and $n_1$ and $n_2$ are both 1.

10. The compound according to claim 1, wherein $D_1$ and $D_2$ each is independently selected from any one of the following groups:

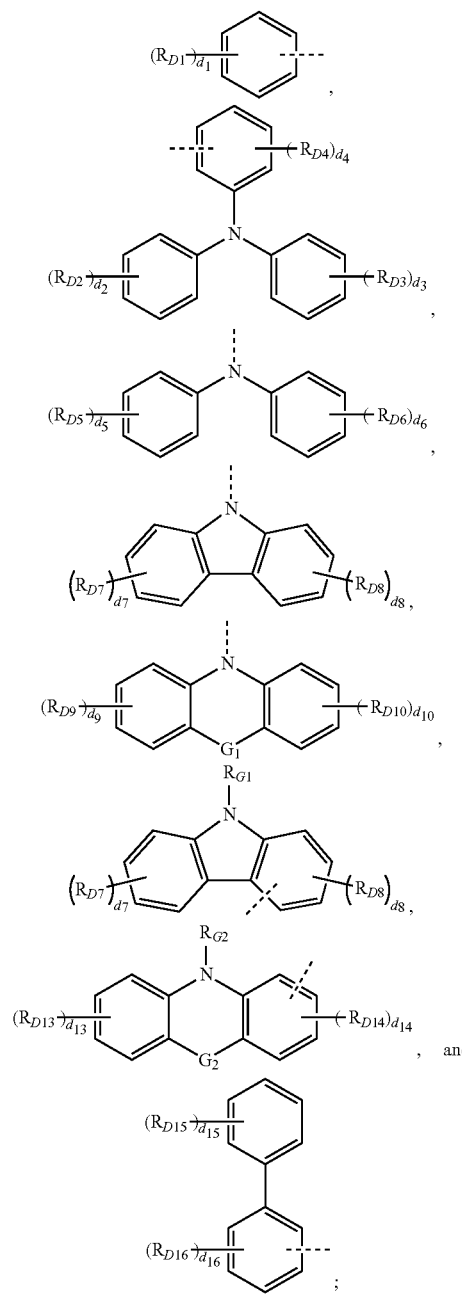

wherein, dotted line represents linking position of a group;

$R_{D1}$-$R_{D16}$ each is independently selected from any one of a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen;

$G_1$ and $G_2$ each is independently selected from O, S, N—$R_{G3}$ or $R_{G4}$—C—$R_{G5}$;

$R_{G1}$-$R_{G5}$ each is independently selected from any one of hydrogen, a C1 to C10 linear or branched alkyl group, a C6 to C20 aryl group, a C6 to C20 heteroaryl group, a C1 to C10 alkoxyl group, a C6 to C20 arylamino group, a C3 to C20 cycloalkyl group, and halogen;

$d_1$, $d_2$, $d_3$, $d_5$, $d_6$, and $d_{15}$ each is independently an integer of 0 to 5;

$d_4$, $d_7$, $d_8$, $d_9$, $d_{10}$, $d_{11}$, $d_{13}$, and $d_{16}$ each is independently an integer of 0 to 4;

$d_{12}$ and $d_{14}$ each is independently an integer of 0 to 3.

11. The compound according to claim 10, wherein the $D_1$ and $D_2$ each is independently selected from any one of the following groups:

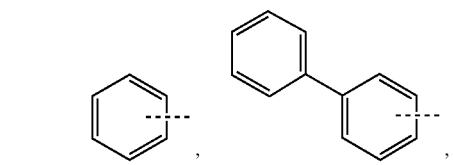

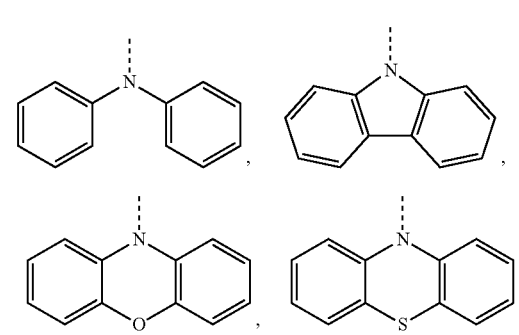

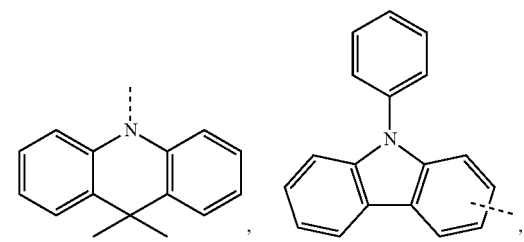

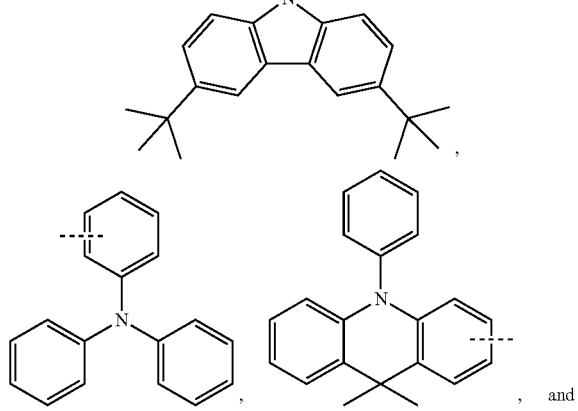, 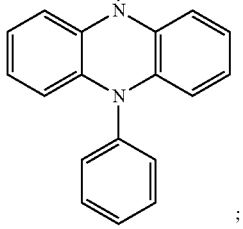 ;
wherein, dotted line represents linking position of a group.
12. The compound according to claim 1, wherein $L_1$, $L_2$, $L_3$ and $L_4$ each is independently selected from a single bond or a C6 to C20 arylene group.
13. The compound according to claim 1, wherein the compound is selected from any one of the following compounds M1, M3 to M75, and M78 to M134:
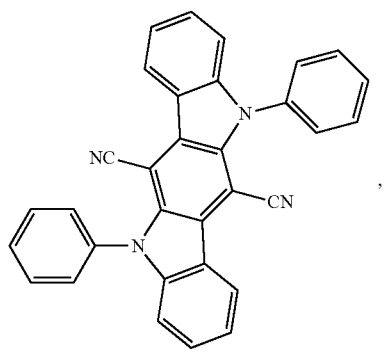
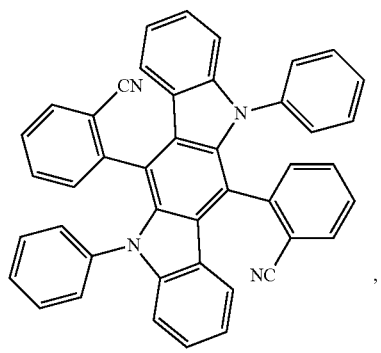 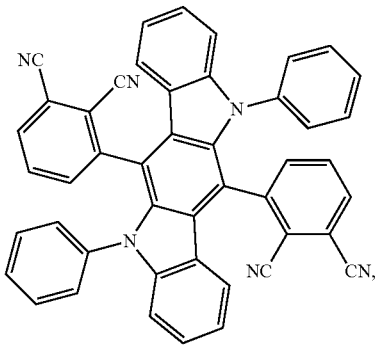
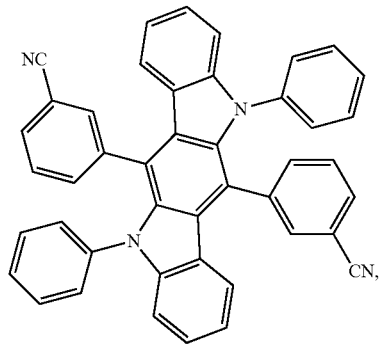 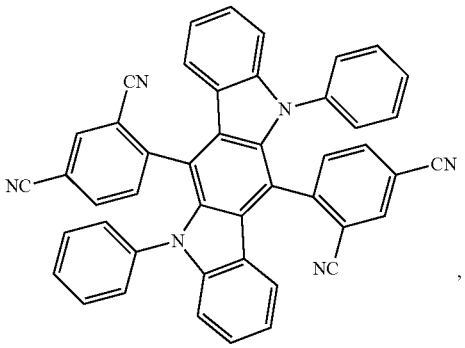

-continued
M7
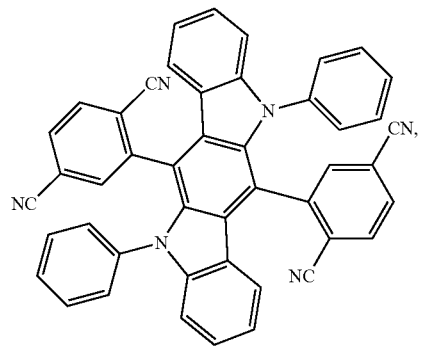
M8
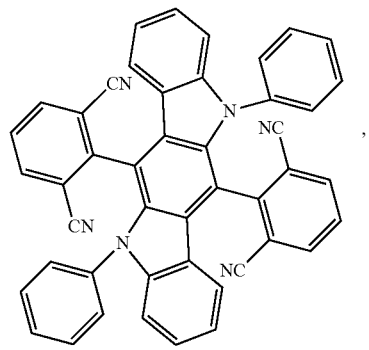
M9
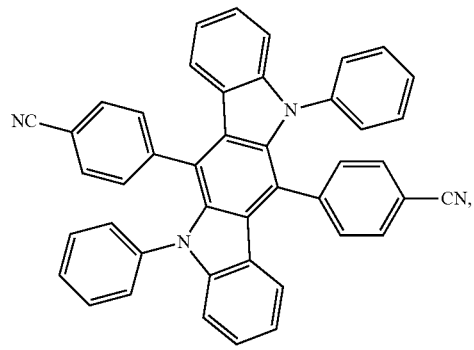
M10
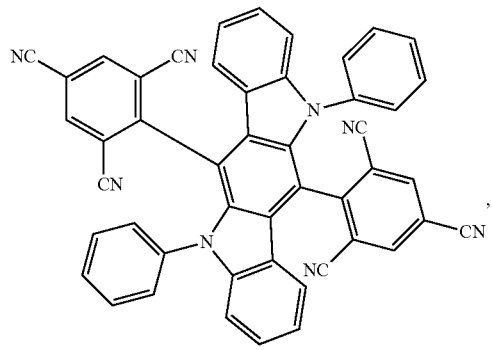
M11
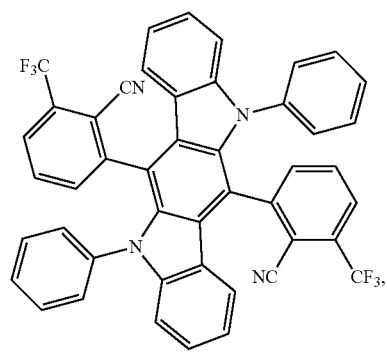
M12
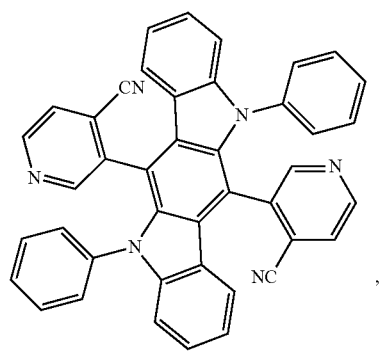
M13
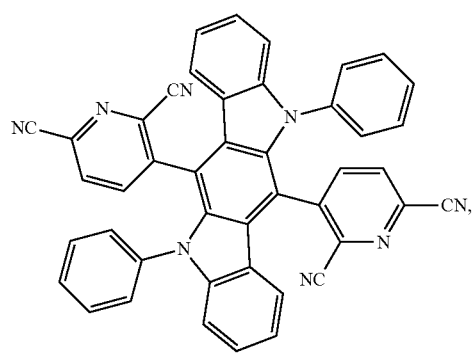
M14
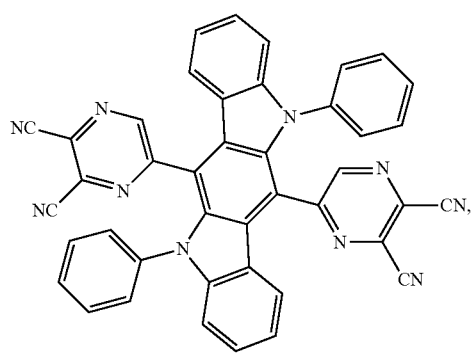

-continued
M15
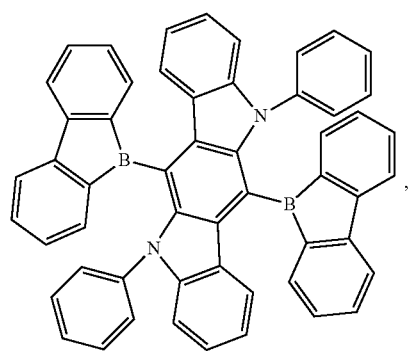
M16
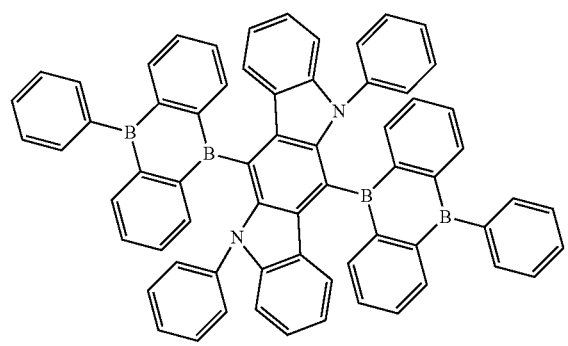
M17
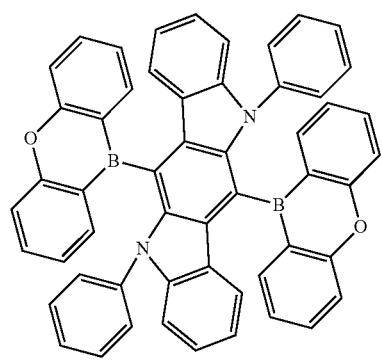
M18
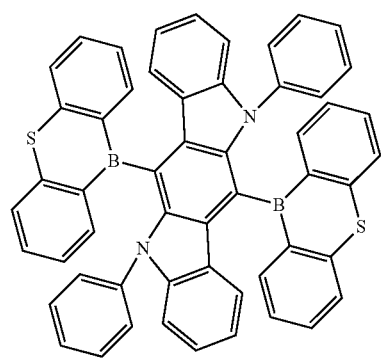
M19
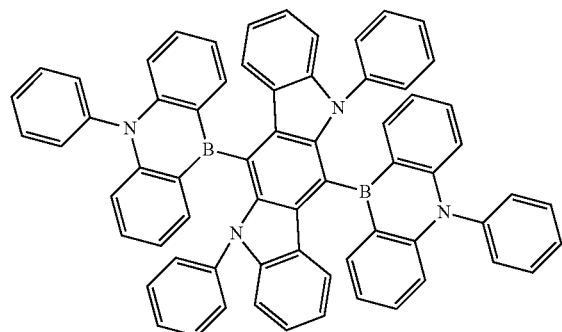
M20
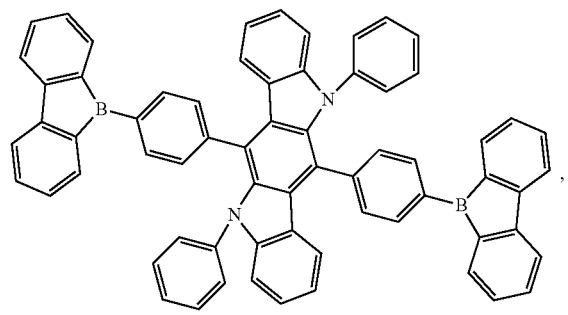
M21
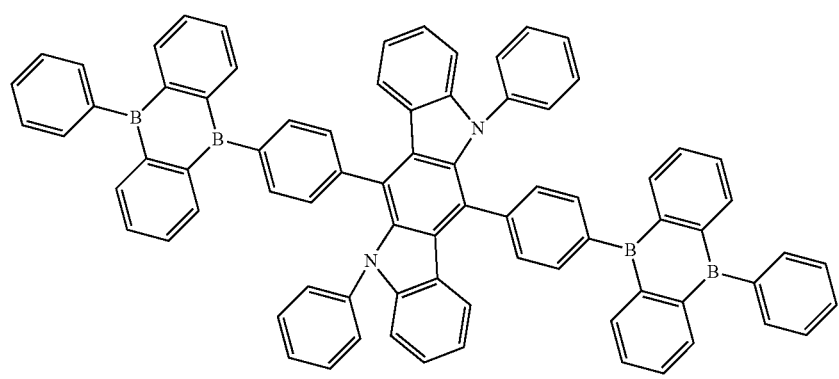

-continued
M26
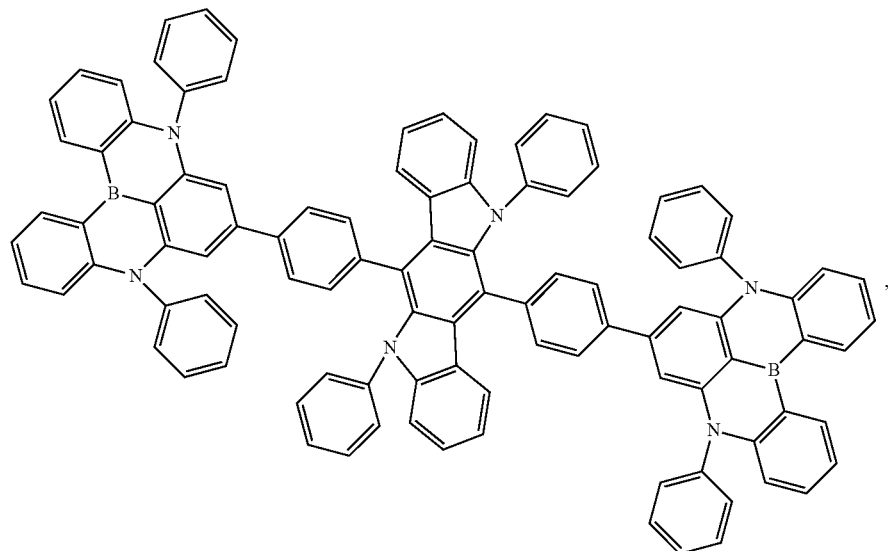
M27
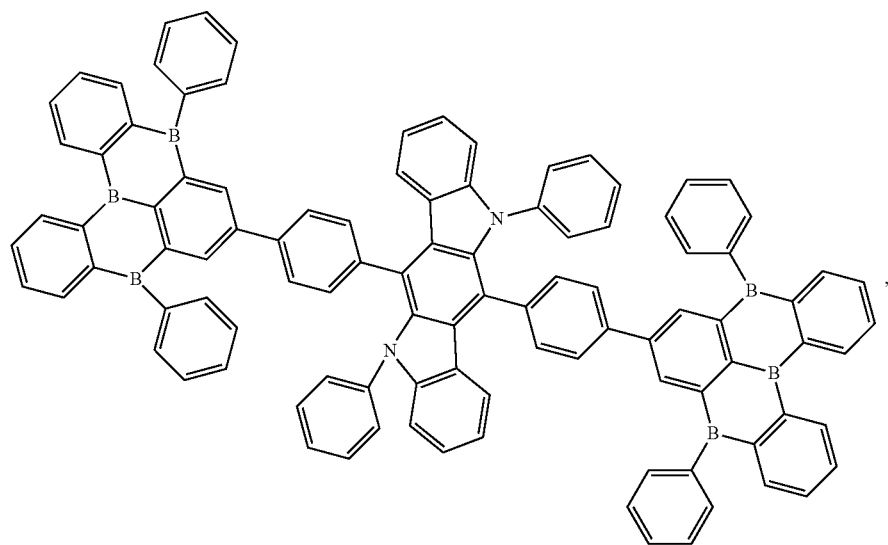
M28
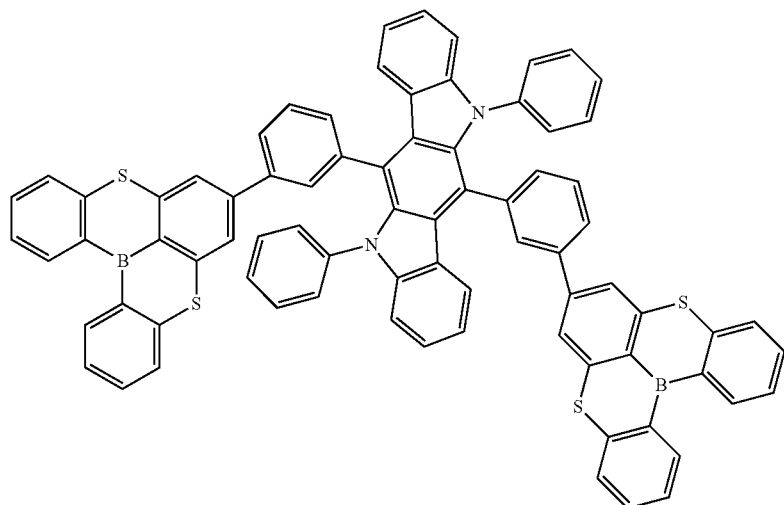

-continued
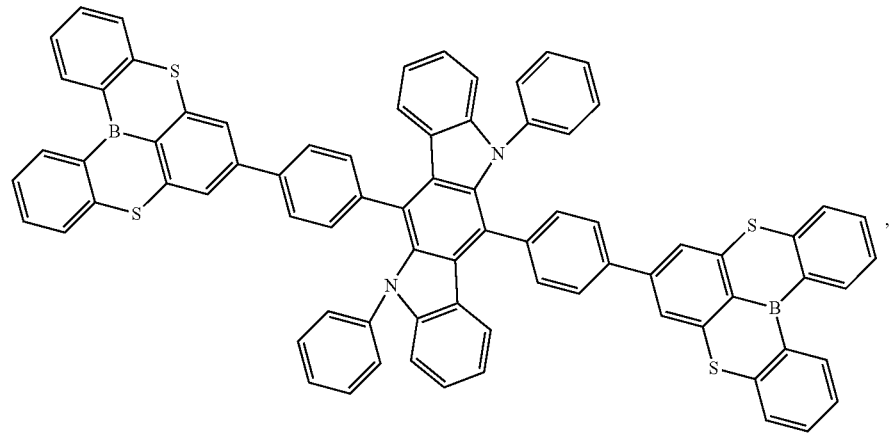
M29
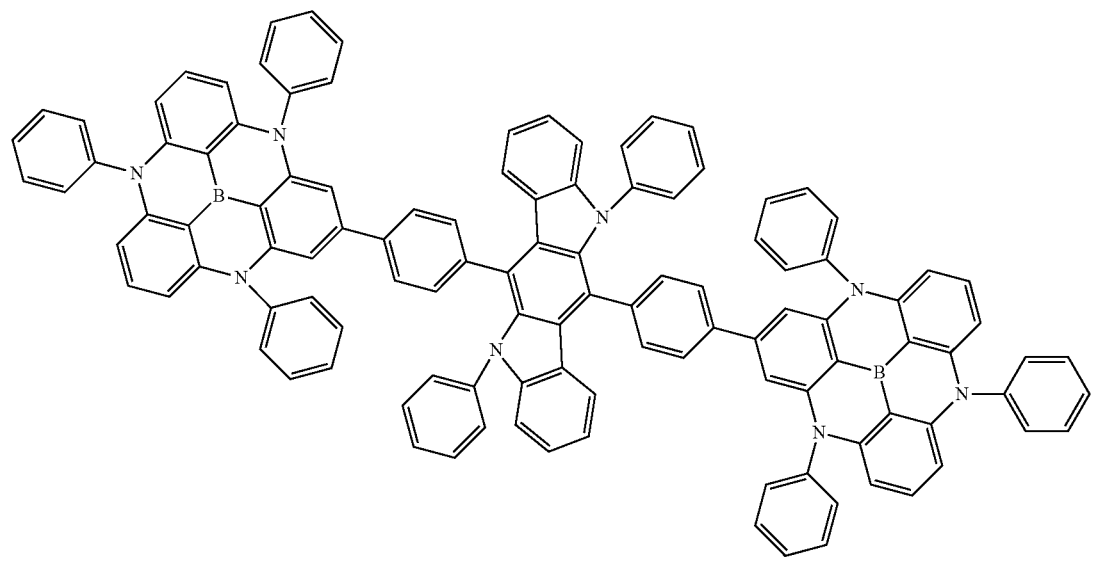
M30
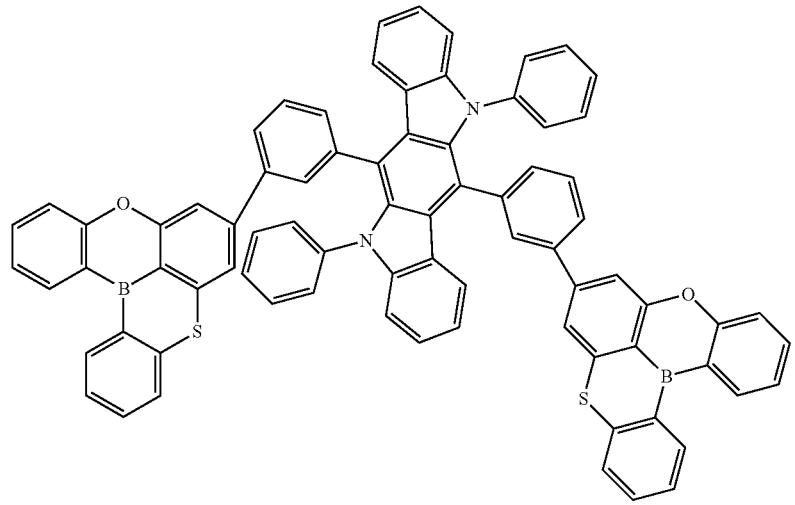
M31

-continued
M32
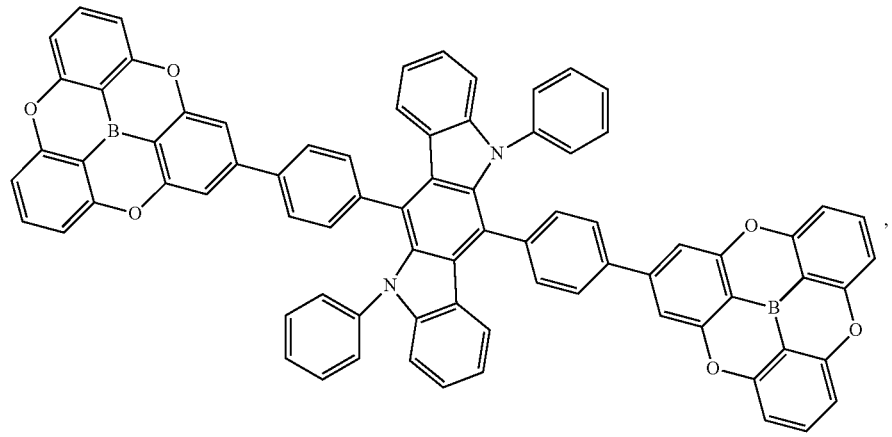
M33
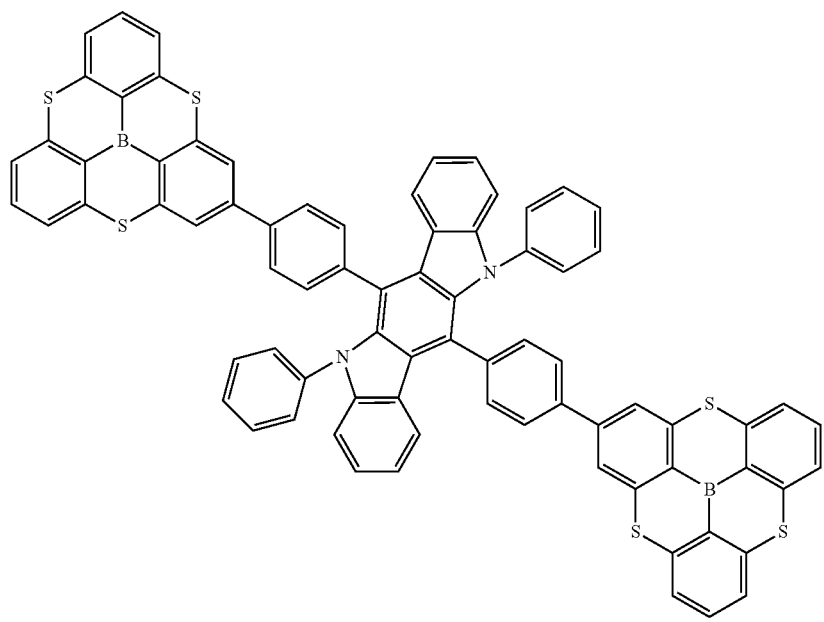
M34
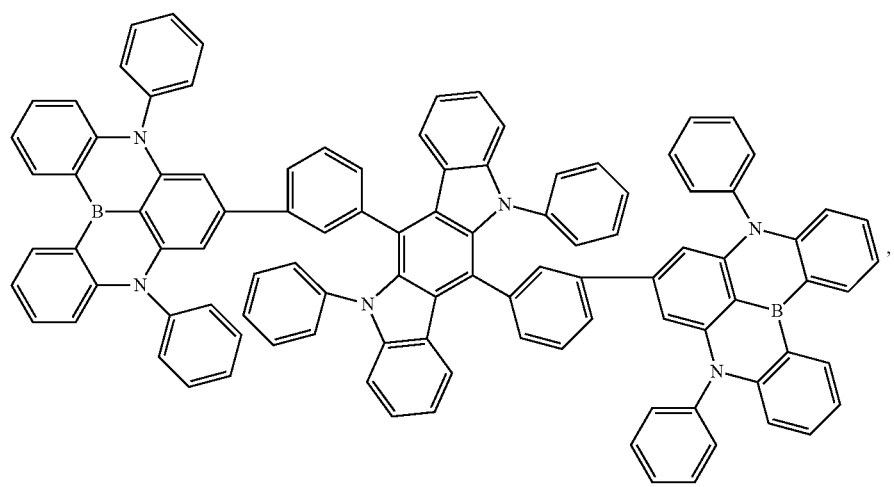

-continued
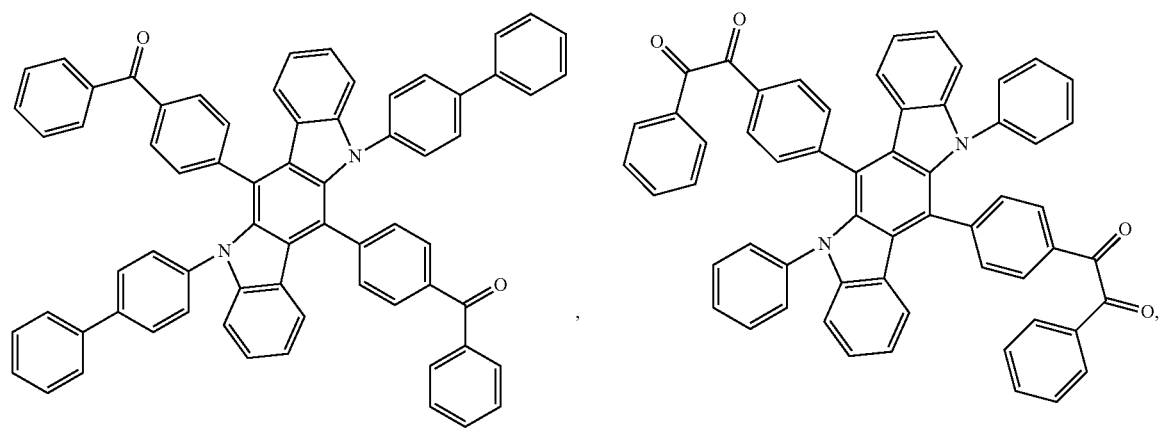
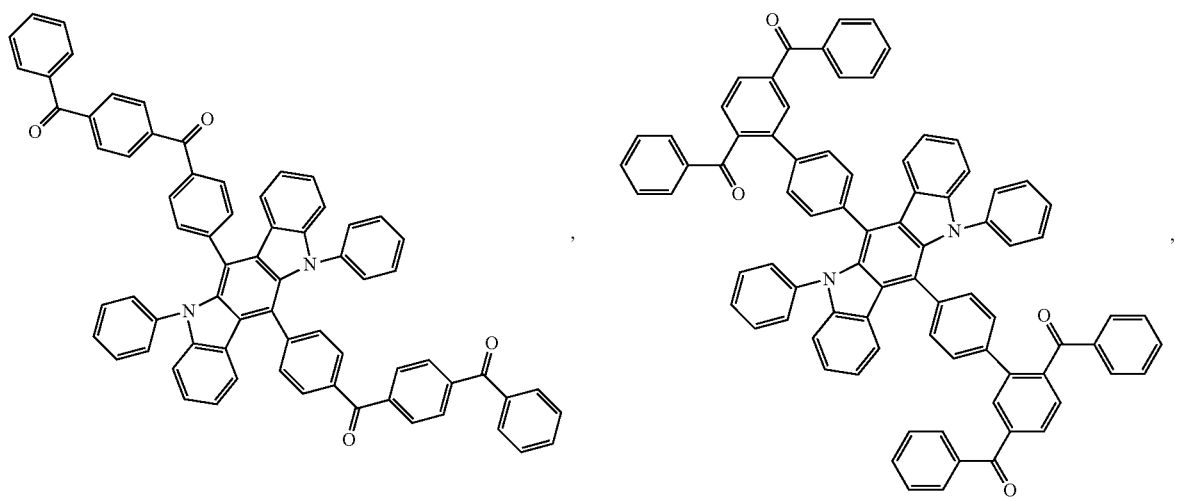
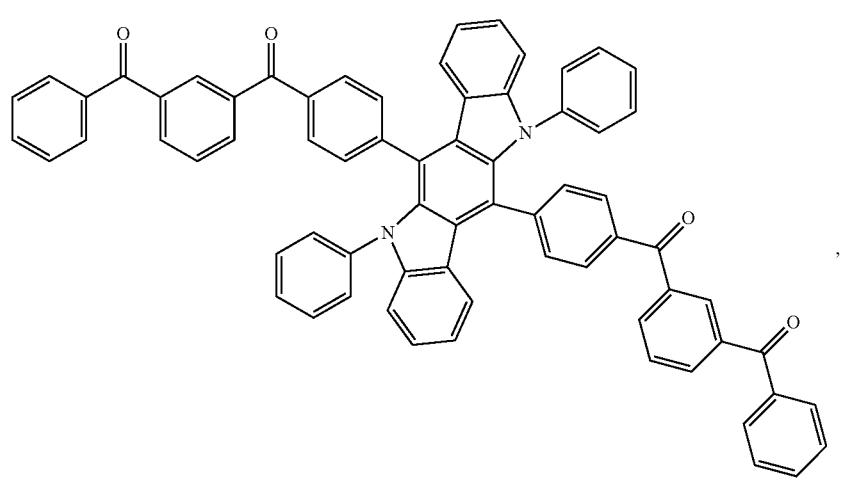

-continued
M40
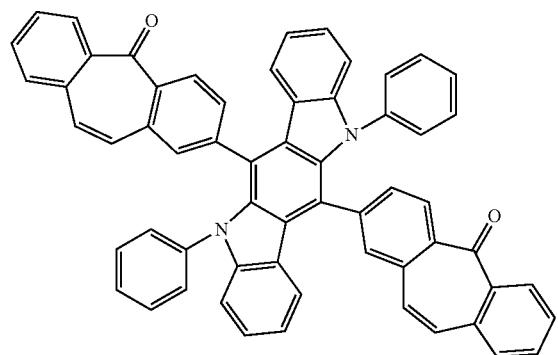
M41
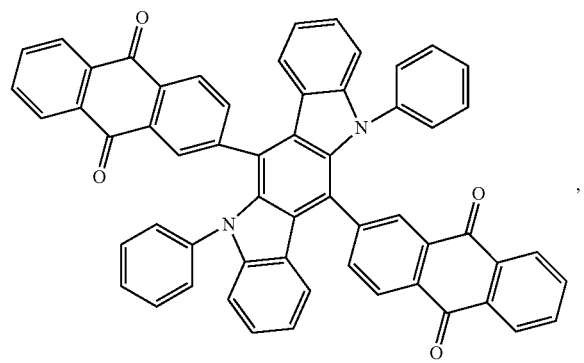
M42
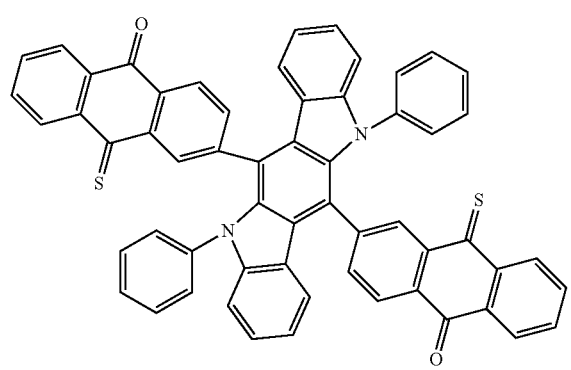
M43
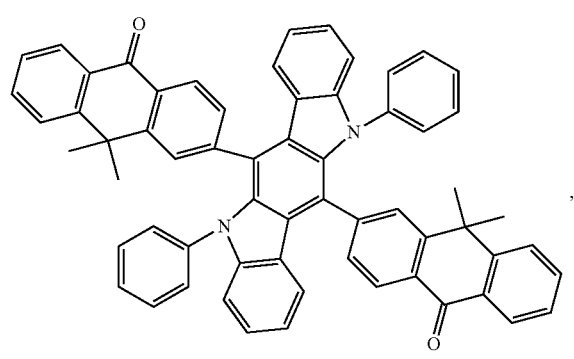
M44
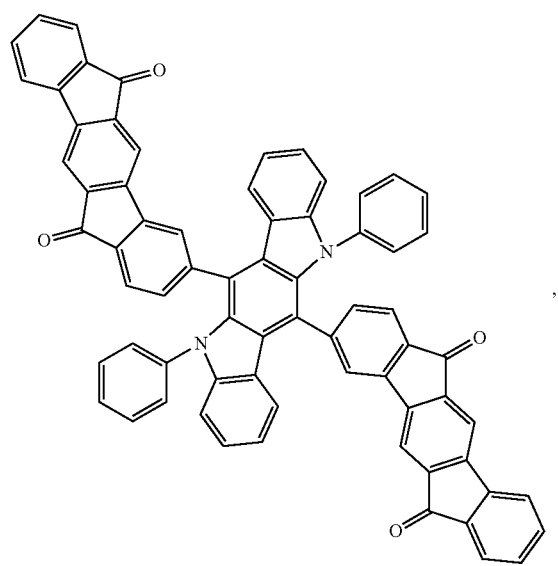
M45
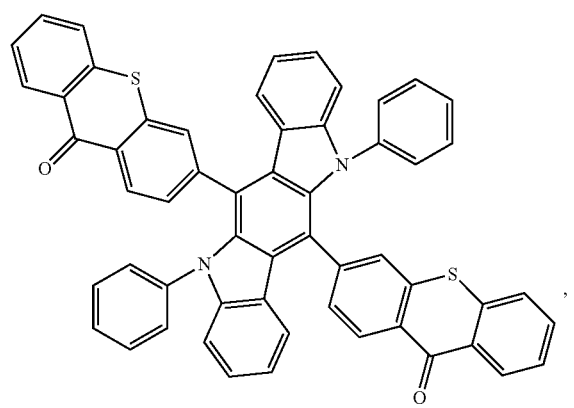

-continued
M46
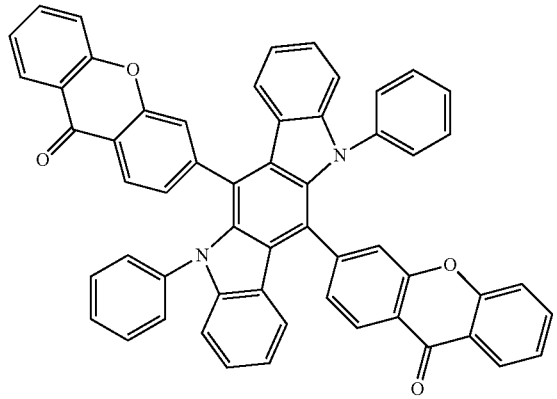,
M47
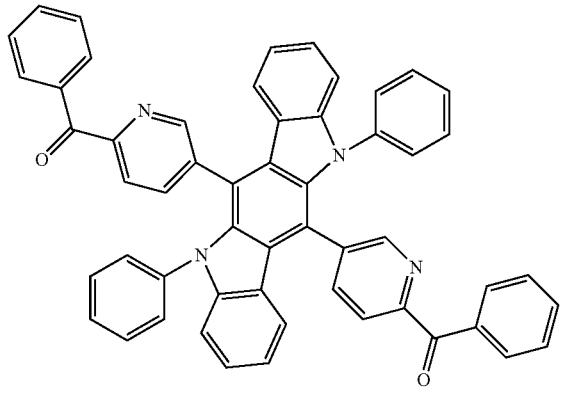,
M48
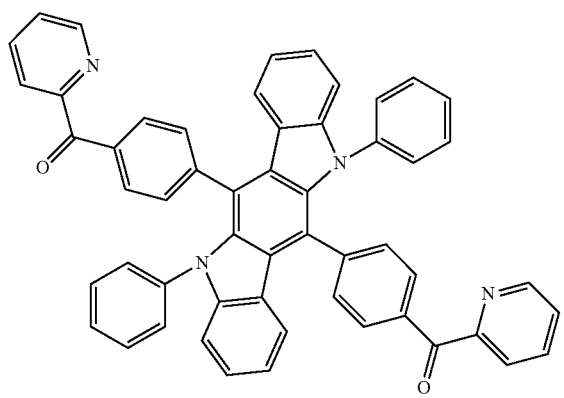,
M49
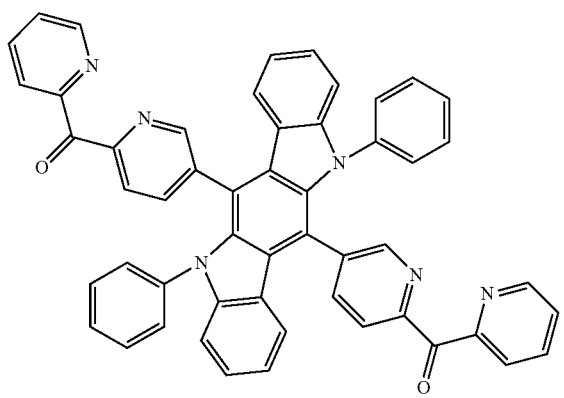,
M50
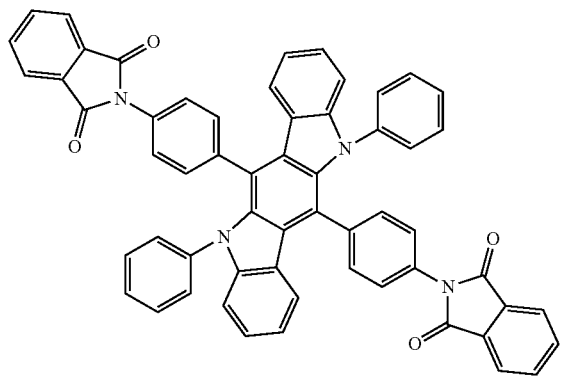,
M51
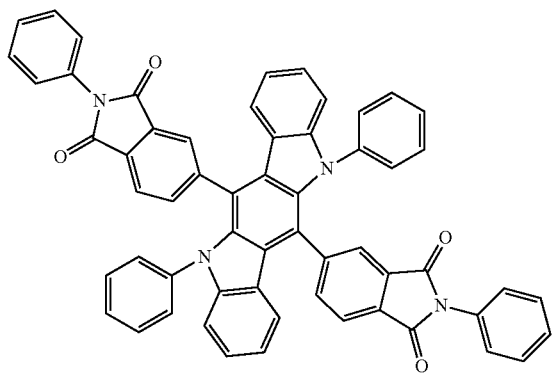,
M52
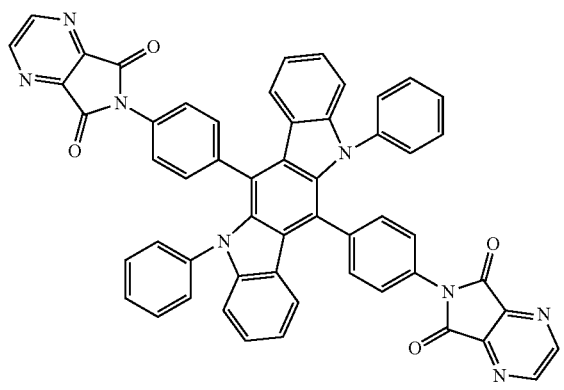,
M53
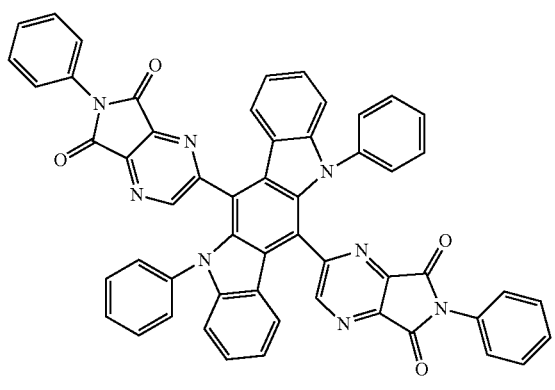,

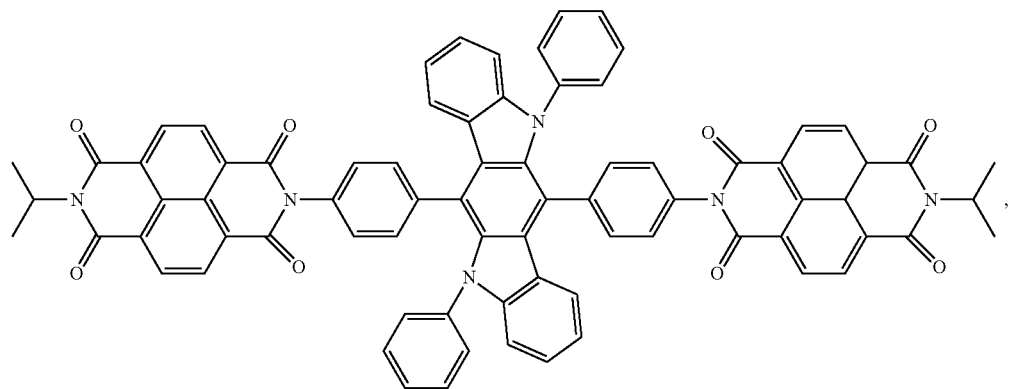
M54
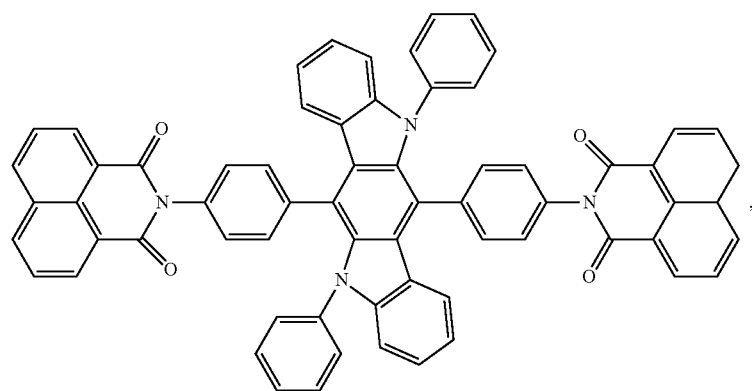
M55
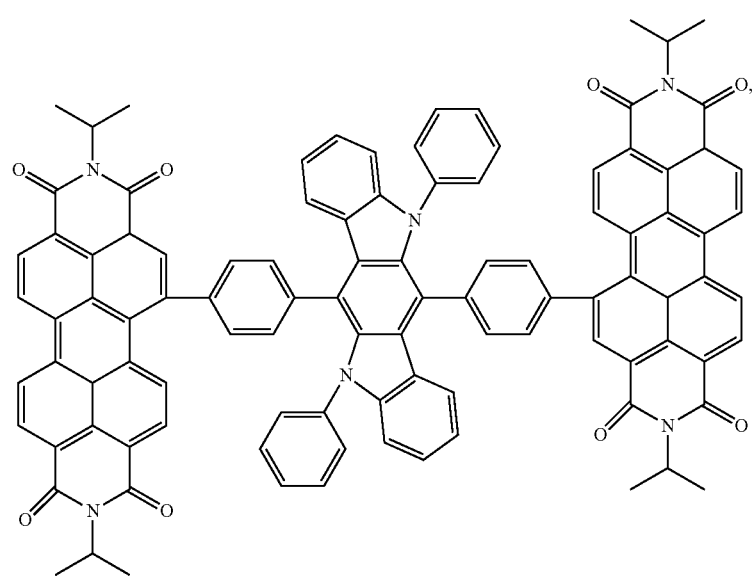
M56

-continued
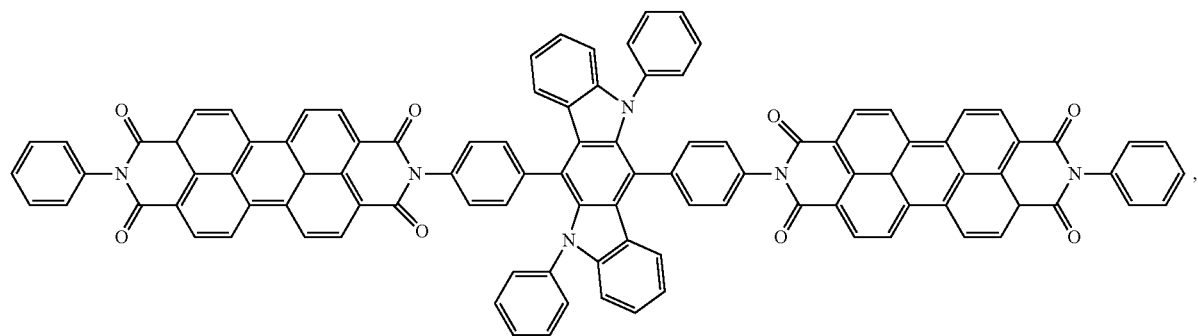
M57
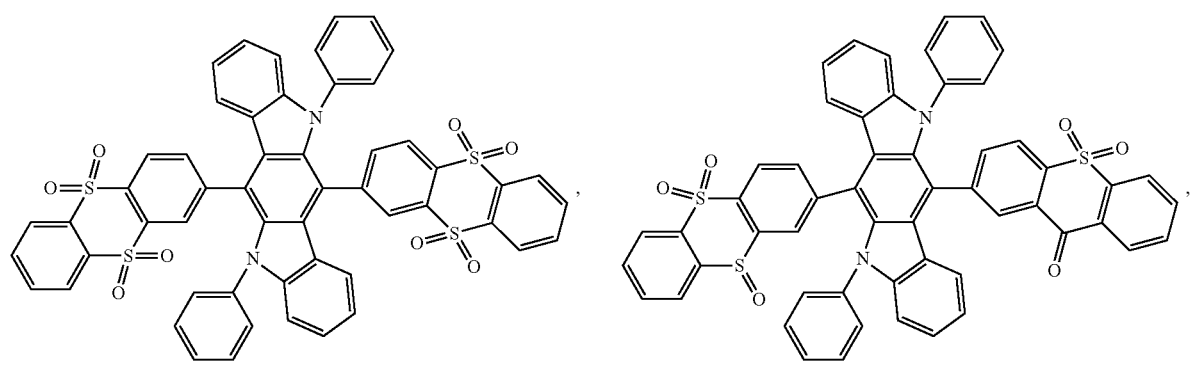
M58
M59
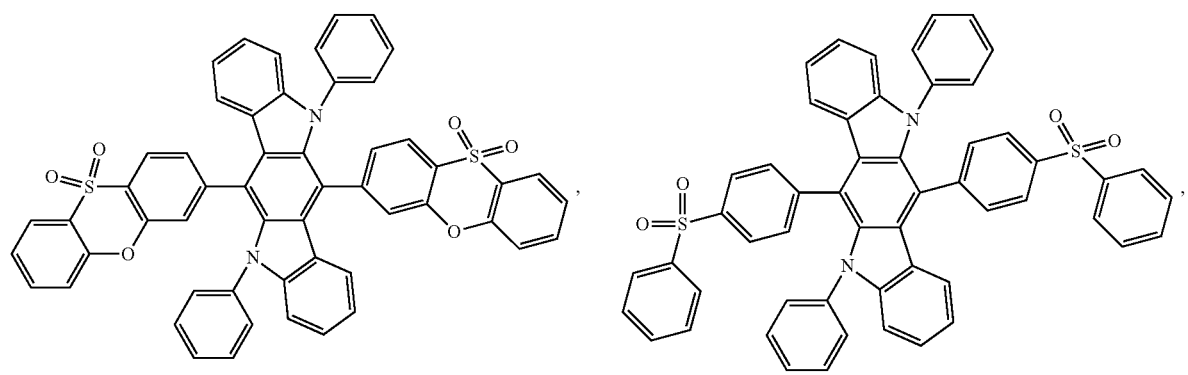
M60
M61

-continued
M62
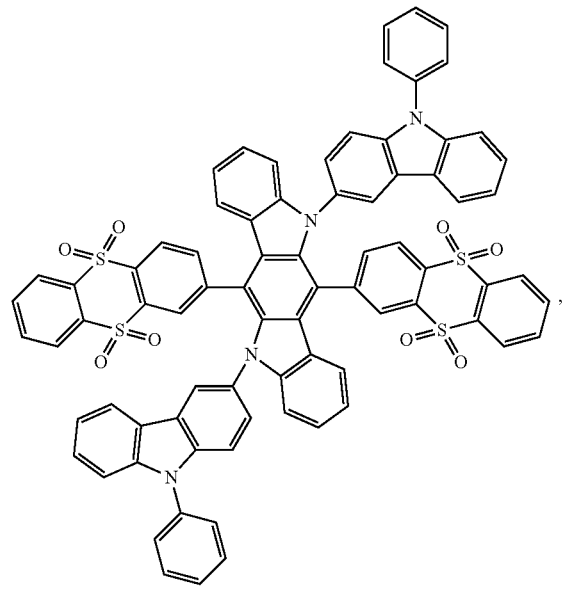
M63
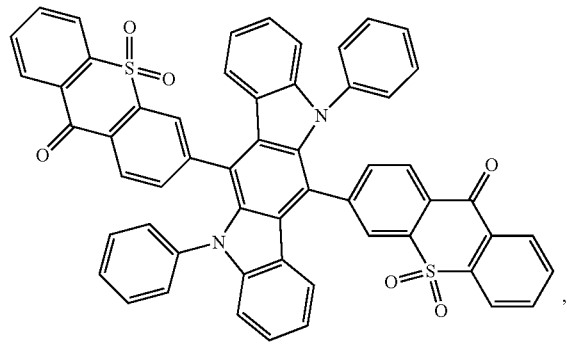
M64
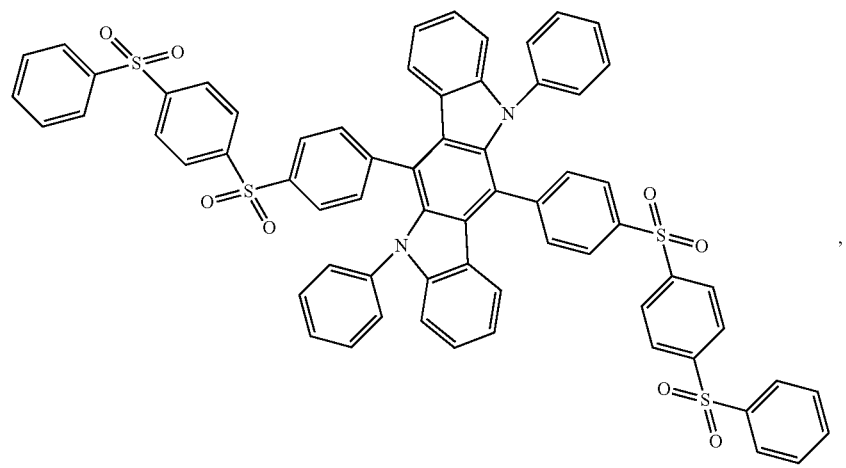
M65
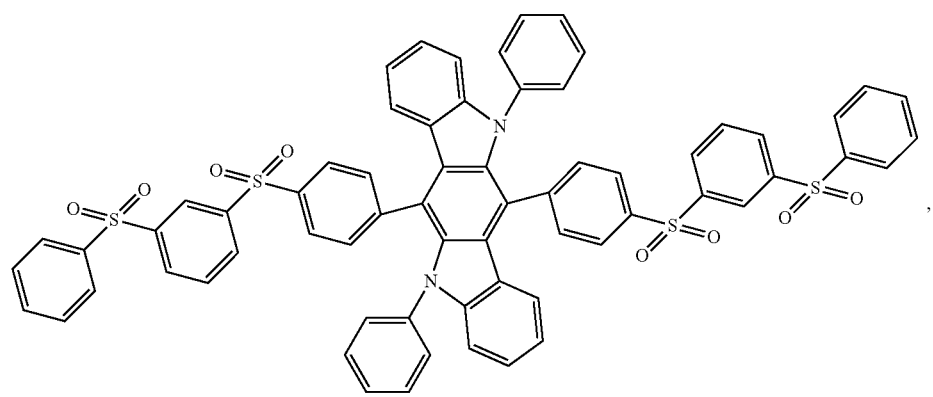

-continued
M66
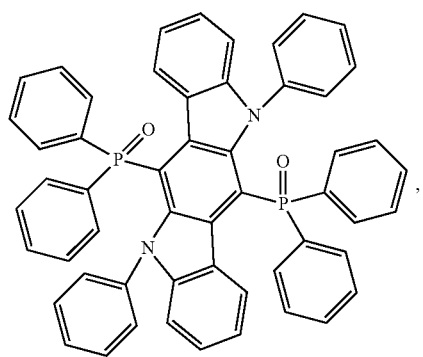
M67
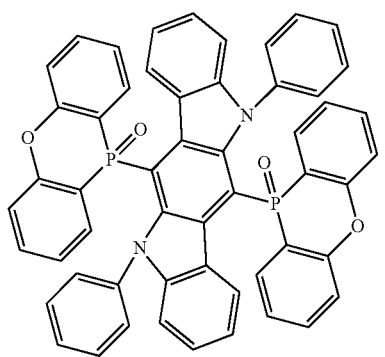
M68
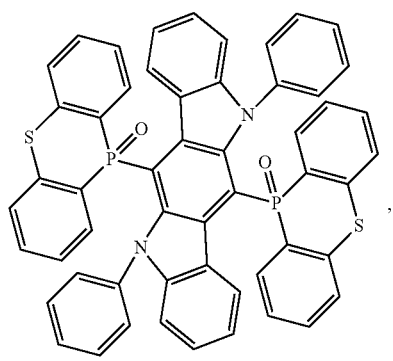
M69
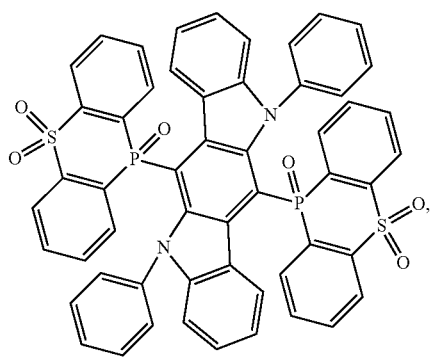
M70
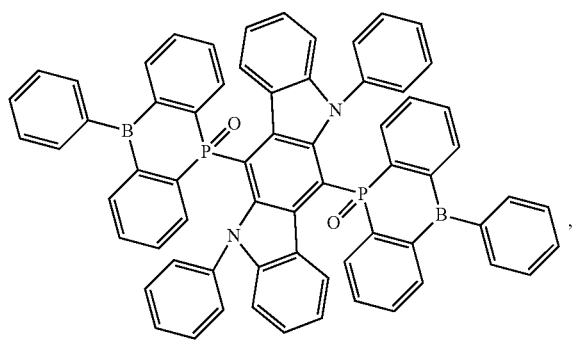
M71
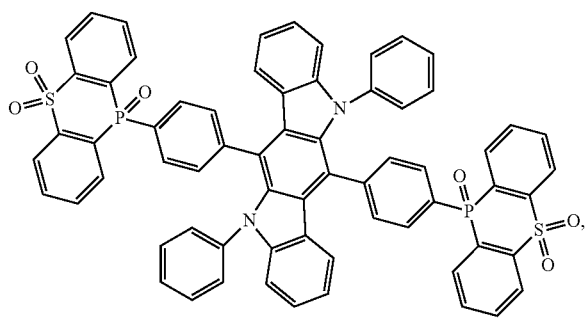

-continued
M72
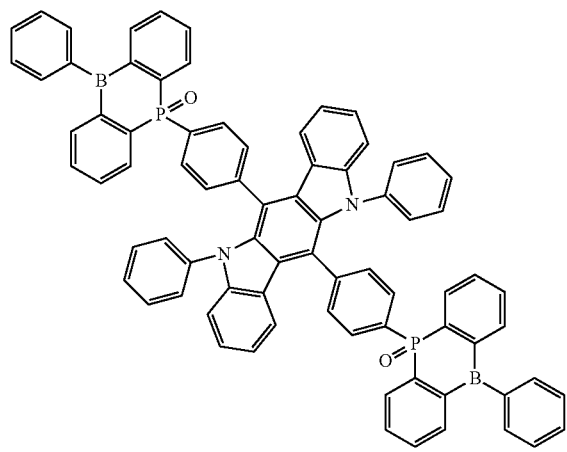
M73
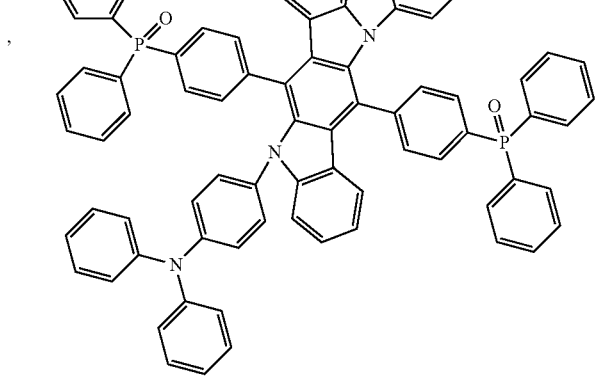
M74
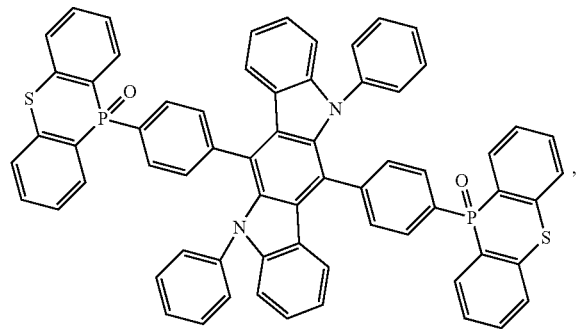
M75
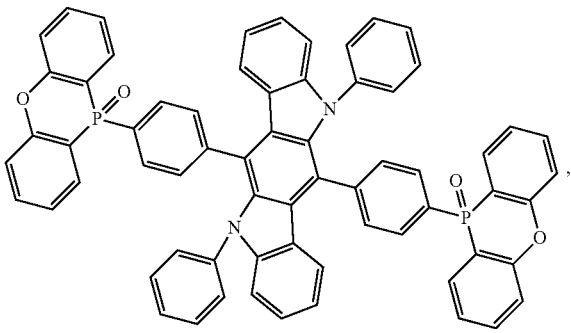
M78
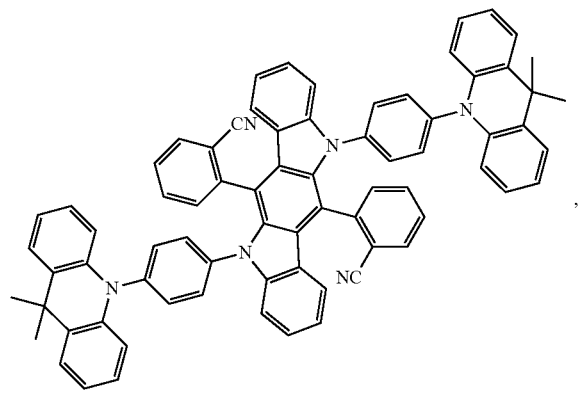
M79
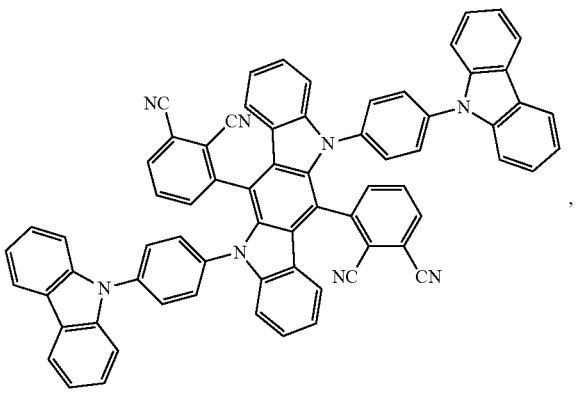

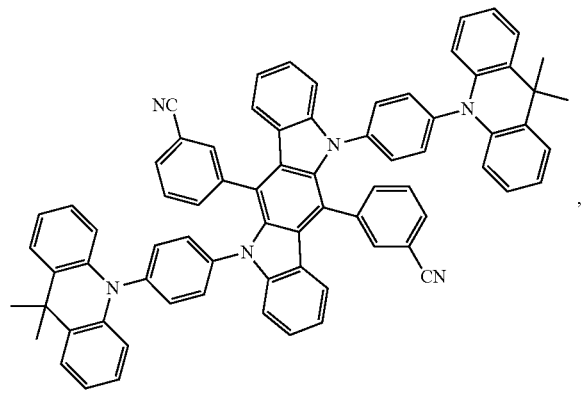
M80
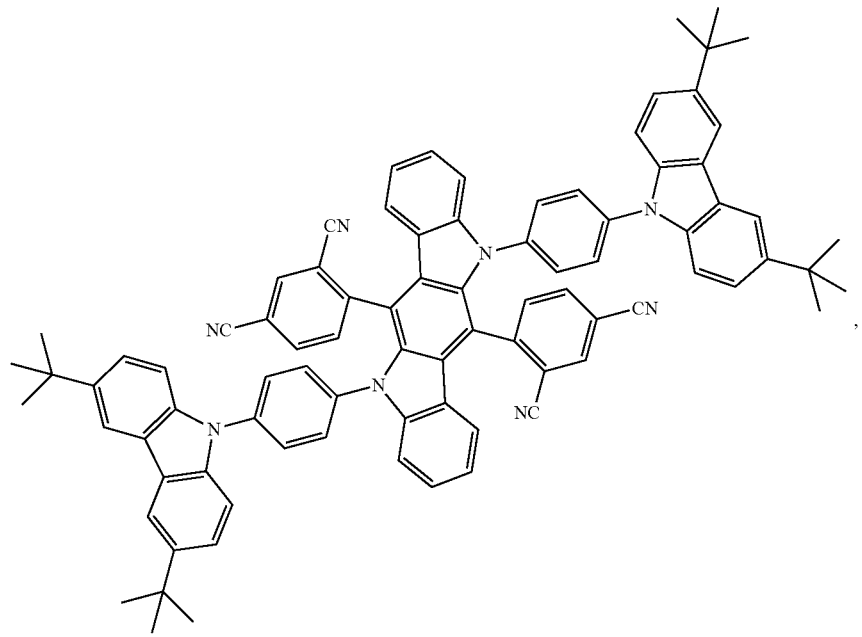
M81
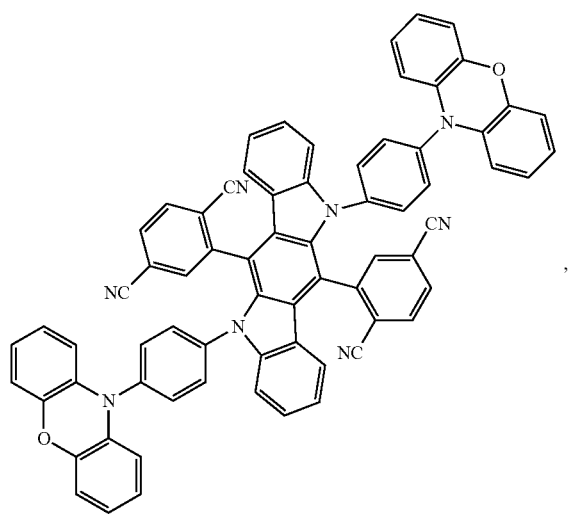
M82
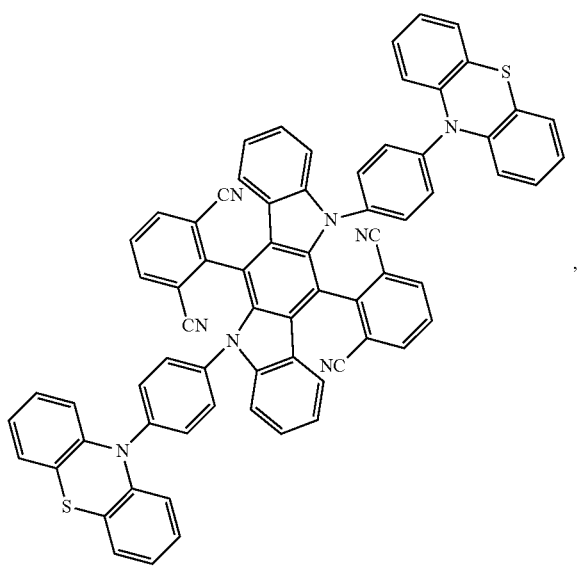
M83

-continued
M84
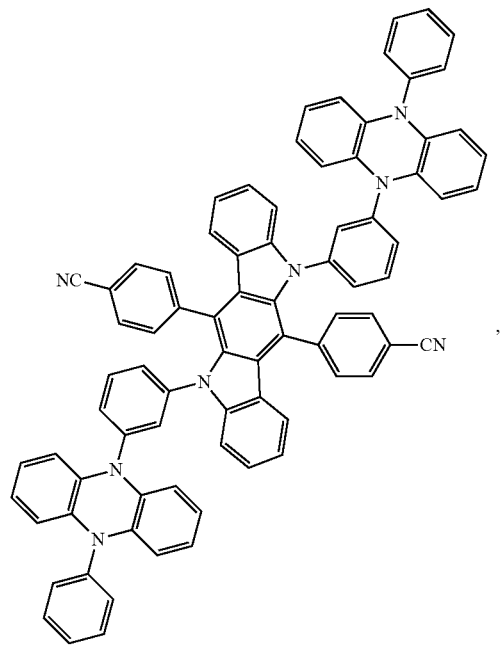
M85
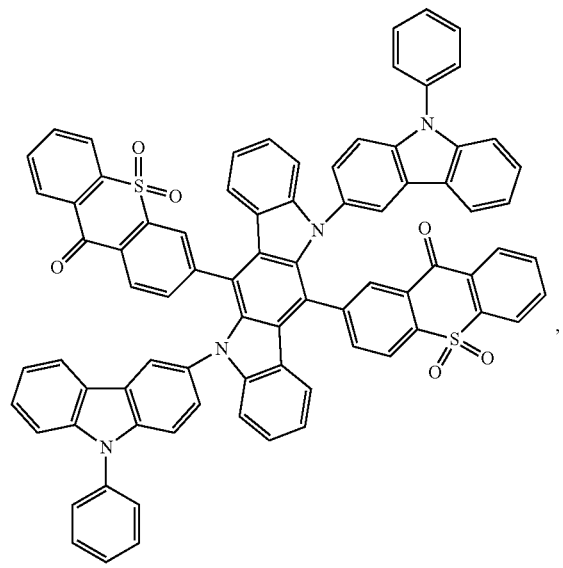
M86
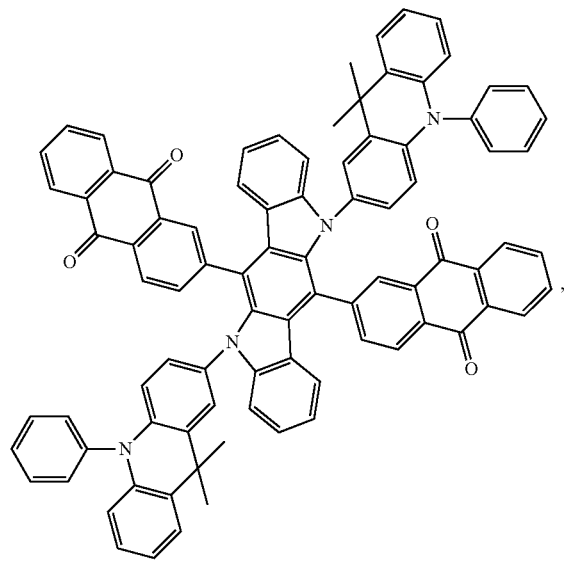
M87
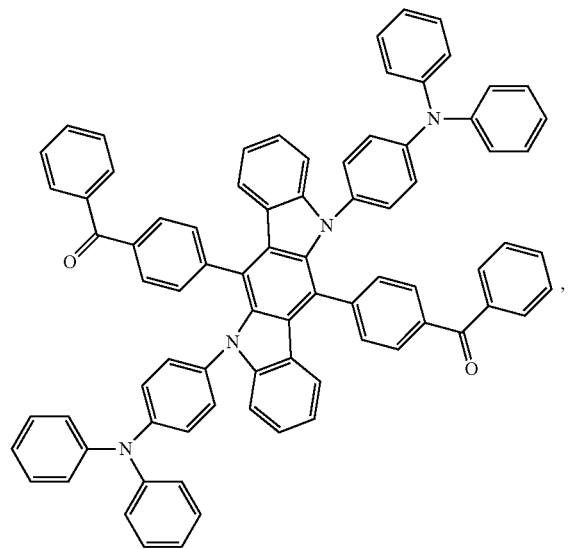

-continued
M88
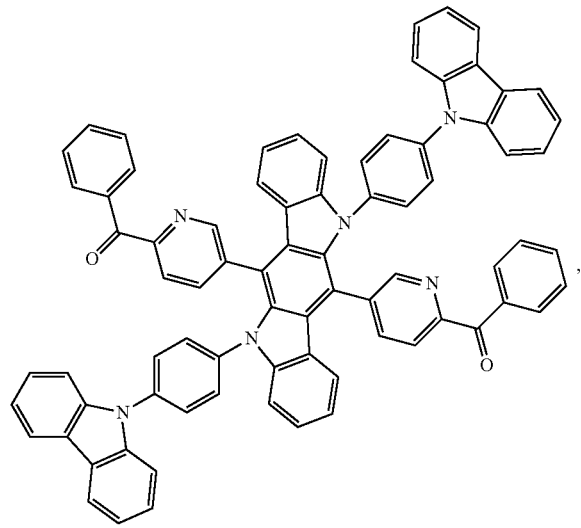
M89
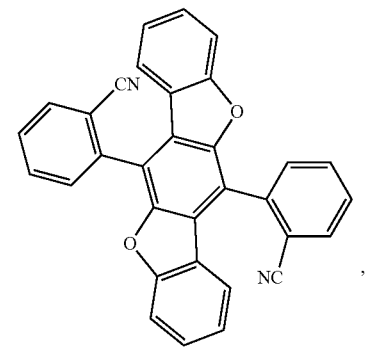
M90
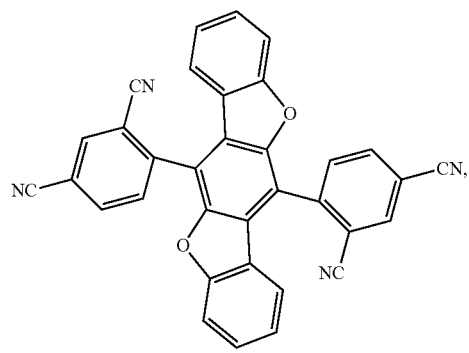
M91
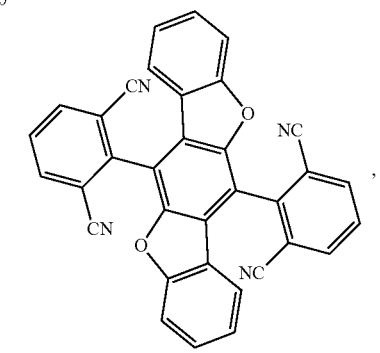
M92
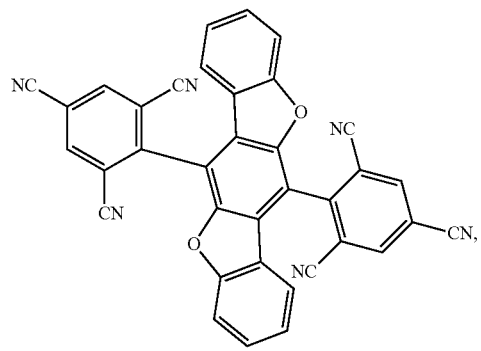
M93
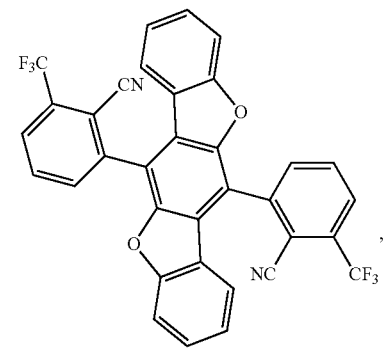
M94
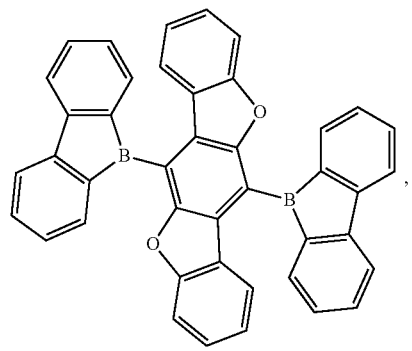
M95
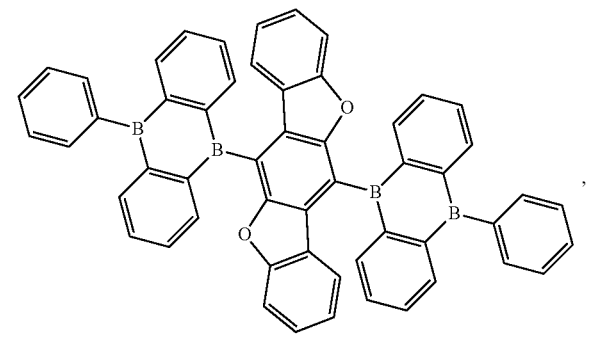

-continued
M96
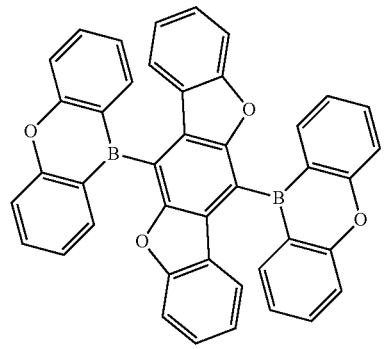
M97
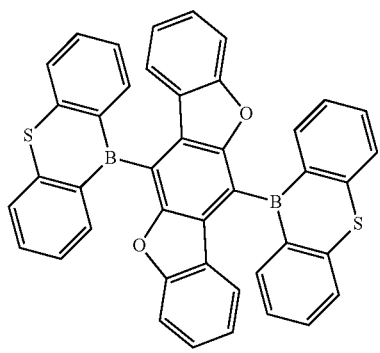
M98
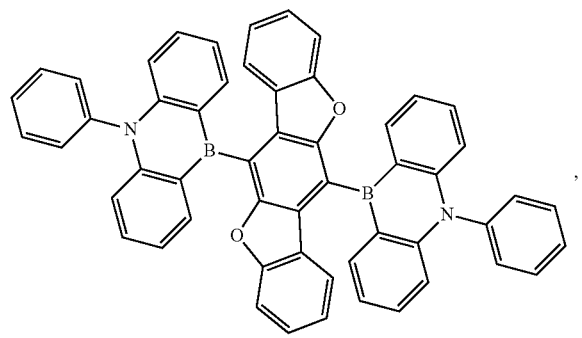
M99
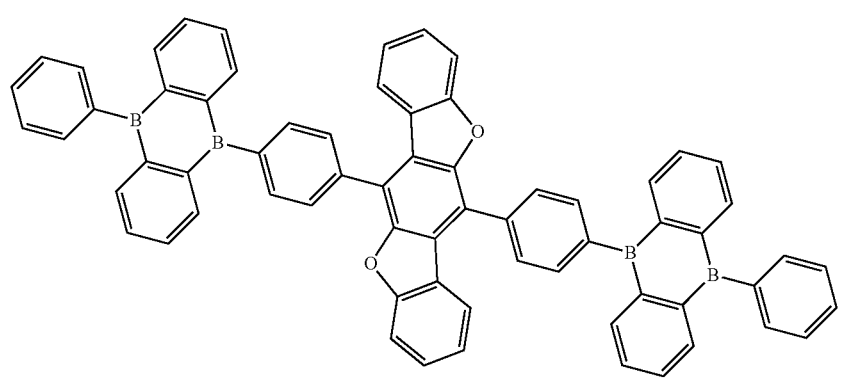
M100
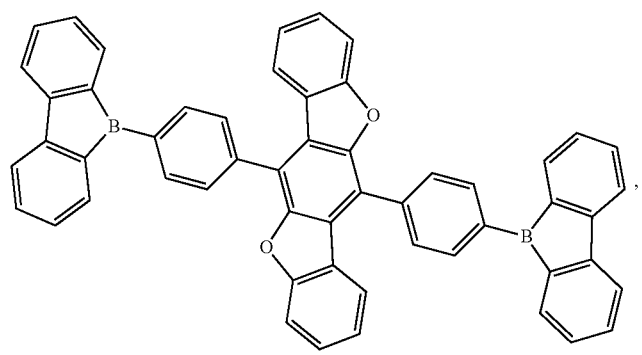

M101
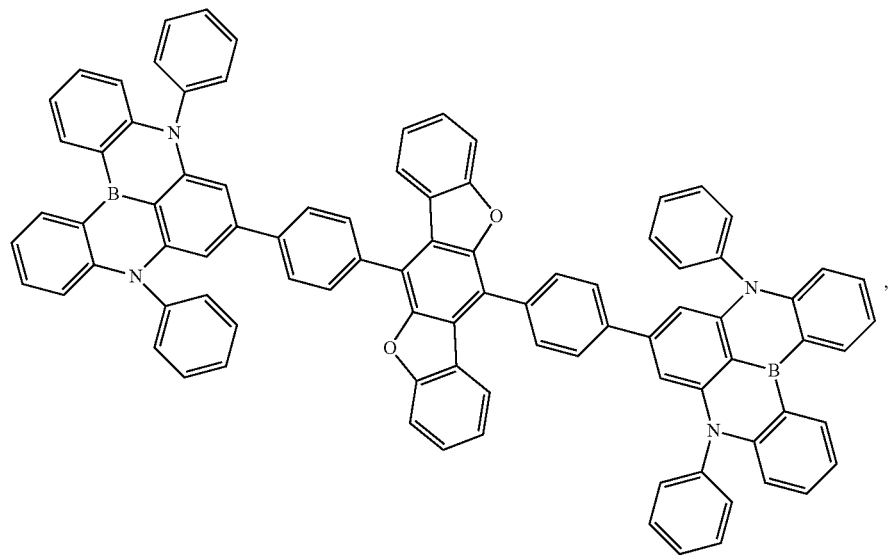
M102
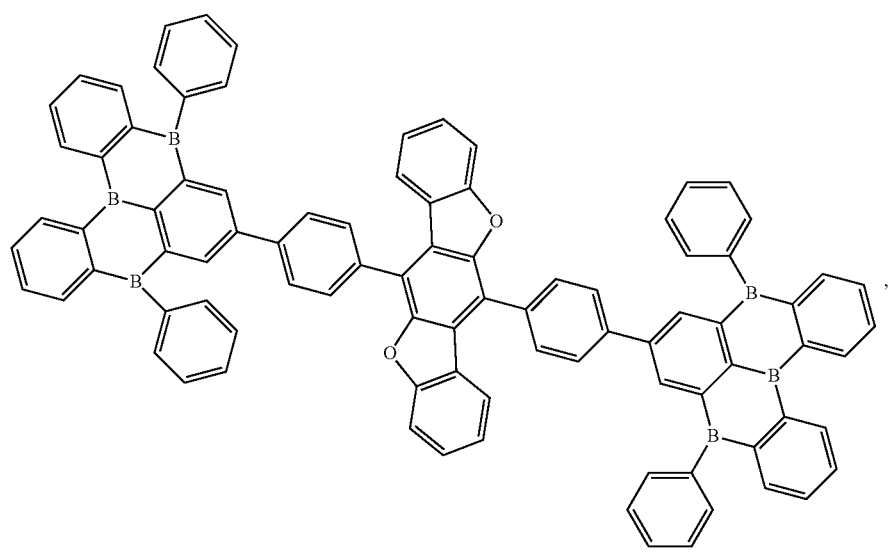
M103
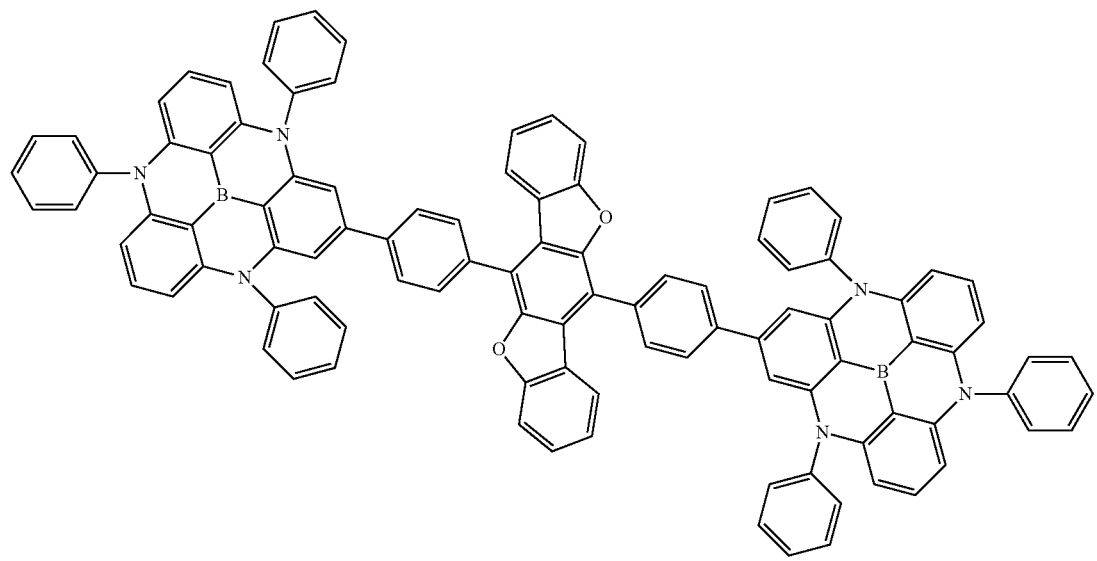

-continued
M104
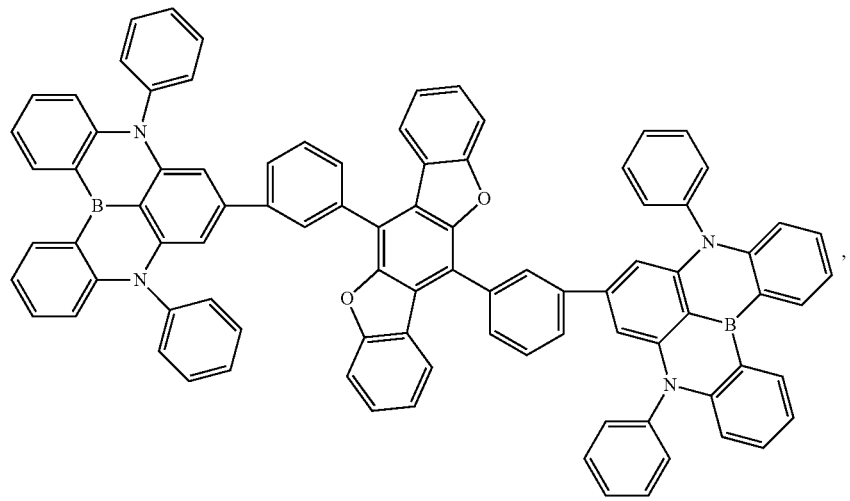
M105 M106
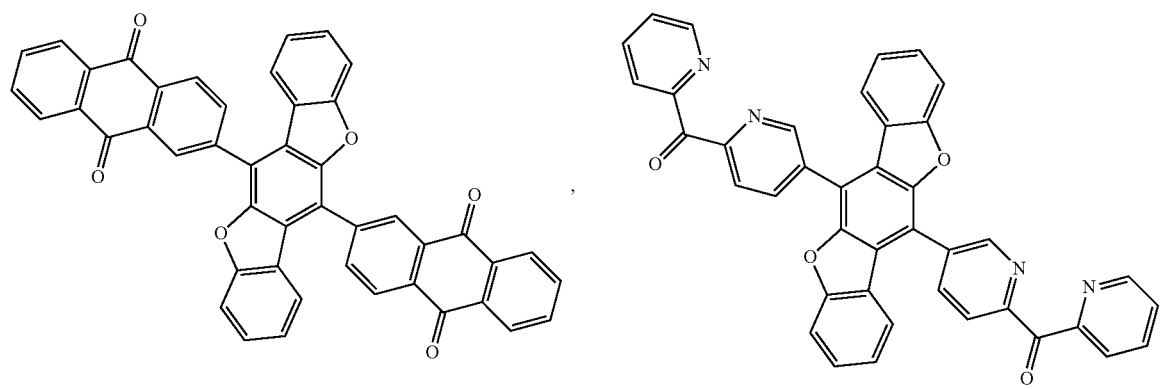
M107 M108
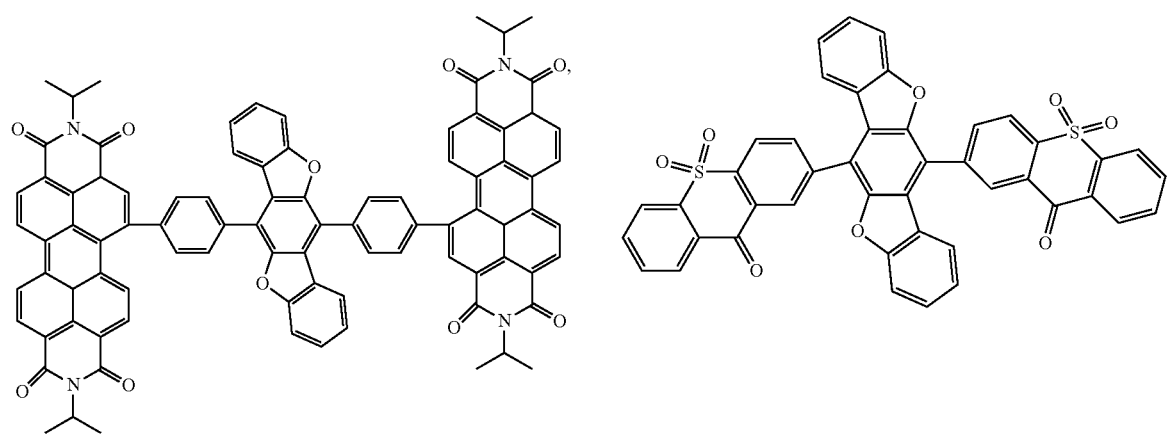

-continued
M109
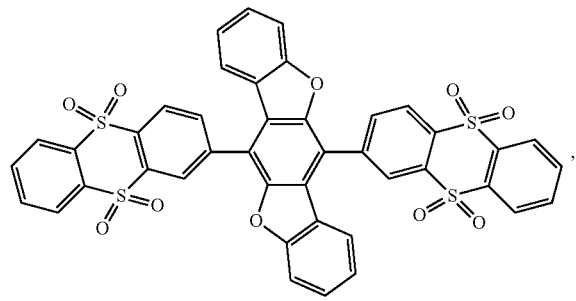,
M110
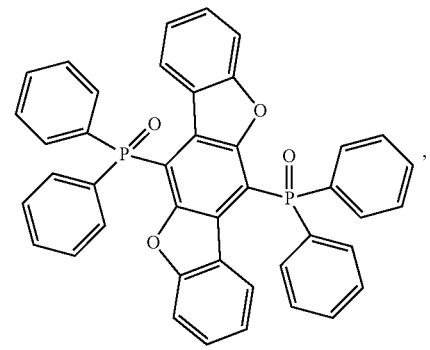,
M111
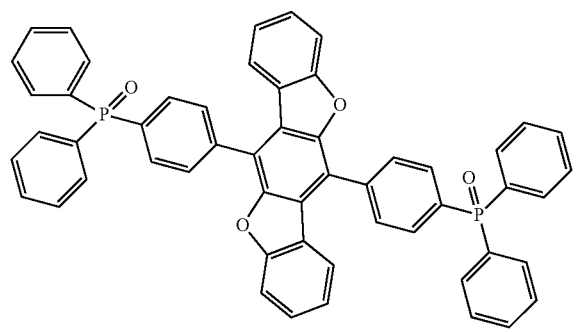,
M112
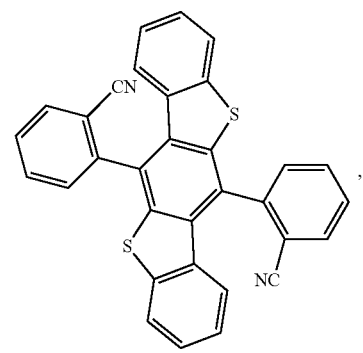,
M113
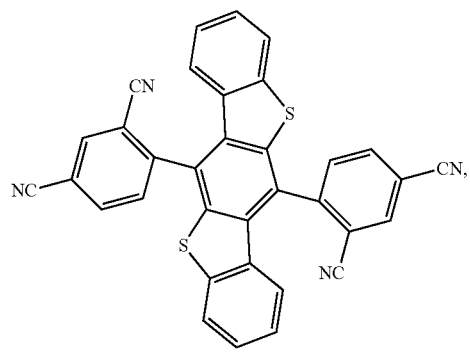,
M114
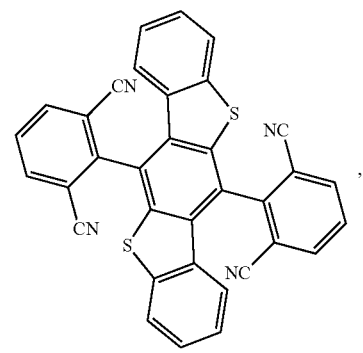,
M115
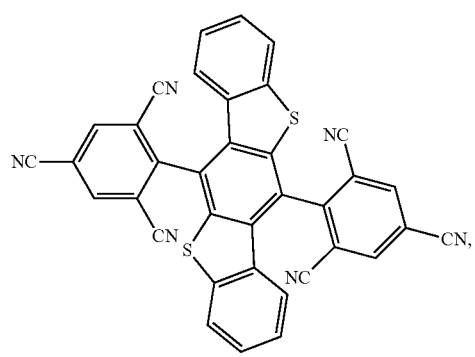,
M116
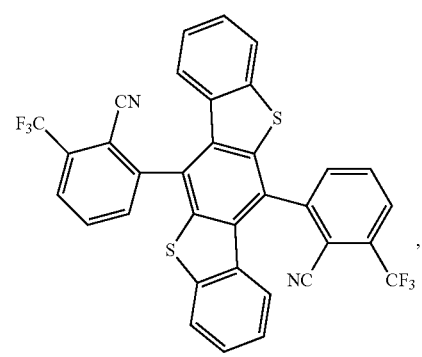, -continued
M117
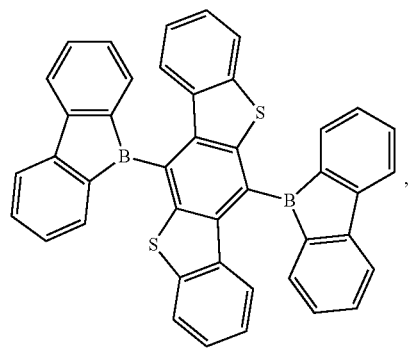
M118
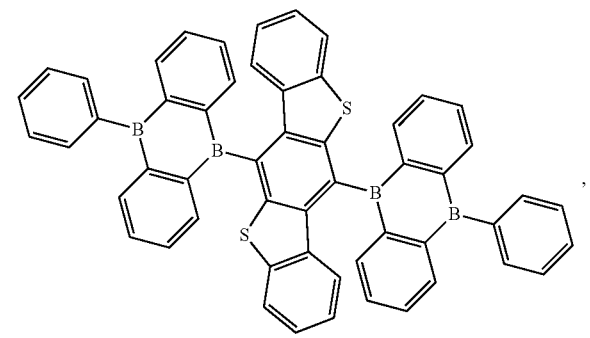
M119
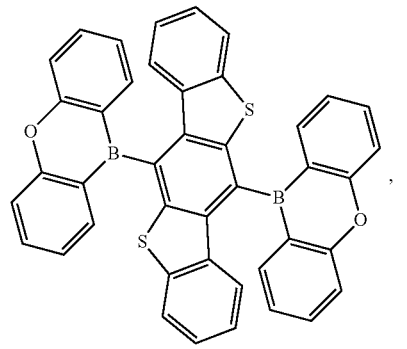
M120
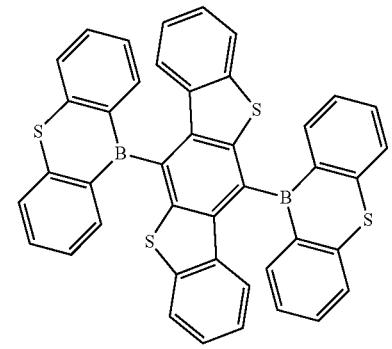
M121
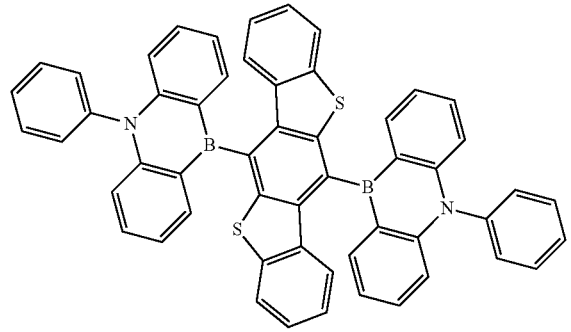
M122
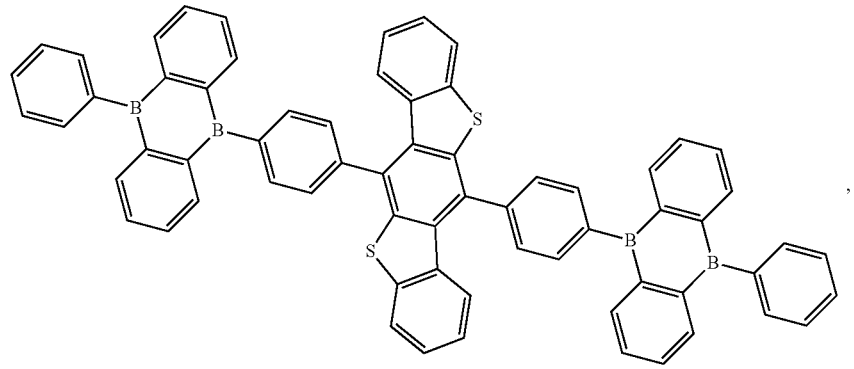

M123
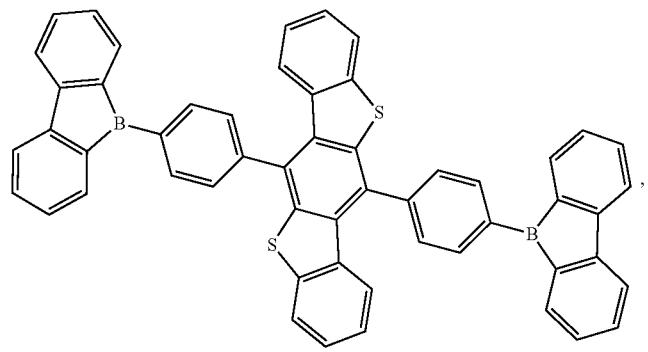
M124
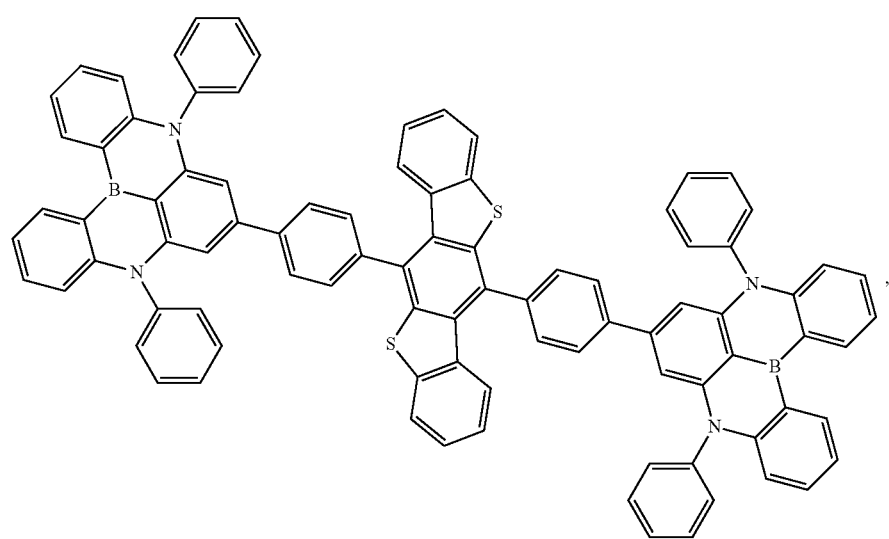
M125
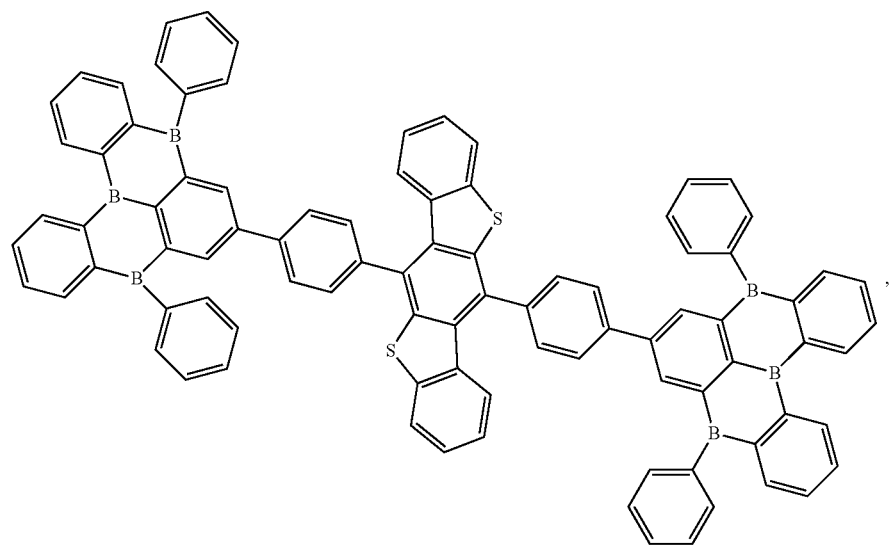

-continued
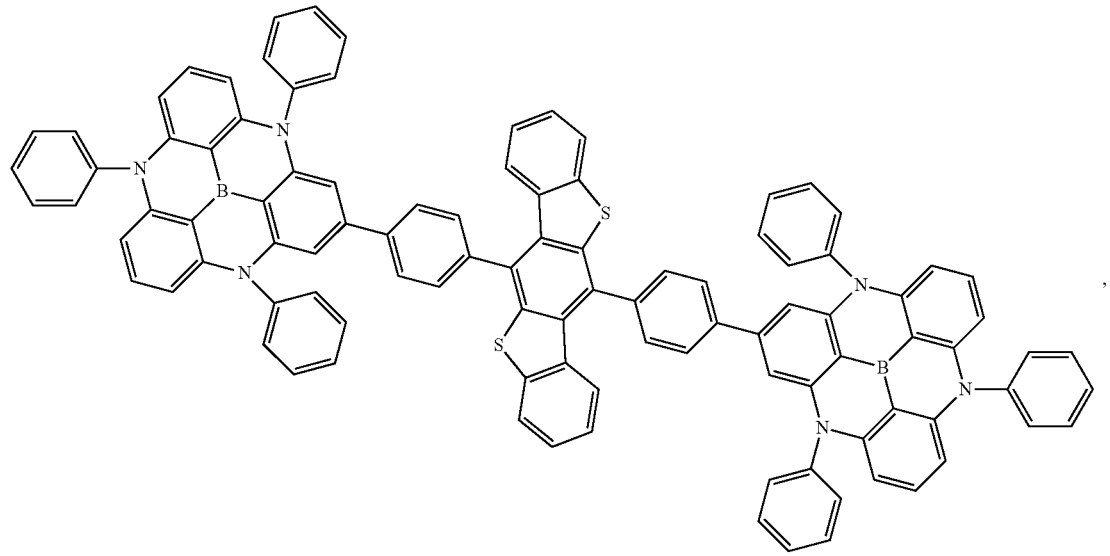
M126
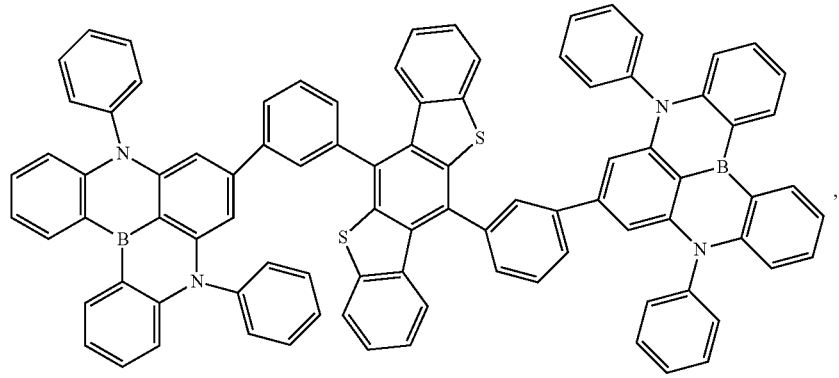
M127
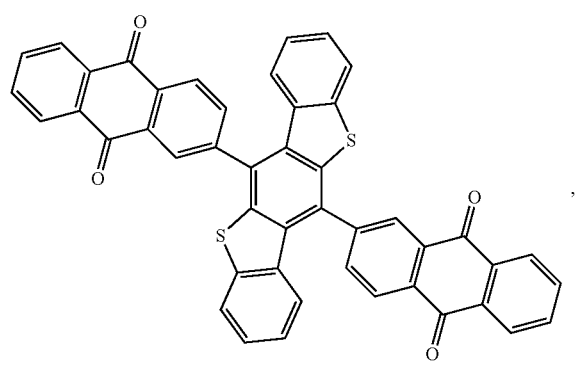
M128
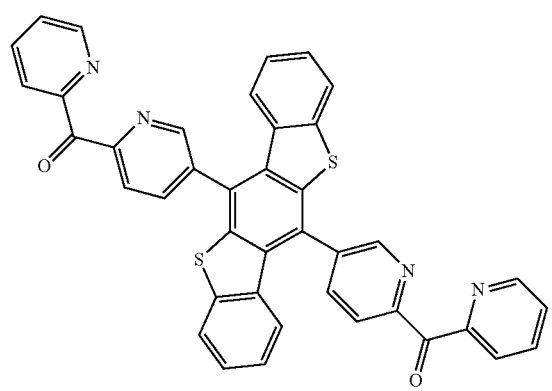
M129

M130

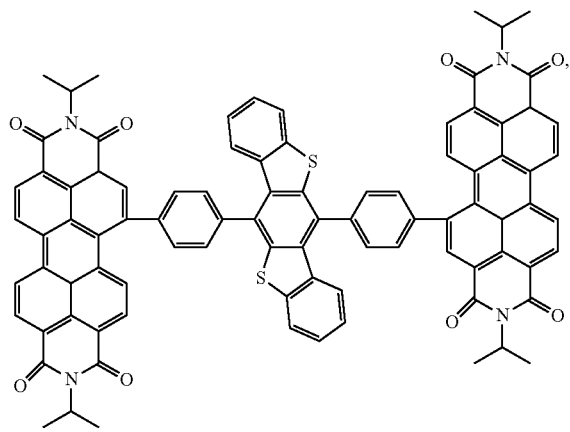

M131

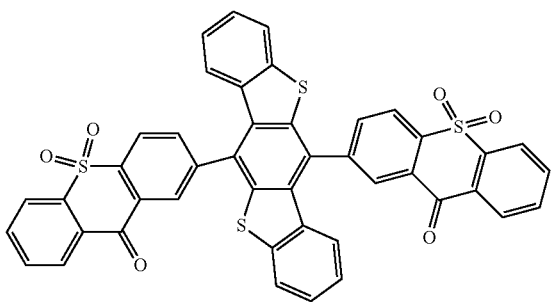

M132

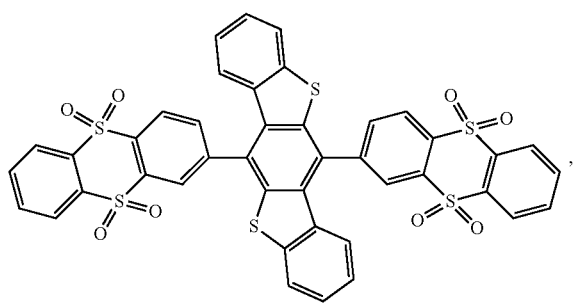

M133

, and

M134

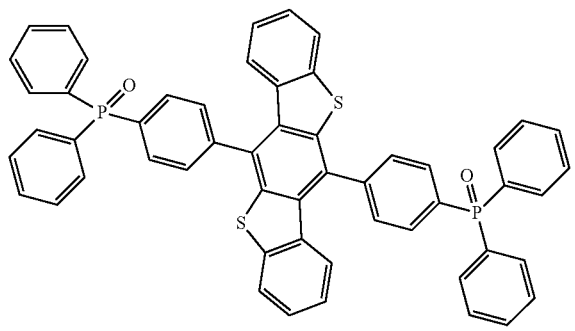

14. A display panel, comprising an OLED device, wherein the OLED device comprises an anode, a cathode, and at least one organic thin film layer between the anode and the cathode, wherein the organic thin film layer comprises a light emitting layer; any one or a combination of at least two of a hole transport layer, a hole injection layer, an electron blocking layer, a hole blocking layer, an electron transport layer, and an electron injection layer;
wherein the light emitting layer comprises the compound according to claim 1, wherein the compound is used as any one of a host material, a doping material, and a co-doping material.

15. The display panel according to claim 14, wherein the light emitting layer comprises a host material and a doping material, and the host material comprises the compound according to claim 1.

16. An electronic device, comprising the display panel according to claim 14.

* * * * *